(12) United States Patent
Gerhard et al.

(10) Patent No.: US 10,018,628 B2
(45) Date of Patent: Jul. 10, 2018

(54) METHOD FOR THE DETECTION OF H. PYLORI INFECTION

(71) Applicant: Technische Universität München, München (DE)

(72) Inventors: Markus Gerhard, Munich (DE); Behnam Kalali, Munich (DE); Luca Formichella, Munich (DE); Mohammad Khalife-Gholi, Ghom (IR)

(73) Assignee: TECHNISCHE UNIVERSITAT MUNCHEN, Munich (DE)

( * ) Notice: Subject to any disclaimer, the term of this patent is extended or adjusted under 35 U.S.C. 154(b) by 142 days.

(21) Appl. No.: 14/911,426

(22) PCT Filed: Aug. 13, 2014

(86) PCT No.: PCT/EP2014/002230
§ 371 (c)(1),
(2) Date: Feb. 10, 2016

(87) PCT Pub. No.: WO2015/022075
PCT Pub. Date: Feb. 19, 2015

(65) Prior Publication Data
US 2016/0195528 A1   Jul. 7, 2016

(30) Foreign Application Priority Data
Aug. 13, 2013   (EP) .................................... 13004038

(51) Int. Cl.
 *C07K 1/00* (2006.01)
 *G01N 33/569* (2006.01)
 *C07K 16/12* (2006.01)

(52) U.S. Cl.
 CPC ..... *G01N 33/56922* (2013.01); *C07K 16/121* (2013.01); *G01N 2469/20* (2013.01)

(58) Field of Classification Search
 CPC ................................................ G01N 33/56922
 See application file for complete search history.

(56) References Cited

U.S. PATENT DOCUMENTS
2004/0052799 A1   3/2004  Smith et al.

FOREIGN PATENT DOCUMENTS
| JP | 2006284567 A | 10/2006 |
| WO | WO 96/40893 A1 | 12/1996 |
| WO | WO 98/27432 | 6/1998 |
| WO | WO 2004/094467 | 11/2004 |

OTHER PUBLICATIONS
Baltrus et al (Journal of Bacteriology vol. 191, No. 1, pp. 447-448) (Year: 2009).*
International Search Report & Written Opinion, International Application No. PCT/EP2014/002230, dated Apr. 7, 2015, 12 pages.
M. Khalifeh Gholi et al., "Helicobacter pylori FliD protein is a highly sensitive and specific marker for serologic diagnosis of H. pylori infection," Internal Journal of Medical Microbiology 303(8):618-623, Dec. 8, 2013.
Examination Report corresponding to European Patent Application No. EP 14755023.0, dated Nov. 6, 2017.

* cited by examiner

*Primary Examiner* — Albert M Navarro
(74) *Attorney, Agent, or Firm* — Leydig, Voit & Mayer, Ltd.

(57) ABSTRACT

The present invention is related to a method for detecting *H. pylori* infection in a subject, wherein the method comprises detecting in a sample from the subject an immune response against FliD, wherein the immune response comprises an anti-FliD antibody.

17 Claims, 7 Drawing Sheets

METHOD FOR THE DETECTION OF H. PYLORI INFECTION

CROSS-REFERENCE TO RELATED APPLICATIONS

This application is a U.S. National Stage Application under 35 U.S.C. § 371 of International Application No. PCT/EP2014/002230, filed Aug. 13, 2014, which claims the benefit of and priority to European Patent Application No. 13004038.9, filed Aug. 13, 2013. Each of these applications is hereby incorporated by reference in its entirety.

REFERENCE TO A SEQUENCE LISTING

A sequence listing containing SEQ ID NOs: 1-28 is provided herewith and is specifically incorporated by reference.

The present invention is related to a method for detecting *Helicobacter* infection and more particularly *H. pylori* infection, use of an immune response as a biomarker, use of a *Helicobacter* protein as a biomarker, use of a nucleic acid coding for a *Helicobacter* protein as a biomarker, and a kit for use in the method for detecting *Helicobacter* infection and more particularly *H. pylori* infection.

*Helicobacter pylori* (*H. pylori*), a microaerophilic, Gram-negative and spiral bacterium is colonizing approximately half of the world population and considered to be a human-specific gastric pathogen (Michetti, et al., 1999). Most infected individuals develop asymptomatic chronic gastritis. However, in some subjects the infection causes chronic gastritis, peptic ulceration and atrophy, and plays an important role in the development of mucosa-associated lymphoid tissue (MALT) lymphoma, gastric adenocarcinoma and primary gastric non-Hodgkin's lymphoma (Suganuma, et al., 2001).

The World Health Organization has categorized *H. pylori* as a class I carcinogen (Goto, et al., 1999), and direct evidence of carcinogenesis has been demonstrated in animal models (Honda, et al., 1998; T. Watanabe, et al., 1998). Eradication of *H. pylori* can prevent gastric cancer in humans (Uemura, et al., 2001). Test & treat strategies have been considered in populations with high gastric cancer risk (Yamaoka, et al., 1998). However, such approach is hampered by the lack of efficient and affordable screening systems especially for countries of lower socioeconomic status. In these countries only serologic tests are applicable, most of which suffer from poor performance or are not well validated. For *H. pylori* serology there are several specific single markers known and described. These factors have been applied in many diagnostic approaches, but almost all of them have significant limitations which make them unsuitable for *H. pylori* diagnosis. For instance, the cytotoxin-associated protein (CagA) is a very well characterized *H. pylori* protein. It is encoded on the cag-PAI (cytotoxin associated gene Pathogenicity Island) and is described as an oncogenic protein (Franco, et al., 2005; Murata-Kamiya, et al., 2007). This protein is also a highly immunogenic antigen, making it a frequently employed marker for serologic tests. CagA positivity can be used as an indicator of *H. pylori* virulence because individuals infected with CagA positive strains are at a higher risk for developing gastroduodenal diseases. However, it is not suitable as a single marker, since only a subgroup of *H. pylori* strains are CagA positive. Moreover, CagA positivity is not a hallmark of active infection as *H. pylori* eradicated patients maintain antibodies against CagA for many years (Fusconi, et al., 1999). Therefore it should always be combined with other suitable antigens in serologic tests to confirm positivity. Another well-characterized *H. pylori* protein is the vacuolating cytotoxin (VacA). It was reported to induce vacuolation in cells exposed to *H. pylori* supernatants or purified protein (Cover & Blaser, 1992). The vacA gene codes for a 140 kDa pro-toxin, where the amino-terminal signal sequence and the carboxy-terminal fragment are proteolytically cleaved during secretion, leading to an active protein with a molecular mass of 88 kDa that aggregates to hexamers and forms a pore (Montecucco & de Bernard, 2003). This protein consists of two different regions. A signal sequence (s1a, s1b, s2) and a mid-region (m1, m2), both with high allelic variations which appear to regulate cytotoxic activity (Atherton, et al., 1995). The high diversity of VacA makes this protein unsuitable for serologic testing.

Another well characterized *H. pylori* protein, GroEL, belongs to the family of molecular chaperones, which are required for the proper folding of many proteins under stress conditions (Dunn, et al., 1992). In different studies it was shown that this protein is highly conserved among different *H. pylori* strains and that its seropositivity was even higher than for the CagA in infected patients (Macchia, et al., 1993; Suerbaum, et al., 1994). Also, in studies performed by the instant inventors it was observed that a positive serostatus for GroEL was more often found in German gastric cancer patients compared to matched controls (unpublished data). Also, it is suggested that antibodies against GroEL might persist longer after disease-related loss of *H. pylori* infection. Thus, GroEL may be a suitable marker of either current or past infection, and may be helpful to overcome the underestimation of *H. pylori*-related gastric cancer risk due to clearance of infection (Gao et al., 2009).

Therefore, the problem underlying the present invention was the provision of a method for detecting *H. pylori* infection with high sensitivity and/or high specificity. Another problem underlying the present invention was the provision of an assay which, compared to the assays of the prior art, leads to less false positive and less false negative results, particularly in population-based approaches. A further problem underlying the present invention was to provide means for carrying out such methods and such assays, respectively. A still further problem underlying the present invention was the provision of a biomarker for *H. pylori* infected patients, whereby the biomarker preferably does not show any cross-reactivity with other bacteria and any proteins, peptides or nucleic acid molecules coding for such proteins and peptides in particular.

These and other problems underlying the present invention are solved by the subject matter of the attached independent claims. Preferred embodiments may be taken from the attached dependent claims.

These and other problems underlying the present invention are also solved by the following embodiments.

EMBODIMENT 1

A method for detecting *Helicobacter* infection and more preferably an *H. pylori* infection in a subject, wherein the method comprises detecting in a sample from the subject an immune response against FliD.

EMBODIMENT 2

The method of Embodiment 1, wherein if an immune response against FliD is detected in the sample from the subject, the subject is suffering from a *Helicobacter* infection, preferably an *H. pylori* infection, or the subject has undergone a *Helicobacter* infection, preferably an *H. pylori* infection, in the past.

EMBODIMENT 3

The method of any one of Embodiments 1 to 2, wherein if no immune response against FliD is detected in the sample from the subject, the subject is not suffering from a *Helicobacter* infection, preferably an *H. pylori* infection.

EMBODIMENT 4

The method of any one of Embodiments 1 to 2, wherein if no immune response against FliD is detected in the sample from the subject, the subject has undergone a *Helicobacter* infection, preferably an *H. pylori* infection, in the past.

EMBODIMENT 5

The method of any one of Embodiments 1 to 4, wherein the immune response against FliD is an antibody response against FliD, preferably an anti-FliD antibody response.

EMBODIMENT 6

The method of Embodiment 5, wherein the immune response against FliD is an antibody response against FliD and wherein the antibody response against FliD comprises at least one anti-FliD antibody selected from the group comprising an IgG antibody and an IgA antibody.

EMBODIMENT 7

The method of Embodiment 5, wherein the immune response against FliD is an anti-FliD antibody response and wherein the anti-FliD antibody response comprises at least one anti-FliD antibody selected from the group comprising an IgG antibody and an IgA antibody.

EMBODIMENT 8

The method of any one of Embodiments 1 to 7, wherein the subject is infected with *Helicobacter*, preferably *H. pylori*, expressing FliD.

EMBODIMENT 9

The method of any one of Embodiments 1 to 8, wherein the subject is different from a subject which is immunosuppressed, preferably the subject is different from a subject which is under immunosuppressive therapy.

EMBODIMENT 10

The method of any one of Embodiments 1 to 9, wherein the method further comprises detecting one or more antigens of *Helicobacter*, preferably of *H. pylori*.

EMBODIMENT 11

The method of Embodiment 10, wherein the one or more antigens of *Helicobacter*, preferably *H. pylori*, is selected from the group comprising CagA, VacA, GroEL, Hp 0231, JHp 0940 and HtrA.

EMBODIMENT 12

The method of any one of Embodiments 1 to 11, wherein the method comprises reacting the sample with FliD or a fragment thereof.

EMBODIMENT 13

The method of Embodiment 13, wherein the method comprises reacting the sample with a full-length FliD.

EMBODIMENT 14

The method of any one of Embodiments 12 to 13, wherein the immune response against FliD comprises at least one of a humoral compound capable of interacting with FliD and a cellular compound capable of interacting with FliD, wherein the at least one humoral compound and/or cellular compound interacts with FliD, preferably the at least one humoral compound and/or cellular compound interacting with FliD forms an interaction product with FliD.

EMBODIMENT 15

The method of Embodiment 14, wherein the immune response against FliD is an antibody response against FliD and wherein the antibody response against FliD forms an interaction product with FliD.

EMBODIMENT 16

The method of Embodiment 14, wherein the immune response against FliD is an anti-FliD antibody response and wherein the anti-FliD response forms an interaction product with FliD.

EMBODIMENT 17

The method of Embodiment 14, wherein the immune response against FliD comprises at least one anti-FliD antibody and wherein the anti-FliD antibody forms an interaction product with FliD.

EMBODIMENT 18

The method of any one of Embodiments 14 to 17, wherein the interaction product is detected.

EMBODIMENT 19

The method of Embodiment 18, wherein the interaction product is directly detected.

EMBODIMENT 20

The method of Embodiment 18, wherein the interaction product is indirectly detected.

EMBODIMENT 21

The method of any one of Embodiments 1 to 20, wherein the detection occurs by means of an ELISA or a line immunoassay.

EMBODIMENT 22

The method of any one of Embodiments 1 to 20, wherein the detection occurs by means of a lateral flow assay.

EMBODIMENT 23

The method of any one of Embodiments 1 to 22, wherein the sample is selected from the group comprising serum, plasma and whole blood.

EMBODIMENT 24

The method of any one of Embodiments 1 to 23, wherein the subject is a human being and *Helicobacter* infection is *H. pylori* infection.

EMBODIMENT 25

The method of Embodiment 24, wherein the FliD reacted with the sample is FliD from *H. pylori*.

EMBODIMENT 26

The method of Embodiment 25, wherein the FliD comprises an amino acid sequence according to SEQ ID NO: 1.

EMBODIMENT 27

The method of any one of Embodiments 1 to 23, wherein the subject is pig and *Helicobacter* infection is *Helicobacter suis* infection.

EMBODIMENT 28

The method of Embodiment 27, wherein the FliD reacted with the sample is FliD from *H. suis*.

EMBODIMENT 29

The method of Embodiment 28, wherein the FliD comprises an amino acid sequence according to SEQ ID NO: 3.

EMBODIMENT 30

The method of any one of Embodiments 1 to 23, wherein the subject is cat and *Helicobacter* infection is *Helicobacter felis* infection. Preferably, the cat is selected from the group comprising domestic cat, wild cat, small cat and big cat.

EMBODIMENT 31

The method of Embodiment 30, wherein the FliD reacted with the sample is FliD from *H. felis*.

EMBODIMENT 32

The method of Embodiment 31, wherein the FliD comprises an amino acid sequence according to SEQ ID NO: 5.

EMBODIMENT 33

The method of any one of Embodiments 1 to 32, wherein sensitivity of the method for detecting a *Helicobacter* infection, preferably a *H. pylori* infection in man, is more than 90% and/or 97% or less.

EMBODIMENT 34

The method of any one of Embodiments 1 to 33, wherein specificity of the method for detecting a *Helicobacter* infection, preferably a *H. pylori* infection in man, is more than 90% and/or 99% or less.

EMBODIMENT 35

Use of an immune response against FliD in a subject as a biomarker.

EMBODIMENT 36

The use of Embodiment 35, wherein the biomarker is a biomarker for infection of the subject with *Helicobacter*.

EMBODIMENT 37

The use of any one of Embodiment 35 to 36, wherein the biomarker is a biomarker for infection of the subject with *Helicobacter*, wherein the subject is man and *Helicobacter* is *H. pylori*.

EMBODIMENT 38

The use of any one of Embodiments 35 to 36, wherein the biomarker is a biomarker for infection of the subject with *Helicobacter*, wherein the subject is pig and *Helicobacter* is *H. suis*.

EMBODIMENT 39

The use of any one of Embodiments 35 to 36, wherein the biomarker is a biomarker for infection of the subject with *Helicobacter*, wherein the subject is cat and *Helicobacter* is *H. felis*.

EMBODIMENT 40

The use according to any one of Embodiments 35 to 39, wherein the biomarker is a predictive biomarker.

EMBODIMENT 41

The use according to any one of Embodiments 35 to 40, wherein the immune response is an antibody response against FliD.

EMBODIMENT 42

The use according to any one of Embodiments 35 to 41, wherein the immune response is an anti-FliD antibody response against FliD.

EMBODIMENT 43

A kit comprising FliD or a fragment thereof and at least one further constituent.

EMBODIMENT 44

The kit of Embodiment 43, wherein the at least one further constituent is selected from the group comprising a buffer, a solid phase and an instruction leaflet.

EMBODIMENT 45

The kit of any one of Embodiment 43 to 44, wherein FliD is full-length FliD.

EMBODIMENT 46

The kit according to any one of Embodiments 43 to 44, wherein FliD comprises an amino acid sequence and wherein the amino acid sequence is selected from the group comprising an amino acid sequence according to SEQ ID NO: 1, an amino acid sequence according to SEQ ID NO: 3 and an amino acid sequence according to SEQ ID NO: 5.

EMBODIMENT 47

The kit according to any one of Embodiments 43 to 46, wherein the kit is suitable for use or is for use in a method for detecting *Helicobacter* infection in a subject.

EMBODIMENT 48

The kit according to Embodiment 47, wherein the kit is suitable for use or is for use in a method of any one of Embodiments 1 to 34.

EMBODIMENT 49

A method for detecting *Helicobacter* infection and more preferably an *H. pylori* infection in a subject, wherein the method comprises detecting FliD in a sample from the subject.

EMBODIMENT 50

The method of Embodiment 49, wherein if FliD is detected in the sample from the subject, the subject is suffering from a *Helicobacter* infection, preferably an *H. pylori* infection, or the subject has undergone a *Helicobacter* infection, preferably an *H. pylori* infection, in the past.

EMBODIMENT 51

The method of any one of Embodiments 49 to 50, wherein if no FliD is detected in the sample from the subject, the subject is not suffering from a *Helicobacter* infection, preferably an *H. pylori* infection.

EMBODIMENT 52

The method of any one of Embodiments 49 to 51, wherein if no FliD is detected in the sample from the subject, the subject has undergone a *Helicobacter* infection, preferably an *H. pylori* infection in the past.

EMBODIMENT 53

The method of any one of Embodiments 49 to 52, wherein the subject is infected with *Helicobacter*, preferably *H. pylori*, expressing FliD.

EMBODIMENT 54

The method of any one of Embodiments 49 to 53, wherein the method further comprises detecting one or more antigens of *Helicobacter*, preferably of *H. pylori*.

EMBODIMENT 55

The method of Embodiment 54, wherein the one or more antigens of *Helicobacter*, preferably *H. pylori*, is selected from the group comprising CagA, VacA, GroEL, Hp 0231, JHp 0940 and HtrA.

EMBODIMENT 56

The method of any one of Embodiments 49 to 55, wherein FliD is full-length FliD or a fragment thereof.

EMBODIMENT 57

The method of any one of Embodiments 49 to 56, wherein the method comprises reacting the sample with an interacting agent, wherein the interacting agent is interacting with FliD or a fragment thereof, preferably the interacting agent is specifically interacting with FliD or a fragment thereof.

EMBODIMENT 58

The method of Embodiment 57, wherein the interacting agent is interacting with full-length FliD or a fragment of FliD.

EMBODIMENT 59

The method of any one of Embodiments 57 to 58, wherein the interacting agent is selected from the group comprising an antibody, an aptamer and a spiegelmer.

EMBODIMENT 60

The method of Embodiment 59, wherein the interacting agent is an antibody, wherein the antibody is a monoclonal antibody or a polyclonal antibody.

EMBODIMENT 61

The method of any one of Embodiments 56 to 60, wherein the interacting agent and the FliD present in the sample form an interaction product.

EMBODIMENT 62

The method of Embodiment 61, wherein the interaction product is detected.

EMBODIMENT 63

The method of Embodiment 62, wherein the interaction product is directly detected.

EMBODIMENT 64

The method of Embodiment 62, wherein the interaction product is indirectly detected.

EMBODIMENT 65

The method of any one of Embodiments 49 to 64, wherein the detection occurs by means of an ELISA or a line immunoassay.

EMBODIMENT 66

The method of any one of Embodiments 49 to 63, wherein the detection occurs by means of a lateral flow assay.

EMBODIMENT 67

The method according to any one of Embodiments 49 to 56, wherein FliD is detected by means of mass spectroscopy.

EMBODIMENT 68

The method according to Embodiment 67, wherein mass spectroscopy is selected from the group comprising LC-ESI-MS/MS, MALDI-MS, tandem MS, TOF/TOF, TOF-MS, TOF-MS/MS, triple quadrupole MS, and triple quadrupole MS/MS.

EMBODIMENT 69

The method of any one of Embodiments 49 to 68, wherein the subject is a human being and Helicobacter infection is H. pylori infection.

EMBODIMENT 70

The method of Embodiment 69, wherein the FliD is from H. pylori.

EMBODIMENT 71

The method of Embodiment 70 wherein the FliD comprises an amino acid sequence according to SEQ ID NO: 1.

EMBODIMENT 72

The method of any one of Embodiments 49 to 68, wherein the subject is pig and Helicobacter infection is Helicobacter suis infection.

EMBODIMENT 73

The method of Embodiment 72, wherein the FliD is from H. suis.

EMBODIMENT 74

The method of Embodiment 73, wherein the FliD comprises an amino acid sequence according to SEQ ID NO: 3.

EMBODIMENT 75

The method of any one of Embodiments 49 to 68, wherein the subject is cat and Helicobacter infection is Helicobacter felis infection.

EMBODIMENT 76

The method of Embodiment 75, wherein the FliD is from H. felis.

EMBODIMENT 77

The method of Embodiment 76, wherein the FliD comprises an amino acid sequence according to SEQ ID NO: 5.

EMBODIMENT 78

The method of any one of Embodiment 49 to 77, wherein the sample is selected from the group comprising stool, serum, plasma and whole blood, preferably the sample is stool.

EMBODIMENT 79

Use of FliD as a biomarker

EMBODIMENT 80

The use of Embodiment 79, wherein the biomarker is a biomarker for infection of a subject with Helicobacter.

EMBODIMENT 81

The use of any one of Embodiments 79 to 80, wherein the biomarker is a biomarker for infection of the subject with Helicobacter, wherein the subject is man and Helicobacter is H. pylori.

EMBODIMENT 82

The use of Embodiment 81, wherein FliD comprises an amino acid sequence according to SEQ ID NO: 1.

EMBODIMENT 83

The use of any one of Embodiments 80 to 81, wherein the biomarker is a biomarker for infection of the subject with Helicobacter, wherein the subject is pig and Helicobacter is H. suis.

EMBODIMENT 84

The use of Embodiment 83, wherein FliD comprises an amino acid sequence according to SEQ ID NO: 3.

EMBODIMENT 85

The use of any one of Embodiments 80 to 81, wherein the biomarker is a biomarker for infection of the subject with Helicobacter, wherein the subject is cat and Helicobacter is H. felis.

EMBODIMENT 86

The use of Embodiment 85, wherein FliD comprises an amino acid sequence according to SEQ ID NO: 5.

EMBODIMENT 87

The use according to any one of Embodiment 79 to 86, wherein the biomarker is a predictive biomarker.

EMBODIMENT 88

A kit comprising an interacting agent capable of interacting with FliD or a fragment thereof and at least one further constituent.

EMBODIMENT 89

The kit of Embodiment 88, wherein the at least one further constituent is selected from the group comprising a buffer, a solid phase and an instruction leaflet.

EMBODIMENT 90

The kit of Embodiment 89, wherein the interacting agent is capable of specifically interacting with FliD or a fragment thereof.

EMBODIMENT 91

The kit of any one of Embodiments 88 to 90, wherein the interacting agent is selected from the group comprising an antibody, an aptamer and a spiegelmer.

EMBODIMENT 92

The kit according to any one of Embodiments 88 to 91, wherein the kit is suitable for use or is for use in a method for detecting *Helicobacter* infection in a subject.

EMBODIMENT 93

The kit according to Embodiment 92, wherein the kit is suitable for use or is for use in a method of any one of Embodiments 49 to 78.

EMBODIMENT 94

A method for detecting *Helicobacter* infection and more preferably an *H. pylori* infection in a subject, wherein the method comprises detecting in a sample from the subject a nucleic acid coding for FliD.

EMBODIMENT 95

The method of Embodiment 94, wherein the nucleic acid is a genomic nucleic acid coding for FliD, preferably DNA

EMBODIMENT 96

The method of Embodiment 94, wherein the nucleic acid is an mRNA coding for FliD.

EMBODIMENT 97

The method of any one of Embodiments 94 to 96, wherein if a nucleic acid coding for FliD is detected in the sample from the subject, the subject is suffering from a *Helicobacter* infection, preferably an *H. pylori* infection, or the subject has undergone a *Helicobacter* infection, preferably an *H. pylori* infection, in the past.

EMBODIMENT 98

The method of any one of Embodiment 94 to 97, wherein if no nucleic acid coding for FliD is detected in the sample from the subject, the subject is not suffering from a *Helicobacter* infection, preferably an *H. pylori* infection.

EMBODIMENT 99

The method of any one of Embodiments 94 to 98, wherein if no nucleic acid coding for FliD is detected in the sample from the subject, the subject has undergone a *Helicobacter* infection, preferably an *H. pylori* infection in the past.

EMBODIMENT 100

The method of any one of Embodiments 94 to 99, wherein the subject is infected with *Helicobacter*, preferably *H. pylori*, expressing FliD.

EMBODIMENT 101

The method of any one of Embodiment 94 to 100, wherein the method further comprises detecting one or more antigens of *Helicobacter*, preferably of *H. pylori*, and/or a nucleic acid coding for one or more antigens of *Helicobacter*, preferably of *H. pylori*.

EMBODIMENT 102

The method of Embodiment 101, wherein the one or more antigens of *Helicobacter*, preferably *H. pylori*, is selected from the group comprising CagA, VacA, GroEL, Hp 0231, JHp 0940 and HtrA.

EMBODIMENT 103

The method of any one of Embodiments 94 to 102, wherein FliD is full-length FliD or a fragment thereof.

EMBODIMENT 104

The method of any one of Embodiments 94 to 103, wherein the method comprises reacting the sample with an interacting agent, wherein the interacting agent is interacting with a nucleic acid coding for FliD, preferably the interacting agent is specifically interacting with a nucleic acid coding for FliD.

EMBODIMENT 105

The method of Embodiment 104, wherein the interacting agent is interacting with a nucleic acid coding for full-length FliD or a fragment of FliD.

EMBODIMENT 106

The method of any one of Embodiments 104 to 105, wherein the interacting agent is selected from the group comprising a primer and a probe.

EMBODIMENT 107

The method of any one of Embodiments 104 to 106, wherein the interacting agent and the nucleic acid coding for FliD present in the sample form an interaction product.

EMBODIMENT 108

The method of Embodiment 107, wherein the interaction product is detected.

EMBODIMENT 109

The method of Embodiment 108, wherein the interaction product is directly detected.

EMBODIMENT 110

The method of Embodiment 108, wherein the interaction product is indirectly detected.

EMBODIMENT 111

The method according to any one of Embodiments 94 to 103, wherein a nucleic acid molecule coding for FliD is detected by means of mass spectroscopy, PCR or a hybridization assay.

EMBODIMENT 112

The method according to Embodiment 111, wherein mass spectroscopy is selected from the group comprising LC-ESI- MS/MS, MALDI-MS, tandem MS, TOF/TOF, TOF-MS, TOF-MS/MS, triple quadrupole MS, and triple quadrupole MS/MS.

EMBODIMENT 113

The method of any one of Embodiments 94 to 112, wherein the subject is a human being and *Helicobacter* infection is *H. pylori* infection.

EMBODIMENT 114

The method of Embodiment 113, wherein the nucleic acid coding for FliD is from *H. pylori*.

EMBODIMENT 115

The method of Embodiment 114, wherein the nucleic acid coding for FliD comprises a nucleotide sequence according to SEQ ID NO: 2.

EMBODIMENT 116

The method of any one of Embodiments 94 to 112, wherein the subject is pig and *Helicobacter* infection is *Helicobacter suis* infection.

EMBODIMENT 117

The method of Embodiment 116, wherein the nucleic acid coding for FliD is from *H. suis*.

EMBODIMENT 118

The method of Embodiment 117, wherein the nucleic acid coding for FliD comprises a nucleotide sequence according to SEQ ID NO: 4.

EMBODIMENT 119

The method of any one of Embodiments 94 to 112, wherein the subject is cat and *Helicobacter* infection is *Helicobacter felis* infection.

EMBODIMENT 120

The method of Embodiment 119, wherein the nucleic acid coding for FliD is from *H. felis*.

EMBODIMENT 121

The method of Embodiment 120, wherein the FliD comprises an amino acid sequence according to SEQ ID NO: 6.

EMBODIMENT 122

The method of any one of Embodiments 94 to 121, wherein the sample is selected from the group comprising stool, serum, plasma and whole blood, preferably the sample is stool.

EMBODIMENT 123

Use of a nucleic acid coding for FliD as a biomarker.

EMBODIMENT 124

The use of Embodiment 123, wherein the biomarker is a biomarker for infection of a subject with *Helicobacter*.

EMBODIMENT 125

The use of any one of Embodiments 123 to 124, wherein the biomarker is a biomarker for infection of the subject with *Helicobacter*, wherein the subject is man and *Helicobacter* is *H. pylori*.

EMBODIMENT 126

The use of Embodiment 125, wherein the nucleic acid coding for FliD comprises a nucleotide sequence according to SEQ ID NO: 2.

EMBODIMENT 127

The use of any one of Embodiments 124 to 125, wherein the biomarker is a biomarker for infection of the subject with *Helicobacter*, wherein the subject is pig and *Helicobacter* is *H. suis*.

EMBODIMENT 128

The use of Embodiment 127, wherein the nucleic acid coding for FliD comprises a nucleotide sequence according to SEQ ID NO: 4.

EMBODIMENT 129

The use of any one of Embodiments 124 to 125, wherein the biomarker is a biomarker for infection of the subject with *Helicobacter*, wherein the subject is cat and *Helicobacter* is *H. felis*.

EMBODIMENT 130

The use of Embodiment 129, wherein the nucleic acid coding for FliD comprises a nucleotide sequence according to SEQ ID NO: 6.

EMBODIMENT 131

The use according to any one of Embodiments 123 to 130, wherein the biomarker is a predictive biomarker.

EMBODIMENT 132

A kit comprising an interacting agent capable of interacting with a nucleic acid coding for FliD or a fragment thereof and at least one further constituent.

EMBODIMENT 133

The kit of Embodiment 132, wherein the at least one further constituent is selected from the group comprising a buffer, a solid phase and an instruction leaflet.

EMBODIMENT 134

The kit of Embodiment 133, wherein the interacting agent is capable of specifically interacting with FliD or a fragment thereof.

EMBODIMENT 135

The kit of any one of Embodiments 132 to 134, wherein the interacting agent is selected from the group comprising a primer and a probe.

EMBODIMENT 136

The kit according to any one of Embodiments 132 to 135, wherein the kit is suitable for use or is for use in a method for detecting *Helicobacter* infection in a subject.

EMBODIMENT 137

The kit according to Embodiment 136, wherein the kit is suitable for use or is for use in a method of any one of Embodiments 94 to 122.

The present inventors have surprisingly found that FliD which is a protein also referred to as "hook-associated protein 2 homologue", is a marker for infection with *Helicobacter* and *H. pylori* in particular. The present inventors have also surprisingly found that FliD and/or an immune response against FliD can be advantageously used as a marker in serological analysis and, accordingly, in any method and assay, respectively, which is based on or makes use of a sample of a subject to be tested for *Helicobacter* and *H. pylori* infection in particular, whereby the sample is preferably selected from the group comprising a serum sample, a plasma sample, a blood sample and a stool sample. Finally, the present inventors have surprisingly found that infection of a subject with *Helicobacter* and *H. pylori* in particular can be detected based on FliD and/or a nucleic acid coding for FliD, whereby FliD and/or the nucleic acid coding for FliD are used as the sole marker. In other words, according to the present invention, an infection of a subject with *Helicobacter* and *H. pylori* in particular can be diagnosed solely based and, respectively, relying on FliD and/or a nucleic acid coding therefor. The same is also true for an immune response against FliD developed by a subject infected with *Helicobacter* and *H. pylori* in particular: According to the present invention, an infection of a subject with *Helicobacter* and *H. pylori* in particular can be diagnosed solely based and, respectively, relying on an immune response against FliD, whereby the immune response against FliD was generated by the subject. A further advantage of the present invention is that the immune response against FliD and FliD as such can be determined in a sample which is typically obtained by non-invasive methods which is in contrast to many detection methods of the prior art where the sample has to be taken by an invasive method such as a biopsy.

It will be acknowledged by a person skilled in the art that the present invention can in principle be applied to the detection of any infection of a subject with *Helicobacter* as long as such *Helicobacter* codes for and/or expresses FliD. It will also be acknowledged by a person skilled in the art that, typically, a distinct species of a subject such as, e.g., man, will be infected by a distinct species of *Helicobacter*. In case the subject is man, the species of *Helicobacter* is *H. pylori*. In case the subject is pig, the species of *Helicobacter* is *H. suis*. In case the subject is cat, including big cats, the species of *Helicobacter* is *H. felis*. The instant specification particularly refers to the detection of *H. pylori* in man. Such reference to *H. pylori* and man, however, is made solely for reasons of clarity and given the above, any embodiment referring to *H. pylori* and man, equally applies to any other *Helicobacter* expressing FliD, or a homologue thereof, and any other species of the subject. Preferably, the other species of the subject is any mammal which suffers or may suffer from an infection with *Helicobacter* and a species homolog to *H. pylori*, whereby such *Helicobacter* and species homolog to *H. pylori* expresses FliD or a homologue thereof.

It will also be acknowledged by a person skilled in the art that for each species of *Helicobacter* typically various strains exist. The amino acid sequence and the nucleic acid sequence of FliD of such strains of the *Helicobacter* species typically show a very high identity in terms of amino acid sequence. More specifically, bioinformatic analysis revealed that FliD amino acid sequence is present and highly conserved in all (>200) *H. pylori* strains.

FliD has a homology of 97% in around 200 *H. pylori* strains which were analyzed by the present inventors. Interestingly, except for some other non-*pylori* *Helicobacter* species with partial homology, there is no other known organism with a significant genomic or proteomic homology to FliD of *H. pylori*. Comparison of the *H. pylori* FliD protein shows the high conservation of FliD in *Helicobacter* species, while it is distinct from most other bacteria as well as eukaryotic organisms. This analysis together with high antigenicity prediction of this protein provides the rational for factually no cross-reactivity.

Furthermore, FliD is expressed by factually all strains which infect or which are capable of infecting a subject. This explains why according to the present invention FliD is a marker for factually each strain of *H. pylori* and, respectively, each strain of the *Helicobacter* species infecting the respective subject species. In other words, nearly all *H. pylori* positive patients show an immune response against FliD.

The *H. pylori* FliD protein is an essential element in the assembly of the functional flagella and a FliD mutant strain is completely non-motile. Flagellin plays a central role in bacterial motility and is necessary for colonization and persistence of *H. pylori* infection (Eaton, et al., 1996). Motility of *H. pylori* is a virulent factor in the pathogenesis of gastric mucosal injury (S. Watanabe, et al., 1997). The *H. pylori* FliD gene encodes a 76-kDa protein (Kim, et al., 1999). The FliD operon of *H. pylori* consists of FlaG, FliD, and FliS genes, in the order stated, under the control of a Sigma (28)-dependent promoter. An entry for FliD from *H. pylori* can be found in databanks UniProtKB/Swiss-Prot as P96786.4 providing, among others, the amino acid sequence thereof and mutations of FliD as found in various strains of *H. pylori*.

The method of the invention for detecting *Helicobacter* infection in a subject, preferably an *H. pylori* infection in a subject, can also be characterized such that it comprises the step of determining whether a sample from the subject contains an immune response against FliD, FliD or a nucleic acid coding for FliD. If the sample from the subject matter contains an antibody response against FliD, FliD or a nucleic acid coding for FliD, the subject is suffering from *Helicobacter* infection, preferably an *H. pylori* infection, or has undergone a *Helicobacter* infection in the past, preferably an *H. pylori* infection in the past.

The methods of the invention for detecting *Helicobacter* infection in a subject, preferably an *H. pylori* infection in a subject, can also be applied to a subject of which it is unknown whether it is suffering from a *Helicobacter* infection, preferably *H. pylori* infection, or whether such subject has undergone a *Helicobacter* infection, preferably *H. pylori* infection. Insofar, the present invention is related in a further aspect to methods for determining whether a subject is suffering from a *Helicobacter* infection, preferably *H. pylori* infection, or has undergone a *Helicobacter* infection, preferably *H. pylori* infection in the past.

As preferably used herein, the expression "in the past" refers to a point in time which is prior to the point in time when a sample has been or is taken from a subject, whereby such sample is a sample used in connection with the various aspects and/or the various embodiments of the present invention and in particular in detecting *H. pylori* and/or *H. pylori* infection in a subject and in the diagnosis of *H. pylori* and/or *H. pylori* infection in a subject.

In connection with the various aspects of the present invention and the various methods of the invention in particular, it will be acknowledged by a person skilled in the art that the immune response and the anti-FliD antibody response generated by the subject infected by *Helicobacter* and *H. pylori* in particular persists over some years. The prevalence of such anti-FliD antibody response is typically about 50% after 1 to 5 years after eradication of *H. pylori*, about 50% after 6 to 10 years after eradication of *H. pylori*, about 25% after 11 to 15 years after eradication of *H. pylori* and about 25% after 16 to 20 years after eradication of *H. pylori*. In light thereof, a subject which is diagnosed as *H. pylori* positive may be a subject which is actually suffering from *H. pylori* infection at the time the sample was taken, or a subject which had undergone an *H. pylori* infection in the past with the anti-FliD immune response still prevailing.

To the extent that immune response against FliD is an antibody response against FliD and more specifically an anti-FliD antibody response, the anti-FliD antibodies are typically IgG or IgA. This class specificity can be used in detection the anti-FliD antibodies by using, as the detecting antibodies or capture antibodies, anti-IgG and/or anti-IgA antibodies. In the embodiment where the subject is man, the detecting antibodies and capture antibodies are preferably anti-human IgG and/or anti-human IgA.

In connection with the various aspects of the present invention and the various methods of the invention in particular, the methods may, in an embodiment, additionally comprise the detection of one or more *Helicobacter* antigens or a nucleic acid coding for such *Helicobacter* antigens. In an embodiment, such *Helicobacter* antigens are *H. pylori* antigens. In a further embodiment, the antigens are selected from the group comprising CagA, VacA, GroEL, Hp 0231, JHp 0940 and HtrA which are all known in the art, and described, for example, in Yakoob J et al. (Yakoob J et al., Gut and Liver, Vol. 4, No. 3, September 2010, pp. 345-350), Sabarth N et al. (Sabarth N et al., Infection and Immunity, November 2002, p. 6499-6503), Gao L. et al. (Gao L. et al., Cancer Res 2009; 69: (15). Aug. 1, 2009, p. 6164-6170), Yamaoka Y (Yamaoka Y, J Med Microbiol. 2008 May; 57 (Pt5): 545-553), Miehlke S et al. (Miehlke S et al., Int. J. Cancer: 87, 322-327 (2000)), and Atherton J C et al. (Atherton J C et al., Current Microbiology, Vol. 39(1999), pp 211-218). An amino acid sequence of CagA is disclosed herein as SEQ ID NO: 7, a nucleotide sequence of CagA is disclosed herein as SEQ ID NO:8, an amino acid sequence of VacA is disclosed herein as SEQ ID NO: 9, a nucleotide sequence of VacA is disclosed herein as SEQ ID NO:10, an amino acid sequence of GroEL is disclosed herein as SEQ ID NO: 11, a nucleotide sequence of GroEL is disclosed herein as SEQ ID NO:12, an amino acid sequence of Hp0231 is disclosed herein as SEQ ID NO:13, a nucleotide sequence of Hp0231 is disclosed herein as SEQ ID NO:14, an amino acid sequence of JHp0940 is disclosed herein as SEQ ID NO:15, a nucleotide sequence of JHp0940 is disclosed herein as SEQ ID NO:16, an amino acid sequence of HtrA is disclosed herein as SEQ ID NO:17, and a nucleotide sequence of HtrA is disclosed herein as SEQ ID NO:18.

In an embodiment of the method of the invention where *Helicobacter* infection and more preferably an *H. pylori* infection in a subject is detected by detecting in a sample from the subject an immune response against FliD and in particular an anti-FliD antibody in the sample, the sample and FliD are reacted. In one embodiment, the sample is added to FliD. Preferably, FliD is attached to a solid phase in such method. It is also within the present invention that FliD is added to the sample. Preferably, FliD is added as a solution, more preferably as an aqueous solution such as a buffered solution. In a preferred embodiment, FliD is reacted with the sample with FliD being attached to a solid phase. It will be acknowledged by a person skilled in the art that FliD and the sample are reacted under conditions such that, if the sample contains an immune response against FliD and anti-FliD antibodies in particular, an interaction product is formed. Preferably, such interaction product is a complex of FliD and an anti-FliD antibody contained in the sample.

The interaction product thus formed can be either directly or indirectly detected. In the embodiment where the interaction product is detected directly, the FliD reacted with the sample comprises a label which allows the detection of FliD, particularly when interacting with an anti-FliD antibody. Labels of this type are known to the ones skilled in the art and encompass radiolabels, fluorescence labels, dyes, nanoparticles as Gold and enzymes such as horseradish peroxidase. Further labels are those disclosed herein in connection with the labeling of antibodies. In the embodiment where the interaction product is detected indirectly, the interaction product is subsequently reacted with a detection agent, whereby the detection agent specifically binds to the interaction product. Such detection agent may be an antibody, preferably an anti-IgG or an anti-IgA antibody. The detection agent itself is typically comprising a label which allows the detection of the detection agent, preferably when the detection agent is specifically bound to the interaction product.

In preferred embodiments of the methods of the invention the interaction product is detected by means of an enzyme-linked immunosorbent assay (ELISA) or a radioimmunoassay which are known to a person skilled in the art (Lottspeich F. and Zorbas H (eds.), Bioanalytik, Spektrum Akademischer Verlag Heidelberg, 1998). The ELISA may be an indirect ELISA, a sandwich ELISA, a competitive ELISA or a non-competitive ELISA.

In an alternative preferred embodiments of the methods of the invention the interaction product is detected by means of a lateral flow test which is also known as lateral flow immunochromatographic assays which are, for example, described in U.S. Pat. No. 6,485,982. Such lateral flow test is, in an embodiment, used in any method of the invention where either an anti-FliD antibody is and, respectively, anti-FliD antibodies are detected in a sample from a subject. The lateral flow test will be described for illustrative purposes for the embodiment of the method of the invention where anti-FliD antibodies in a sample from a subject are detected, wherein the subject is man.

The technology is based on a series of capillary beds, such as pieces of porous paper or polymer. Each of these components has the capability to transport fluid, e.g. serum, plasma or blood, precipitately. The sample pad acts as a sponge and holds an excess of sample fluid. When the sample pad is saturated, the fluid moves to the conjugate pad in which nanoparticles, preferably gold nanoparticles, conjugated with anti-human antibody is located. When the sample fluid migrate to this element, it dissolves the particles and in one combined reaction, the sample and conjugate mix flow through the porous structure. In this way, antibody immobilized on the surface of nanoparticles, binds to human IgG existing in the sample while migrating further through the next capillary matrix. On this element which is typically a hydrophobic membrane like nitrocellulose antigens as well as a control (e.g. human IgG) are immobilized as test or control lines. Once human IgG which is now bound to the conjugate particles reaches these lines, antigen immobilized on the membrane will capture antibody complex specifically. After a while, more and more particles accumulate at an antigen site and a simply detectable colored band appears. In one embodiment there is only one antigen, namely FliD. In another embodiment there are, in addition to FliD, one or more antigens. Preferably, the one or more antigens is/are selected from the group comprising CagA, VacA, GroEL, Hp 0231, JHp 0940 and HtrA.

In a further alternative preferred embodiments of the methods of the invention the interaction product is detected by means of a line assay. Such line assay typically comprises a plurality of strips. On said strips, highly purified recombinant either FliD or an interactin agent which is capable of interacting with FliD is fixed on the strips. Such strips are preferably made of nitrocellulose membrane. The strips are incubated with the sample, preferably with a diluted serum or plasma sample, and the anti-FliD antibodies bind to FliD, in case FliD is immobilized for detecting anti-FliD antibodies in the sample, or FliD binds to the anti-FliD antibodies, in case anti-FliD antibodies are immobilized for detecting FliD in the sample, on the test strips. In a second step, the strips are incubated with anti-human immunoglobulin antibodies (IgG and IgA), which are coupled to horse radish peroxidase. Specifically bound antibodies are detected with a staining reaction catalyzed by the peroxidase. If an antigen-antibody reaction has taken place forming an interaction product, a dark band will appear on the strip at the corresponding point. In an embodiment control bands at the upper end of the test strips are:
a) The reaction control band under the strip number, which must show a reaction for every sample.
b) The conjugate control bands (IgG, IgA) are used to check the detected antibody class. If, for example, the test strip for the detection of IgG antibodies is used, the IgG conjugate will show a clear band.
c) "Cut-off control": The intensity of this band allows the assessment of the reactivity of the individual antigen bands.

An assay having this kind of design, with antigens different from FliD, is basically available from Mikrogen GmbH, Neuried, Germany, as "recomLine *Helicobacter* IgG" or "recomLine *Helicobacter* IgA" (Ref: http://www-.mikrogen.de/uploads/tx_oemikrogentables/dokumente/GARLHP001EN.pdf).

In an embodiment of the method of the invention for detecting *Helicobacter* infection and more preferably an *H. pylori* infection in a subject, wherein the method comprises detecting in a sample from the subject FliD, FliD is detected by means of mass spectrometry which is, e.g., described in Lottspeich F. and Zorbas H (eds.), Bioanalytik, Spektrum Akademischer Verlag Heidelberg, 1998.

In those embodiments of the methods of the invention where FliD is detected in a sample from the subject, the interacting agent forming together with FliD the interaction product is preferably one selected from the group comprising an antibody, an aptamer and a spiegelmer. The generation of such interacting agent is within the skills of a person of the art.

The generation of an antibody binding and more particularly specifically binding to FliD, is known to the one skilled in the art and, for example, described in Harlow, E., and Lane, D., "Antibodies: A Laboratory Manual," Cold Spring Harbor Laboratory, Cold Spring Harbor, N.Y., (1988). Preferably, monoclonal antibodies may be used in connection with the present invention which may be manufactured according to the protocol of Cesar and Milstein and further developments based thereon. Antibodies as used herein, include, but are not limited to, complete antibodies, antibody fragments or derivatives such as Fab fragments, Fc fragments and single-stranded antibodies, as long as they are suitable and capable of binding to FliD. Apart from monoclonal antibodies also polyclonal antibodies may be used and/or generated. The generation of polyclonal antibodies is also known to the one skilled in the art and, for example, described in Harlow, E., and Lane, D., "Antibodies: A Laboratory Manual," Cold Spring Harbor Laboratory, Cold Spring Harbor, N.Y., (1988).

The antibodies which may be used according to the present invention may have one or several markers or labels. Such markers or labels may be useful for detecting the antibody. Preferably the markers and labels are selected from the group comprising avidine, streptavidine, biotin, gold, enzymes as HRP and fluorescein and used, e. g., in ELISA methods. These and further markers as well as methods are, e. g. described in Harlow, E., and Lane, D., "Antibodies: A Laboratory Manual," Cold Spring Harbor Laboratory, Cold Spring Harbor, N.Y., (1988).

Aptamers are D-nucleic acids which are either single stranded or double stranded and which specifically interact with a target molecule such as, in the instant invention, FliD. The manufacture or selection of aptamers is, e. g., described in European patent EP 0 533 838. Basically the following steps are realized. First, a mixture of nucleic acids, i. e. potential aptamers, is provided whereby each nucleic acid typically comprises a segment of several, preferably at least eight subsequent randomised nucleotides. This mixture is subsequently contacted with the target molecule whereby the nucleic acid(s) bind to the target molecule, such as based on an increased affinity towards the target or with a bigger force thereto, compared to the candidate mixture. The binding nucleic acid(s) are/is subsequently separated from the remainder of the mixture. Optionally, the thus obtained nucleic acid(s) is amplified using, e. g., polymerase chain reaction. These steps may be repeated several times giving at the end a mixture having an increased ratio of nucleic acids specifically binding to the target from which the final binding nucleic acid is then optionally selected. These specifically binding nucleic acid(s) are referred to as aptamers. It is obvious that at any stage of the method for the generation or identification of the aptamers samples of the mixture of individual nucleic acids may be taken to determine the sequence thereof using standard techniques. It is within the present invention that the aptamers may be stabilized such as, e. g., by introducing defined chemical groups which are known to the one skilled in the art of generating aptamers. Such modification may for example reside in the introduction of an amino group at the 2'-position of the sugar moiety of the nucleotides.

The generation or manufacture of spiegelmers binding to and more particularly specifically binding to FliD as a target molecule is based on a similar principle. The manufacture of spiegelmers is described in international patent application WO 98/08856. Spiegelmers are L-nucleic acids, which means that they are composed of L-nucleotides rather than D-nucleotides as aptamers are. Spiegelmers are characterized by the fact that they have a very high stability in biological system and, comparable to aptamers, specifically interact with the target molecule against which they are directed. In the purpose of generating spiegelmers, a heterogonous population of D-nucleic acids is created and this population is contacted with the optical antipode of the target molecule, in the present case for example with the D-enantiomer of the naturally occurring L-enantiomer of FliD. Subsequently, those D-nucleic acids are separated which do not interact with the optical antipode of the target molecule. However, those D-nucleic acids interacting with the optical antipode of the target molecule are separated, optionally determined and/or sequenced and subsequently the corresponding L-nucleic acids are synthesized based on the nucleic acid sequence information obtained from the D-nucleic acids. These L-nucleic acids which are identical in terms of sequence with the aforementioned D-nucleic acids interacting with the optical antipode of the target molecule, will specifically interact with the naturally occurring target molecule rather than with the optical antipode thereof. Similar to the method for the generation of aptamers it is also possible to repeat the various steps several times and thus to enrich those nucleic acids specifically interacting with the optical antipode of the target molecule.

In the embodiments of the method of the invention for detecting *Helicobacter* infection and more preferably an *H. pylori* infection in a subject, wherein the method comprises detecting in a sample from the subject a nucleic acid coding for FliD, the interacting agent is selected from the group comprising a primer and a probe. Given the nucleotide and amino acid sequences of FliD disclosed herein, it is within the skills of a person of the art to design and prepare such primer and probe (see, for example, Lottspeich F. and Zorbas H (eds.), Bioanalytik, Spektrum Akademischer Verlag Heidelberg, 1998). Such interacting agent can be labeled. The various labels and ways how to label the interacting agent are known to a person skilled in the art. In an embodiment the labels are the same as outlined above in connection with the antibodies.

The interaction product comprising a nucleic acid molecule coding for FliD or a fragment thereof and an interaction agent can be detected by means known to a person skilled in the art and, for example, described in Lottspeich F. and Zorbas H (eds.), Bioanalytik, Spektrum Akademischer Verlag Heidelberg, 1998.

In an embodiment of the method of the invention for detecting *Helicobacter* infection and more preferably an *H. pylori* infection in a subject, wherein the method comprises detecting in a sample from the subject a nucleic acid coding for FliD, the nucleic acid coding for FliD is detected by means of mass spectrometry which is, e.g. described in Lottspeich F. and Zorbas H (eds.), Bioanalytik, Spektrum Akademischer Verlag Heidelberg, 1998.

In an embodiment of the method of the invention for detecting *Helicobacter* infection and more preferably an *H. pylori* infection in a subject, wherein the method comprises detecting in a sample from the subject a nucleic acid coding for FliD, the nucleic acid coding for FliD is detected by means of polymerase chain reaction (PCR) in its diverse forms which are, e.g., described in Lottspeich F. and Zorbas H (eds.), Bioanalytik, Spektrum Akademischer Verlag Heidelberg, 1998. Alternatively, the nucleic acid coding for FliD is detected by a hybridization assay as, e.g., described in Lottspeich F. and Zorbas H (eds.), Bioanalytik, Spektrum Akademischer Verlag Heidelberg, 1998.

In those aspects of the invention which are related to biomarker, it will be acknowledged that the immune response against FliD as defined herein, FliD and a nucleic acid coding for FliD each act as a predictive biomarker as the presence of said immune response against FliD as defined herein, FliD and/or nucleic acid coding for FliD is correlated with histology and inflammation in untreated patients.

It will be acknowledged by a person skilled in the art that given the disclosure provided herein the particular design of the kit of the invention is within the common skills of a person skilled in the art. In an embodiment, the kit is a ready-for-use kit.

In a further aspect of the present invention, the present invention is related to the use of the interacting agents as disclosed herein for the detection of FliD as disclosed herein.

As preferably used herein a sample is a sample as immediately obtained from a or the subject, or a sample which has been processed prior to being used in connection with the invention and in particular with the methods of the invention.

In an embodiment of the various aspects and embodiments of the invention the subject is a subject which is assumed to suffer from or suspected of suffering from a *H. pylori* infection.

In an embodiment *Helicobacter* infection is infection with *Helicobacter* or an assumed or suspected infection with *Helicobacter*.

In an embodiment of any aspect of the present invention where a first compound specifically interacts with or specifically binds to a second compound, the interaction or binding between said first compound and said second compound is characterized by a $K_D$ of 1 µM or less, preferably a $K_D$ of 0.25 µM or less and more preferably a $K_D$ of 0.1 or less.

It will be understood by a person skilled in the art that in those embodiment where FliD is detected, FliD may be present either as a full-length FliD or a fragment of FliD or a fragment of full-length FliD. As preferably used herein a full-length FliD is a FliD as produced by *Helicobacter* which is active as a virulence factor. In an embodiment a full-length FliD is preferably a FliD as produced by *Helicobacter*. A fragment of full-length FliD is a fragment the amino acid sequence of which is shorter than the amino acid sequence of full-length FliD, whereby the fragment of FliD is still active as a virulence factor. A fragment of FliD is preferably a fragment of FliD, preferably of full-length FliD, whereby the fragment has an amino acid sequence which is long enough so as to allow a person skilled in the art to identify the fragment to be a fragment of FliD and full-length FliD in particular and to exclude that the fragment is a fragment of a protein or polypeptide different from FliD and full-length FliD in particular. In a preferred embodiment full-length FliD comprises an amino acid sequence according to SEQ ID NO:1.

The same considerations and definitions equally apply to a nucleic acid coding for FliD. In accordance therewith, it will be understood by a person skilled in the art that in those embodiment where a nucleic acid coding for FliD is detected, a nucleic acid coding for FliD may be present either as a nucleic acid coding for a full-length FliD or a nucleic acid coding for fragment of FliD or a nucleic acid coding for fragment of full-length FliD. As preferably used herein a full-length FliD is a FliD as produced by *Helico-*

*bacter* which is active as a virulence factor. In an embodiment a full-length FliD is preferably a FliD as produced by *Helicobacter*. A fragment of full-length FliD is a fragment the amino acid sequence of which is shorter than the amino acid sequence of full-length FliD, whereby the fragment of FliD is still active as a virulence factor. A fragment of FliD is preferably a fragment of FliD, preferably of full-length FliD, whereby the fragment has an amino acid sequence which is long enough so as to allow a person skilled in the art to identify the fragment to be a fragment of FliD and full-length FliD in particular and to exclude that the fragment is a fragment of a protein or polypeptide different from FliD and full-length FliD in particular. In a preferred embodiment the nucleic acid coding for a full-length FliD comprises a nucleotide sequence according to SEQ ID NO:2.

A fragment of a nucleic acid coding for FliD is preferably a fragment of a nucleic acid coding for FliD, preferably for full-length FliD, whereby the fragment of the nucleic acid has a nucleotide sequence which is long enough so as to allow a person skilled in the art to identify the fragment to be a fragment of a nucleic acid coding for FliD and full-length FliD in particular and to exclude that the fragment of the nucleic acid is a fragment of a nucleic acid coding for a protein or polypeptide different from FliD and full-length FliD in particular.

It will also be understood by a person skilled in the art that in those embodiments of the methods of the invention where an immune response against FliD as defined herein is detected, FliD which is reacted with the immune response against FliD as defined herein, can be FliD as produced by the *Helicobacter* species infecting the subject or presumably infecting the subject, can be a full-length FliD as defined herein or can be a fragment of FliD as defined herein. Furthermore, a fragment of FliD is, in an embodiment, a fragment of FliD having a shorter amino acid sequence than FliD, wherein the fragment can be used in said embodiments of the methods of the invention, while allowing specific interaction with or specific detection of the immune response against FliD as defined herein.

In connection with the instant invention a primer targeting a nucleic acid coding for FliD as used in connection with the various aspects of the invention and/or in connection with the various embodiments of the present invention is one selected from the group comprising a primer comprising a nucleotide sequence according to SEQ ID NO: 21, a primer comprising a nucleotide sequence according to SEQ ID NO: 22, a primer comprising a nucleotide sequence according to SEQ ID NO: 23, a primer comprising a nucleotide sequence according to SEQ ID NO: 24, a primer comprising a nucleotide sequence according to SEQ ID NO: 25, a primer comprising a nucleotide sequence according to SEQ ID NO: 26, a primer comprising a nucleotide sequence according to SEQ ID NO: 27 and a primer comprising a nucleotide sequence according to SEQ ID NO: 28. Preferably, the primer is a combination at least two primers, whereby a first primer of the at least two primers is a primer comprising a nucleotide sequence according to SEQ ID NO: 21 and a second primer of the at least two primers is a primer comprising a nucleotide sequence according to SEQ ID NO: 22;

a first primer of the at least two primers is a primer comprising a nucleotide sequence according to SEQ ID NO: 21 and a second primer of the at least two primers is a primer comprising a nucleotide sequence according to SEQ ID NO: 24;

a first primer of the at least two primers is a primer comprising a nucleotide sequence according to SEQ ID NO: 21 and a second primer of the at least two primers is a primer comprising a nucleotide sequence according to SEQ ID NO: 26;

a first primer of the at least two primers is a primer comprising a nucleotide sequence according to SEQ ID NO: 21 and a second primer of the at least two primers is a primer comprising a nucleotide sequence according to SEQ ID NO: 28;

a first primer of the at least two primers is a primer comprising a nucleotide sequence according to SEQ ID NO: 23 and a second primer of the at least two primers is a primer comprising a nucleotide sequence according to SEQ ID NO: 22;

a first primer of the at least two primers is a primer comprising a nucleotide sequence according to SEQ ID NO: 23 and a second primer of the at least two primers is a primer comprising a nucleotide sequence according to SEQ ID NO: 24;

a first primer of the at least two primers is a primer comprising a nucleotide sequence according to SEQ ID NO: 23 and a second primer of the at least two primers is a primer comprising a nucleotide sequence according to SEQ ID NO: 26;

a first primer of the at least two primers is a primer comprising a nucleotide sequence according to SEQ ID NO: 23 and a second primer of the at least two primers is a primer comprising a nucleotide sequence according to SEQ ID NO: 28;

a first primer of the at least two primers is a primer comprising a nucleotide sequence according to SEQ ID NO: 25 and a second primer of the at least two primers is a primer comprising a nucleotide sequence according to SEQ ID NO: 22;

a first primer of the at least two primers is a primer comprising a nucleotide sequence according to SEQ ID NO: 25 and a second primer of the at least two primers is a primer comprising a nucleotide sequence according to SEQ ID NO: 24;

a first primer of the at least two primers is a primer comprising a nucleotide sequence according to SEQ ID NO: 25 and a second primer of the at least two primers is a primer comprising a nucleotide sequence according to SEQ ID NO: 26;

a first primer of the at least two primers is a primer comprising a nucleotide sequence according to SEQ ID NO: 25 and a second primer of the at least two primers is a primer comprising a nucleotide sequence according to SEQ ID NO: 28;

a first primer of the at least two primers is a primer comprising a nucleotide sequence according to SEQ ID NO: 27 and a second primer of the at least two primers is a primer comprising a nucleotide sequence according to SEQ ID NO: 22;

a first primer of the at least two primers is a primer comprising a nucleotide sequence according to SEQ ID NO: 27 and a second primer of the at least two primers is a primer comprising a nucleotide sequence according to SEQ ID NO: 24;

a first primer of the at least two primers is a primer comprising a nucleotide sequence according to SEQ ID NO: 27 and a second primer of the at least two primers is a primer comprising a nucleotide sequence according to SEQ ID NO: 26; or a first primer of the at least two primers is a primer comprising a nucleotide sequence according to SEQ ID NO:

27 and a second primer of the at least two primers is a primer comprising a nucleotide sequence according to SEQ ID NO: 28.

The various SEQ ID NOs: to which it is referred herein, the compound represented by said SEQ ID NOs:, the organisms from which said sequences were taken and, in some cases, an indication of the corresponding entry of the sequence in publicly available databanks is summarized in the following Table 1:

TABLE 1

SEQ ID NO: 1 is the amino acid sequence of FliD expressed by
H. pylori which corresponds to GenBank entry ACI27464.1.
SEQ ID NO: 2 is the nucleotide sequence (cDNA) of FliD expressed by
H. pylori which corresponds to Genbank entry CP001173.1.
SEQ ID NO: 3 is the amino acid sequence of FliD expressed by H.
suis which corresponds to NCBI Reference Sequence WP_006563874.1.
SEQ ID NO: 4 is the nucleotide sequence (cDNA) of FliD expressed by
H. suis which corresponds to GenBank entry ADGY01000008.1.
SEQ ID NO: 5 is the amino acid sequence of FliD expressed by H.
felis which corresponds to NCBI Reference Sequence YP_004073770.1.
SEQ ID NO: 6 is the nucleotide sequence (cDNA) of FliD expressed by
H. felis which corresponds to GenBank entry FQ670179.2.
SEQ ID NO: 7 is the amino acid sequence of CagA of H. pylori G27
which corresponds to NCBI reference sequence YP_002266135.1.
SEQ ID NO: 8 is the nucleotide sequence (cDNA) of CagA of
H. pylori G27 which corresponds to GenBank entry JQ318032.1.
SEQ ID NO: 9 is the amino acid sequence of VacA of H. pylori
G27 which corresponds to NCBI reference sequence YP_002266461.1.
SEQ ID NO: 10 is the nucleic acid sequence (cDNA) of VacA of H.
pylori
G27 which corresponds to NCBI reference sequence NC_011333.1.
SEQ ID NO: 11 is the amino acid sequence of GroEL of H. pylori
G27 which corresponds to NCBI reference sequence YP_002265651.1.
SEQ ID NO: 12 is the nucleotide sequence (cDNA) of GroEL of H. pylori
G27 which corresponds to NCBI reference sequence NC_011333.1.
SEQ ID NO: 13 is the amino acid sequence of Hp0231 of H. pylori
26695 which corresponds to NCBI reference sequence NP_207029.1.
SEQ ID NO: 14 is the nucleotide sequence (cDNA) of Hp0231 of
H. pylori 26695 which corresponds to NCBI reference sequence
NC_000915.1.
SEQ ID NO: 15 is the amino acid sequence of JHp0940 of H. pylori
J99 which corresponds to NCBI reference sequence NP_223657.1.
SEQ ID NO: 16 is the nucleotide sequence (cDNA) of JHp0940 of H.
pylori J99 which corresponds to NCBI reference sequence NC_000921.1.
SEQ ID NO: 17 is the amino acid sequence of HtrA of H. pylori
G27 which corresponds to NCBI reference sequence YP_002266040.1.
SEQ ID NO: 18 is the nucleotide sequence (cDNA) of HtrA of H. pylori
G27 which corresponds to NCBI reference sequence NC_011333.1.
SEQ ID NO: 19 is a primer used in the cloning of the FliD
gene from H. pylori.
SEQ ID NO: 20 is a primer used in the cloning of the FliD
gene from H. pylori.
SEQ ID NO: 21 is a forward primer used in PCR1 of Example 9.
SEQ ID NO: 22 is a reverse primer used in PCR1 of Example 9.
SEQ ID NO: 23 is a forward primer used in PCR2 of Example 9.
SEQ ID NO: 24 is a reverse primer used in PCR2 of Example 9.
SEQ ID NO: 25 is a forward primer used in PCR3 of Example 9.
SEQ ID NO: 26 is a reverse primer used in PCR3 of Example 9.
SEQ ID NO: 27 is a forward primer used in PCR4 of Example 9.
SEQ ID NO: 28 is a reverse primer used in PCR4 of Example 9.

It will be understood by a person skilled in the art that in case the nucleotide sequence is a DNA sequence and a cDNA sequence in particular, also disclosed herein is a RNA sequence differing from such DNA sequence and cDNA sequence only insofar that the sugar moiety is a ribonucleotide rather than a deoxyribonucleotide.

The present invention is now further illustrated by the following figures and examples which are not intended to limit the scope of protection. From said figures and examples further features, embodiments and advantages may be taken, wherein FIG. 1 shows an embodiment of a line assay used in the methods of the invention for detecting anti-FliD antibodies in serum sample from 20 human patients histologically diagnosed as H. pylori positive;

FIG. 2 shows an embodiment of a lateral flow assay which can be used in the methods of the present invention for detecting anti-FliD antibodies in a sample such as a whole blood sample from a human subject, whereby

Figure 6:
Figure 7:
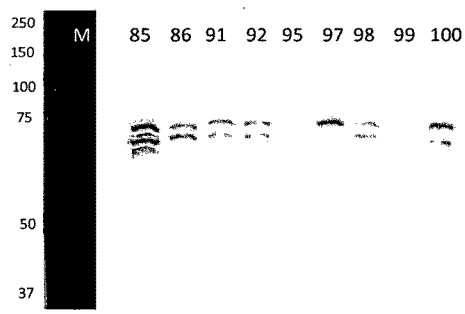
Figure 8:
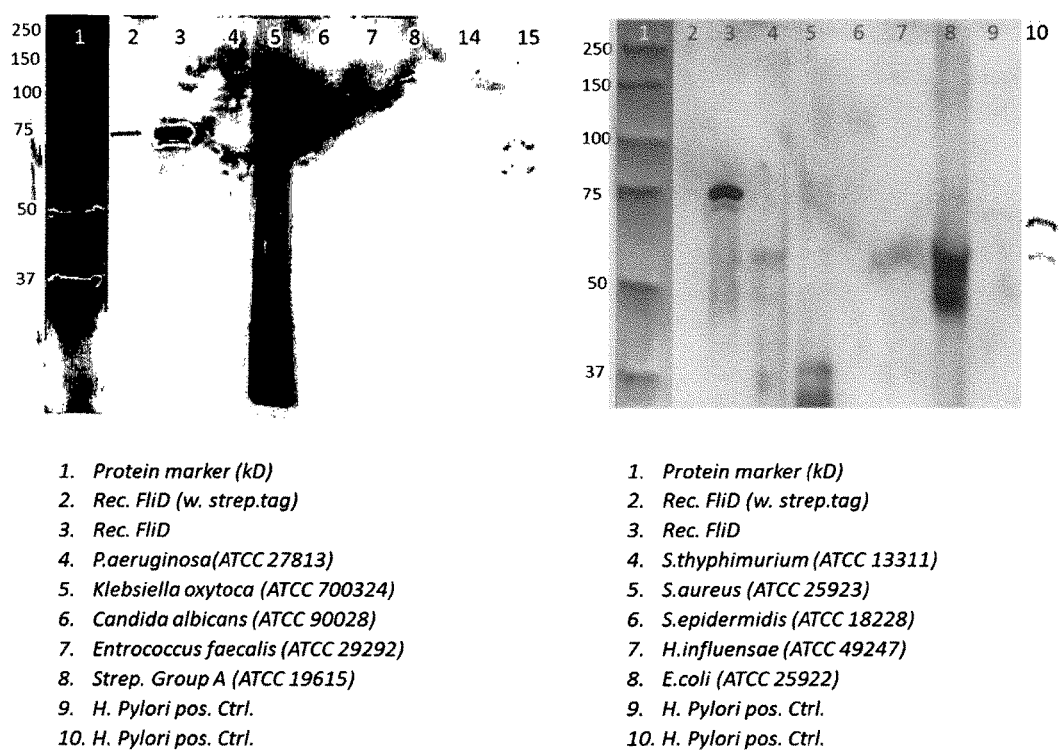

FIG. 6 shows a series of Southern blots using polymerase chain reaction 1 (PCR1), polymerase chain reaction 2 (PCR2), polymerase chain reaction 3 (PCR3) or polymerase chain reaction 4 (PCR4) for the detection of genomic DNA present in representative samples from patients having been diagnosed as H. pylori-positive;

FIG. 7 shows the result of a representative Western blot analysis performed using whole protein lysates of the cultured H. pylori; and FIG. 8 shows the result of two Western blot analyses for determining whether FliD was expressed by the microorganisms indicated underneath each of the Western blots.

EXAMPLE 1: CLONING OF THE H. PYLORI FLID GENE

All DNA manipulations were performed under standard conditions as described by Sambrook et al. (Sambrook, et al., 1989). Briefly, the FliD gene was amplified by PCR using genomic DNA from H. pylori strain J99 as the template. Following oligonucleotides were used as primers: 5'-CAT ATG GCA ATA GGT TCA TTA A-3' (SEQ ID NO: 19) and 5'-CTC GAG ATT CTT TTT AGC CGC TGC-3' (SEQ ID NO: 20). Using this approach a NdeI site was introduced at the 5'-end of forward primers and a XhoI site at 5'-end of the reverse primers. After PCR amplification, the product (2058 bp) was ligated into the pTZ57R/T cloning vector (InsTAclone™ PCR Cloning Kit, MBI Fermentas, Lithuania). Subsequently, the insert was confirmed via PCR and sequencing, and was cloned into a PET-28a(+) expression vector (Qiagen, USA) using NdeI and XhoI restriction enzymes.

EXAMPLE 2: EXPRESSION, PURIFICATION AND RECOGNITION OF RECOMBINANT FLID

E. coli BL21 (Qiagen, USA) competent cells were transformed with pET-28a(+)-fliD and inoculated in LB broth with antibiotic (kanamycin, 50 µg/ml). Expression was induced by addition of 1 mmol/L Isopropyl β-D-1-thiogalactopyranoside (IPTG) at an optical density (OD600) of 0.6. After 4 hours cells were harvested and protein analysis of whole lysate was carried out by sodium dodecyl sulfate-polyacrylamide gel electrophoresis (SDS-PAGE). The soluble histidine-tagged proteins were purified using affinity chromatography (HisTrap crude, GE Healthcare). As a second polishing step and for buffer exchange, size exclusion chromatography (Superdex 75, GE Healthcare) was performed. The relevant fractions were collected and concentrated with a centrifugal filter device (Millipore) with a cut off of 10 kDa and stored at −80° C. Purified recombinant protein was evaluated by Western blot using an anti-His Tag-HRP antibody and also a mouse anti-*H. pylori*-HRP antibody (Pierce, Rockford, USA) and detected by ECL system (GE Healthcare, Uppsala, Sweden).

Amplification of the FliD gene from *H. pylori* strain J99 DNA revealed a single PCR product of 2.05 kb (data not shown) which was confirmed by sequencing and ligated into the expression vector pET-28a(+). After transformation into *E. coli* expression strain BL21 DE3 and induction with IPTG, a clear single band could be observed on Western blot using a commercial polyclonal anti-*H. pylori* antiserum. The protein was purified as described in Materials and Methods to >90% purity (data not shown) and again confirmed by Western blot (data not shown).

EXAMPLE 3: PRODUCTION AND PURIFICATION OF RFLID SPECIFIC ANTIBODY

A mature white New Zealand rabbit was immunized with purified protein according to the protocol of Hay et al. with light modifications (Hay, et al., 2002). Briefly, immunization was carried out by i.m. injection of 250 µg purified recombinant protein (0.5 ml) with the same volume (0.5 ml) of Freund's complete adjuvant. For the recall immunizations, the rabbit was boosted with 125 µg purified protein prepared in the same volume (0.5 ml) of Freund's incomplete adjuvant 4, 6, 8 and 10 weeks later. As a negative control a serum sample was taken prior to immunization. Finally, two weeks after the last immunization, blood was collected and sera separated. Polyclonal IgG antibody was purified by sepharose-4B affinity chromatography using rFliD conjugated columns prepared according to the manufacturer's protocol (Pharmacia, 1988). FliD expression of *H. pylori* (J99) was detected by Western blot using ultrasonic supernatant at the protein concentration of 50 µg/ml. The rabbit polyclonal IgG antibody raised against rFliD protein was used as the first antibody (1:5000 dilution), HRP-labeling sheep antibody against rabbit IgG (Avicenna Research Institute, Tehran, Iran) as the second antibody (1:3000 dilution) and ECL system were used for the detection (Chen, et al., 2001).

Furthermore, to test the antigenicity of the recombinant FliD and to compare it to the native protein, rabbit polyclonal antiserum was produced. Antibody titers were already determined after the third immunization and reached high levels after the fourth boost, confirming the good immunogenicity of FliD. The rabbit antiserum was able to recognize the purified rFliD and FliD in *H. pylori* lysate (data not shown).

EXAMPLE 4: DEVELOPMENT OF AN ELISA

ELISA plates were coated with 100 µl rFliD protein at a concentration of 1 µg/ml in PBS and incubated overnight at 4° C. The coated wells were blocked with phosphate buffered saline (PBS) containing 2.5% bovine serum albumin (BSA, Sigma) for two hours at 37° C. All *H. pylori* positive and negative serologic samples used in this study were screened for antibodies against FliD by using optimal dilution of patients' sera (1:100 dilution) as the first antibody, HRP-conjugated anti-human IgG (Promega, Mannheim, Germany) (1:100 dilution) as the secondary antibody and TMB (3,3',5,5'-tetra methyl benzidine) as a substrate. Moreover, wells were left uncoated as a control for each serum. The result of ELISA for a patient's serum sample was considered to be positive if its OD450 value was over the mean plus 3 SD of negative serum samples (Chen, et al., 2001).

EXAMPLE 5: DEVELOPMENT OF AN FLID LINE ASSAY

A line immunoassay based on recombinant *H. pylori* proteins immobilized on nitrocellulose was prepared. In contrast to ELISA, the test principle allows the identification of specific antibodies against various antigens of *H. pylori* through separate application of different single antigens.

rFliD was immobilized on nitrocellulose membrane strips together with other highly purified recombinant *H. pylori* antigens (CagA, VacA, GroEL, UreA (urease A), HcpC (Cysteine rich protein C) (Mittel et al., 2003) and gGT (gamma glutamyl transferase). The appropriate line conditions for rFliD were determined empirically with a selection of standard serum samples from a previously described study population comprising 20 defined *H. pylori* histologically positive samples and 20 defined *H. pylori* histologically negative samples. The optimal antigen concentration and ideal choice of additives like detergent, dithiothreitol, and NaCl was adjusted for each antigen by repeated cycles of lining and screening. The conditions with best presentation of antigen epitopes and optimal binding to the membrane, observable by perfect band appearance and best discrimination of negative and positive samples, were selected for ideal product specifications of first lots. Control bands were added on the upper end of the strip comprising rabbit anti-human IgG/IgM/IgA antibodies as incubation controls and human IgG, IgM or IgA antibodies as conjugate control as well as a cut off control that allows the assessment of the reactivity of the individual antigen bands.

After scanning and densitometric analysis of the band intensities, the control was used as internal reference to calculate ratios for each band. Usually, cut off control bands are scored between 20 and 30, while strong positive bands can score up to 600 points. Every band scoring above the individual control of the each stripe is considered positive (ratio >1).

Figure 1:
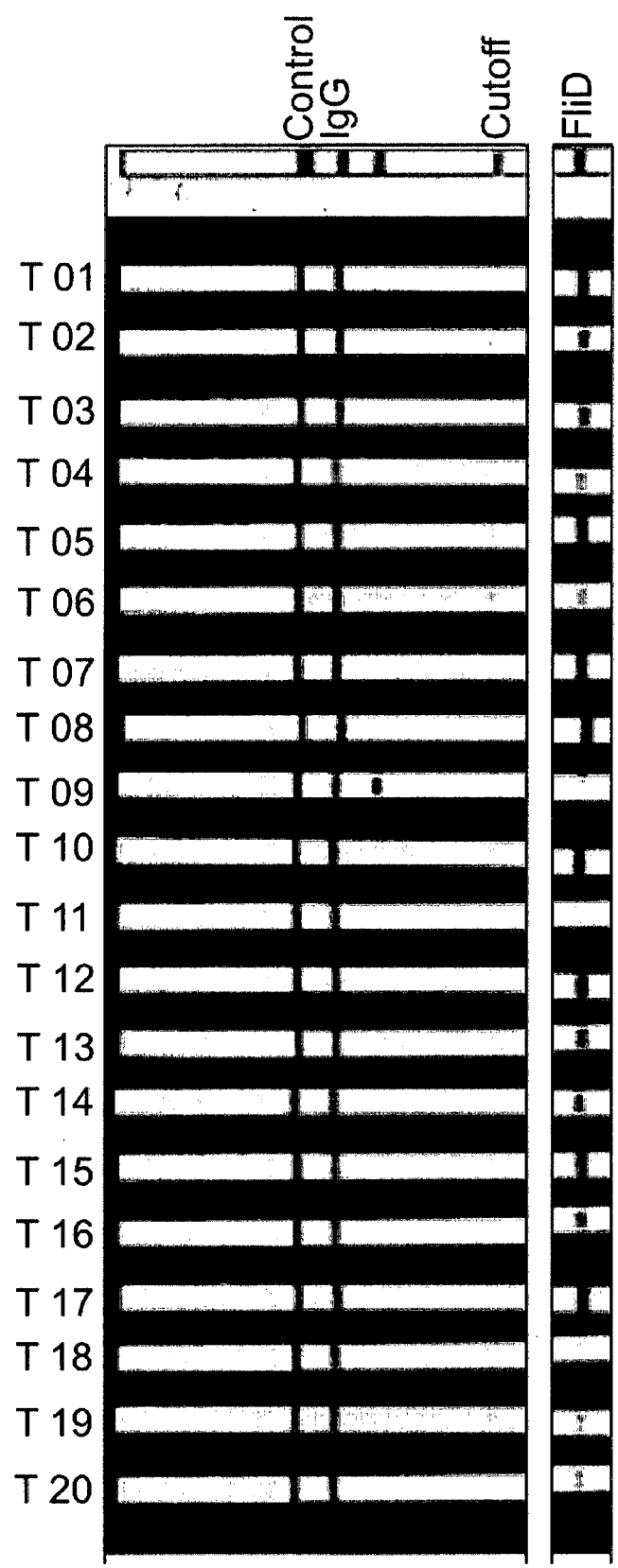

The respective line assay is depicted in FIG. 1

EXAMPLE 6: PROTOTYPE OF A LATERAL FLOW ASSAY FOR THE DIAGNOSIS OF *H. PYLORI*

Using the materials defined above a lateral flow assay was developed based on the principles disclosed herein related to design of a lateral flow assay.

Figure 2A:
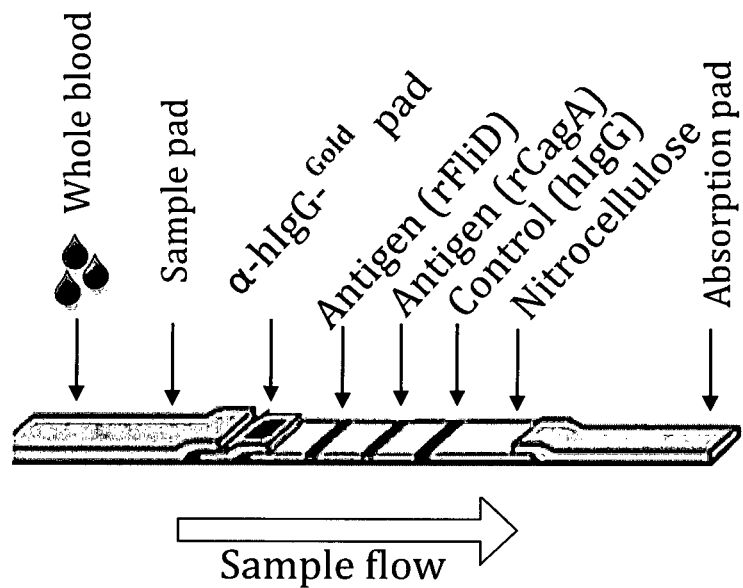
FIG. 2A illustrates the schematic design of the assay.
Figure 2B:
FIG. 2B depicts a result of the assay.

The prototype of such lateral flow assay is depicted in FIG. 2, whereby FIG. 2A illustrates the schematic design of the assay, and FIG. 2B depicts the result of an analysis of a sample obtained from a human being using the assay, wherein anti-FliD antibodies were detected.

As may be taken from FIG. 2A, the assay used anti-hIgG coated gold nanoparticles. rFliD as well as recombinant CagA were present as antigens. hIgG was also immobilized serving as a control. The porous structure was formed by nitrocellulose. Control band indicated that the system work properly. FliD band indicated that the patient had an active or newly treated infection. CagA band, in case of active infection (+FliD band), indicates that this infection must be treated.

EXAMPLE 7: ANALYSIS OF SAMPLES FROM MAN

A total of six hundred and eighteen (618) human patients (308 men, 310 women) were enrolled in the study. After receiving an explanation of the purpose of the study, informed consent was obtained from each patient and a blood sample was taken at the time of endoscopy, before any therapy was initiated. Sera were separated and stored at −20° C. Diagnosis of infection was based on the histopathology as gold standard. Patients were considered *H. pylori* positive when the results of histopathology were positive. All patients were screened by FliD Line assay, and a subset of 246 sera was tested by FliD ELISA as described above and by line assay as described above.

Table 2 shows the results of using said FliD ELISA. More specifically, Table 2 shows FliD serologic response in ELISA comparing *H. pylori* negative and positive human patients.

|  |  | Histology | | |
| --- | --- | --- | --- | --- |
|  |  | Negative | Positive | Total |
| ELISA | Negative | 73 | 8 | 81 |
|  | Positive | 3 | 162 | 165 |
| Total |  | 76 | 170 | 246 |

Table 3 shows the results of using said line assay for a subgroup of the group of patients. More specifically, Table 3 shows FliD serologic response in the line assay comparing *H. pylori* negative and positive patients.

|  |  | Histology | | |
| --- | --- | --- | --- | --- |
|  |  | Negative | Positive | Total |
| Line Assay | Negative | 76 | 14 | 90 |
|  | Positive | 0 | 156 | 156 |
| Total |  | 76 | 170 | 246 |

Using the FliD ELISA, among 170 positive reported samples, 165 positive samples were detected, whereas among 76 samples reported negative 73 were reconfirmed as negative by ELISA (Table 2). Taken together, application of FliD in ELISA based diagnosis of *H. pylori* infection has a specificity of 96% and a sensitivity of 97%. Interestingly, the five cases which were ELISA negative had also low but barely positive scores in the line blot which were just above the cut off (ratios ranging from 1.2 to 2.2). One of these was also regarded *H. pylori* negative by line blot, while the other four were line blot positive, reacting with several other antigens (data not shown). It is important to note that only one sample was negative by both tests.

The entire group of 618 human patients (part of which had been screened by ELISA) was analyzed using the line assay as to antibody response against FliD. a high sensitivity of 97.4% with 310 out of 318 patients evaluated positive in histopathology being positive by line assay, whereas the line assay reaches a specificity of 99% (Table 2). The results from the patients in which discrepant results were obtained, was carefully examined. 8 sera were negative for FliD in the line assay but showed reactivity with other antigens, indicating that here, indeed, FliD was not recognized as antigen. Within these 8 samples, one had no reactivity against the FliD band at all. Seven had a weak reactivity which was barely below the cut off (ratios between 0.6 and 0.95), and four of these had weak reactivities against all other recognized antigens in general (not shown). All three samples in which FliD gave a "false positive" result showed reactivities with other bands as well. All these bands including FliD were relatively weak, but clearly above cut off.

Figure 3:
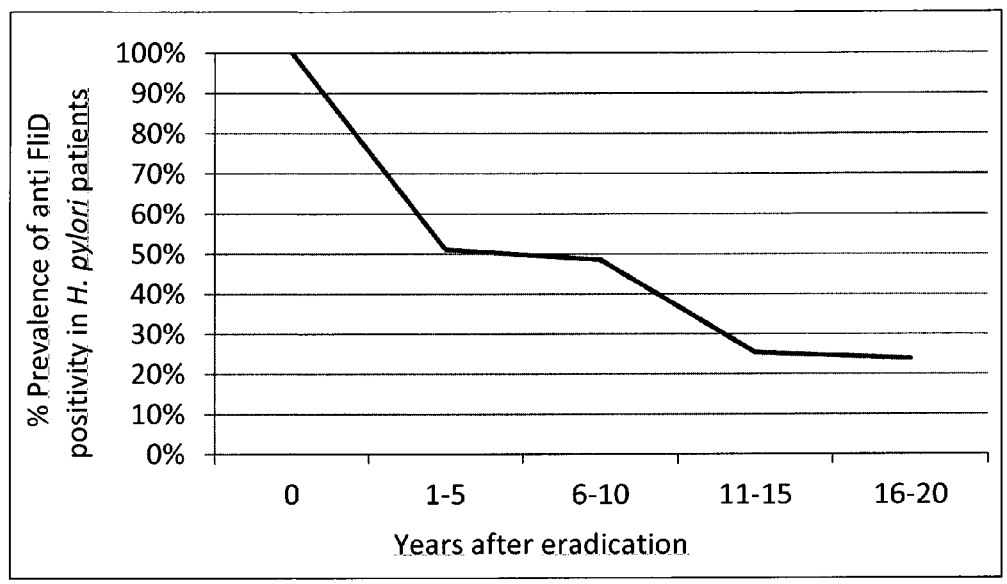
FIG. 3 is a diagram indicating prevalence of an anti-FliD response in samples from man as a function of years after H. pylori eradication.

From said samples the prevalence of an anti-FliD antibody response was determined as a function of years after eradication. The result is shown in FIG. 3. As may be taken from FIG. 3 there is still a prevalence of an anti-FliD antibody response of about 25% after 16 to 20 years after eradication of *H. pylori*.

Figure 4:
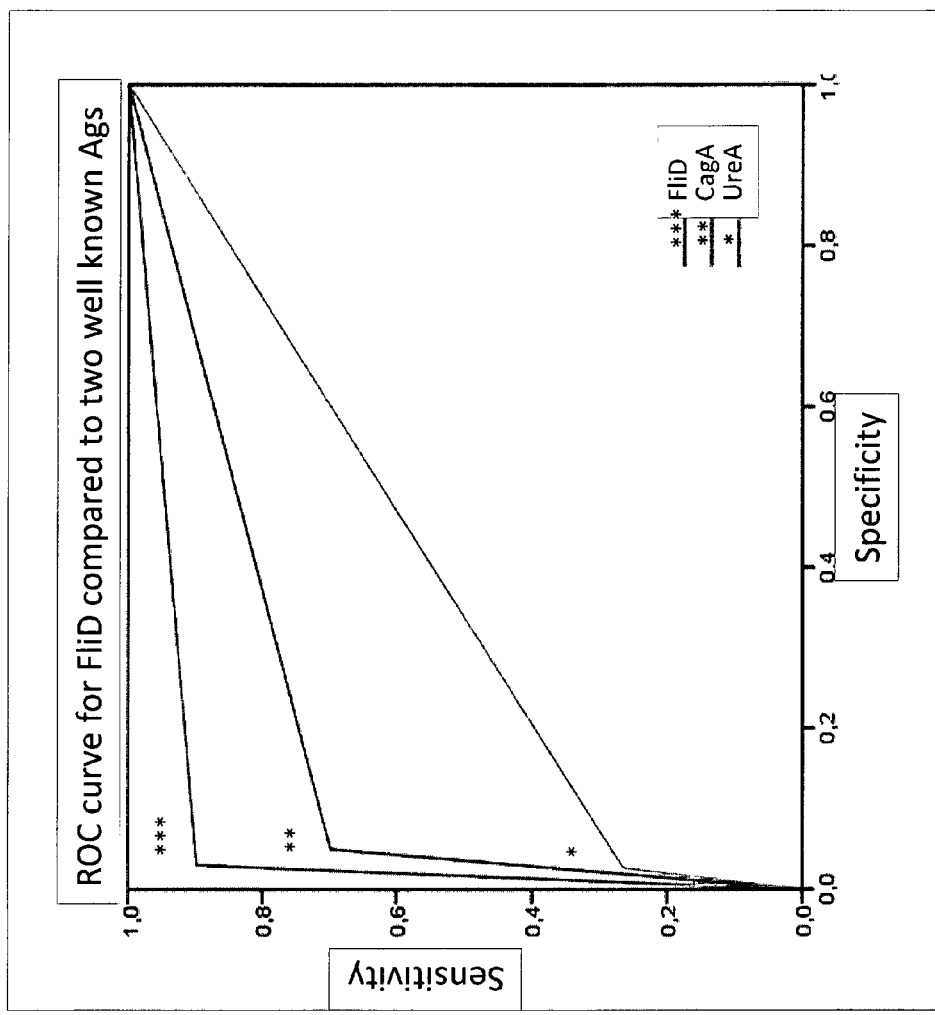
FIG. 4 shows ROC curves for FliD compared to two well-known antigens.

From said samples receiver operating characteristics (ROC) curves have been prepared for FliD, CagA and UreA. The result is shown in FIG. 4. From said FIG. 4 it is evident that FliD is advantageous over the two antigens of the prior art used in the detection of *H. pylori* infection.

EXAMPLE 8: BIOINFORMATIC ANALYSIS OF FLID SEQUENCES

Using bioinformatics tools, FliD protein of *H. pylori* G27 strain was widely compared to other organisms, mainly prokaryotes. This analysis shows more than 97% homology between over 200 *H. pylori* strains.

The results are shown in Table 4.

| Entry | Entry name | Protein names | Organism | Length | Identity | Score |
| --- | --- | --- | --- | --- | --- | --- |
| B5Z7B5 | B5Z7B5_HELPG | Putative flagellar hook-associated protein 2 | *Helicobacter pylori* (strain G27) | 685 | 100.0% | 3412 |
| J0KLR1 | J0KLR1_HELPX | Putative flagellar hook-associated protein 2 | *Helicobacter pylori* Hp H-27 | 685 | 99.0% | 3383 |
| I9RP80 | I9RP80_HELPX | Flagellar capping protein | *Helicobacter pylori* Hp A-20 | 685 | 99.0% | 3381 |
| J0MV71 | J0MV71_HELPX | Putative flagellar hook-associated protein 2 | *Helicobacter pylori* Hp A-27 | 685 | 99.0% | 3379 |
| J0DL62 | J0DL62_HELPX | Flagellar capping protein | *Helicobacter pylori* Hp H-11 | 685 | 99.0% | 3375 |
| J0A5P7 | J0A5P7_HELPX | Flagellar capping protein | *Helicobacter pylori* Hp A-9 | 685 | 98.0% | 3372 |
| J0IU02 | J0IU02_HELPX | Flagellar capping protein | *Helicobacter pylori* NQ4228 | 685 | 99.0% | 3371 |
| K2L7H4 | K2L7H4_HELPX | Flagellar hook-associated protein 2 | *Helicobacter pylori* R036d | 685 | 98.0% | 3370 |
| J0TQK4 | J0TQK4_HELPX | Putative flagellar hook-associated protein 2 | *Helicobacter pylori* Hp P-30 | 685 | 99.0% | 3369 |
| M7RTJ4 | M7RTJ4_HELPX | Flagellar hook-associated protein 2 | *Helicobacter pylori* UMB_G1 | 685 | 98.0% | 3367 |
| K2L537 | K2L537_HELPX | Flagellar hook-associated protein 2 | *Helicobacter pylori* R055a | 685 | 99.0% | 3367 |
| J0SAM4 | J0SAM4_HELPX | Flagellar hook-associated protein 2 | *Helicobacter pylori* Hp P-15b | 685 | 99.0% | 3367 |
| J0M138 | J0M138_HELPX | Putative flagellar hook-associated protein 2 | *Helicobacter pylori* Hp H-45 | 685 | 99.0% | 3367 |
| I9WVW7 | I9WVW7_HELPX | Flagellar capping protein | *Helicobacter pylori* Hp P-15 | 685 | 99.0% | 3367 |
| K2KUE2 | K2KUE2_HELPX | Flagellar hook-associated protein 2 | *Helicobacter pylori* R030b | 685 | 99.0% | 3365 |
| I0EHS2 | I0EHS2_HELPX | Flagellar capping protein | *Helicobacter pylori* PeCan18 | 685 | 98.0% | 3365 |
| H8H4E1 | H8H4E1_HELPX | Flagellar capping protein | *Helicobacter pylori* ELS37 | 685 | 98.0% | 3362 |
| K2LNG6 | K2LNG6_HELPX | Flagellar hook-associated protein 2 | *Helicobacter pylori* R038b | 685 | 98.0% | 3361 |
| D0IS88 | D0IS88_HELP1 | Flagellar hook-associated protein 2 | *Helicobacter pylori* (strain 51) | 685 | 98.0% | 3360 |
| N4T9B5 | N4T9B5_HELPX | Flagellar hook-associated protein 2 | *Helicobacter pylori* Hp A-11 | 685 | 98.0% | 3359 |
| E1PZL2 | E1PZL2_HELPM | Flagellar capping protein | *Helicobacter pylori* (strain SJM180) | 685 | 98.0% | 3358 |
| J0IVU8 | J0IVU8_HELPX | Flagellar capping protein | *Helicobacter pylori* NQ4099 | 685 | 98.0% | 3358 |

-continued

| Entry | Entry name | Protein names | Organism | Length | Identity | Score |
|---|---|---|---|---|---|---|
| J0FGE4 | J0FGE4_HELPX | Putative flagellar hook-associated protein 2 | *Helicobacter pylori* Hp P-16 | 685 | 98.0% | 3358 |
| Q1CTB8 | Q1CTB8_HELPH | Putative flagellar hook-associated protein 2 | *Helicobacter pylori* (strain HPAG1) | 685 | 98.0% | 3357 |
| E8QPN8 | E8QPN8_HELPR | Flagellar capping protein | *Helicobacter pylori* (strain Lithuania75) | 685 | 98.0% | 3355 |
| K2KUX6 | K2KUX6_HELPX | Flagellar hook-associated protein 2 | *Helicobacter pylori* R32b | 685 | 98.0% | 3355 |
| K2KMU9 | K2KMU9_HELPX | Flagellar hook-associated protein 2 | *Helicobacter pylori* R037c | 685 | 98.0% | 3355 |
| J0HQJ3 | J0HQJ3_HELPX | Flagellar capping protein | *Helicobacter pylori* CPY1124 | 685 | 98.0% | 3355 |
| I9XF52 | I9XF52_HELPX | Flagellar hook-associated protein 2 | *Helicobacter pylori* Hp P-74 | 685 | 98.0% | 3355 |
| I9U4H5 | I9U4H5_HELPX | Flagellar hook-associated protein 2 | *Helicobacter pylori* Hp A-26 | 685 | 98.0% | 3355 |
| D7FEA9 | D7FEA9_HELP3 | Flagellar hook-associated protein 2 | *Helicobacter pylori* (strain B8) | 685 | 98.0% | 3354 |
| I9US75 | I9US75_HELPX | Flagellar hook-associated protein 2 | *Helicobacter pylori* Hp H-9 | 685 | 98.0% | 3354 |
| B9XZK1 | B9XZK1_HELPX | Putative uncharacterized protein | *Helicobacter pylori* B128 | 685 | 98.0% | 3354 |
| J0J9Q0 | J0J9Q0_HELPX | Flagellar capping protein | *Helicobacter pylori* NQ4076 | 685 | 98.0% | 3353 |
| I9QZB4 | I9QZB4_HELPX | Flagellar capping protein | *Helicobacter pylori* NQ4110 | 685 | 98.0% | 3353 |
| G2M3P3 | G2M3P3_HELPX | Flagellar capping protein | *Helicobacter pylori* Puno120 | 685 | 98.0% | 3352 |
| E1QBB7 | E1QBB7_HELPC | Flagellar capping protein | *Helicobacter pylori* (strain Cuz20) | 685 | 98.0% | 3351 |
| J0LRM5 | J0LRM5_HELPX | Flagellar capping protein | *Helicobacter pylori* Hp H-43 | 685 | 98.0% | 3351 |
| E6NRT1 | E6NRT1_HELPQ | Flagellar capping protein | *Helicobacter pylori* (strain F57) | 685 | 98.0% | 3350 |
| M3MVK5 | M3MVK5_HELPX | Flagellar hook-associated protein 2 | *Helicobacter pylori* GAM114Ai | 685 | 98.0% | 3350 |
| K2KRX5 | K2KRX5_HELPX | Flagellar hook-associated protein 2 | *Helicobacter pylori* R018c | 685 | 98.0% | 3350 |
| K2KFQ1 | K2KFQ1_HELPX | Flagellar hook-associated protein 2 | *Helicobacter pylori* R056a | 685 | 98.0% | 3350 |
| J0IGN4 | J0IGN4_HELPX | Flagellar capping protein | *Helicobacter pylori* NQ4216 | 685 | 98.0% | 3349 |
| E6S1Q8 | E6S1Q8_HELPF | Flagellar hook-associated protein 2 | *Helicobacter pylori* (strain 35A) | 685 | 98.0% | 3348 |
| I9YJR2 | I9YJR2_HELPX | Flagellar hook-associated protein 2 | *Helicobacter pylori* Hp P-13b | 685 | 98.0% | 3348 |
| I9WT57 | I9WT57_HELPX | Flagellar hook-associated protein 2 | *Helicobacter pylori* Hp P-13 | 685 | 98.0% | 3348 |
| I9U161 | I9U161_HELPX | Flagellar capping protein | *Helicobacter pylori* Hp A-14 | 685 | 98.0% | 3348 |
| B6JLY6 | B6JLY6_HELP2 | Flagellar hook-associated protein 2 | *Helicobacter pylori* (strain P12) | 685 | 98.0% | 3347 |
| K2K5F9 | K2K5F9_HELPX | Flagellar hook-associated protein 2 | *Helicobacter pylori* R046Wa | 685 | 98.0% | 3347 |
| I9XUJ1 | I9XUJ1_HELPX | Flagellar hook-associated protein 2 | *Helicobacter pylori* CPY1313 | 685 | 98.0% | 3347 |
| I9PV13 | I9PV13_HELPX | Flagellar hook-associated protein 2 | *Helicobacter pylori* CPY6311 | 685 | 98.0% | 3347 |
| I9PLR1 | I9PLR1_HELPX | Flagellar capping protein | *Helicobacter pylori* CPY6261 | 685 | 98.0% | 3347 |
| L8VWS3 | L8VWS3_HELPX | Flagellar capping protein | *Helicobacter pylori* A45 | 685 | 98.0% | 3346 |
| K7Y5K8 | K7Y5K8_HELPX | Flagellar capping protein | *Helicobacter pylori* Aklavik117 | 685 | 98.0% | 3346 |
| J0T145 | J0T145_HELPX | Flagellar hook-associated protein 2 | *Helicobacter pylori* Hp M2 | 685 | 98.0% | 3346 |
| I9T4Z9 | I9T4Z9_HELPX | Flagellar hook-associated protein 2 | *Helicobacter pylori* Hp H-44 | 685 | 98.0% | 3346 |
| E8QFQ7 | E8QFQ7_HELP7 | Flagellar capping protein | *Helicobacter pylori* (strain India7) | 685 | 98.0% | 3345 |
| C7BX84 | C7BX84_HELPB | Flagellar hook-associated protein 2 FliD | *Helicobacter pylori* (strain B38) | 685 | 98.0% | 3345 |
| I9W7Z2 | I9W7Z2_HELPX | Flagellar hook-associated protein 2 | *Helicobacter pylori* Hp P-2 | 685 | 98.0% | 3345 |
| I0ZBA9 | I0ZBA9_HELPX | Flagellar capping protein | *Helicobacter pylori* P79 | 685 | 98.0% | 3345 |
| F4D517 | F4D517_HELPX | Flagellar hook-associated protein 2 | *Helicobacter pylori* 83 | 685 | 98.0% | 3345 |
| B9XUM1 | B9XUM1_HELPX | Putative uncharacterized protein | *Helicobacter pylori* 98-10 | 685 | 98.0% | 3345 |
| P96786 | FLID_HELPY | Flagellar hook-associated protein 2 (HAP2) (Filament cap protein) (Flagellar cap protein) | *Helicobacter pylori* (strain ATCC 700392/26695) (*Campylobacter pylori*) | 685 | 98.0% | 3345 |
| M3SDI9 | M3SDI9_HELPX | Flagellar hook-associated protein 2 | *Helicobacter pylori* GAMchJs106B | 685 | 98.0% | 3344 |
| I9XAU3 | I9XAU3_HELPX | Flagellar capping protein | *Helicobacter pylori* Hp P-23 | 685 | 98.0% | 3344 |
| I9PTN1 | I9PTN1_HELPX | Flagellar capping protein | *Helicobacter pylori* CPY6271 | 685 | 98.0% | 3344 |
| G2M8C7 | G2M8C7_HELPX | Flagellar capping protein | *Helicobacter pylori* Puno135 | 685 | 98.0% | 3344 |
| E1Q6P5 | E1Q6P5_HELPP | Flagellar capping protein | *Helicobacter pylori* (strain PeCan4) | 685 | 98.0% | 3343 |
| M3KWT6 | M3KWT6_HELPX | Flagellar hook-associated protein 2 | *Helicobacter pylori* GAM119Bi | 685 | 98.0% | 3343 |
| I0ZGY9 | I0ZGY9_HELPX | Flagellar capping protein | *Helicobacter pylori* NCTC 11637 = CCUG 17874 | 685 | 98.0% | 3343 |
| I2DFT2 | I2DFT2_HELPX | Flagellar capping protein | *Helicobacter pylori* XZ274 | 685 | 98.0% | 3342 |
| E6NKD5 | E6NKD5_HELPL | Flagellar capping protein | *Helicobacter pylori* (strain F32) | 685 | 98.0% | 3341 |
| E6NIS5 | E6NIS5_HELPK | Flagellar capping protein | *Helicobacter pylori* (strain F30) | 685 | 98.0% | 3341 |
| I9ZP80 | I9ZP80_HELPX | Flagellar hook-associated protein 2 | *Helicobacter pylori* NQ4161 | 685 | 98.0% | 3341 |
| I9RRM1 | I9RRM1_HELPX | Flagellar hook-associated protein 2 | *Helicobacter pylori* Hp A-17 | 685 | 98.0% | 3341 |
| J0A0N9 | J0A0N9_HELPX | Flagellar hook-associated protein | *Helicobacter pylori* Hp P-26 | 685 | 97.0% | 3340 |
| I9QGH5 | I9QGH5_HELPX | Flagellar hook-associated protein 2 | *Helicobacter pylori* NQ4053 | 685 | 98.0% | 3340 |
| D6XPZ1 | D6XPZ1_HELPV | Flagellar hook-associated protein 2 | *Helicobacter pylori* (strain v225d) | 685 | 98.0% | 3339 |
| M5YZL4 | M5YZL4_HELPX | Flagellar hook-associated protein 2 | *Helicobacter pylori* GAMchJs124i | 685 | 97.0% | 3339 |
| M5YMA1 | M5YMA1_HELPX | Flagellar hook-associated protein 2 | *Helicobacter pylori* GAMchJs114i | 685 | 97.0% | 3339 |
| M4ZNA5 | M4ZNA5_HELPX | Flagellar capping protein | *Helicobacter pylori* OK310 | 685 | 97.0% | 3339 |
| M3NNS0 | M3NNS0_HELPX | Flagellar hook-associated protein 2 | *Helicobacter pylori* GAM246Ai | 685 | 97.0% | 3339 |
| M3MBN7 | M3MBN7_HELPX | Flagellar hook-associated protein 2 | *Helicobacter pylori* GAM105Ai | 685 | 97.0% | 3339 |
| I9S784 | I9S784_HELPX | Flagellar capping protein | *Helicobacter pylori* Hp H-28 | 685 | 98.0% | 3339 |
| I0E4K1 | I0E4K1_HELPX | Flagellar capping protein | *Helicobacter pylori* Shi417 | 685 | 98.0% | 3339 |
| J0P747 | J0P747_HELPX | Flagellar hook-associated protein | *Helicobacter pylori* Hp H-23 | 685 | 97.0% | 3338 |
| J0N2H0 | J0N2H0_HELPX | Flagellar hook-associated protein | *Helicobacter pylori* Hp H-4 | 685 | 97.0% | 3338 |
| I0ED42 | I0ED42_HELPX | Flagellar capping protein | *Helicobacter pylori* Shi112 | 685 | 98.0% | 3338 |
| M7SSG1 | M7SSG1_HELPX | Flagellar hook-associated protein 2 | *Helicobacter pylori* CPY1662 | 685 | 97.0% | 3337 |
| M5Y955 | M5Y955_HELPX | Flagellar hook-associated protein 2 | *Helicobacter pylori* GAMchJs117Ai | 685 | 97.0% | 3337 |
| M4ZKA3 | M4ZKA3_HELPX | Flagellar capping protein | *Helicobacter pylori* OK113 | 685 | 98.0% | 3337 |
| M3LA33 | M3LA33_HELPX | Flagellar hook-associated protein 2 | *Helicobacter pylori* GAM231Ai | 685 | 97.0% | 3337 |
| I9Z0G2 | I9Z0G2_HELPX | Flagellar hook-associated protein 2 | *Helicobacter pylori* Hp P-28b | 685 | 97.0% | 3337 |
| I9S3M7 | I9S3M7_HELPX | Flagellar hook-associated protein 2 | *Helicobacter pylori* Hp H-24 | 685 | 98.0% | 3337 |
| I0EWG9 | I0EWG9_HELPX | Flagellar capping protein | *Helicobacter pylori* HUP-B14 | 685 | 97.0% | 3337 |

-continued

| Entry | Entry name | Protein names | Organism | Length | Identity | Score |
|---|---|---|---|---|---|---|
| M3PSG4 | M3PSG4_HELPX | Flagellar hook-associated protein 2 | *Helicobacter pylori* GAM96Ai | 685 | 97.0% | 3336 |
| J0U8I3 | J0U8I3_HELPX | Flagellar hook-associated protein 2 | *Helicobacter pylori* Hp P-3b | 685 | 97.0% | 3336 |
| J0RUS2 | J0RUS2_HELPX | Flagellar hook-associated protein 2 | *Helicobacter pylori* Hp H-5b | 685 | 97.0% | 3336 |
| J0Q0D5 | J0Q0D5_HELPX | Flagellar hook-associated protein 2 | *Helicobacter pylori* Hp P-4 | 685 | 97.0% | 3336 |
| J0PSB5 | J0PSB5_HELPX | Flagellar hook-associated protein 2 | *Helicobacter pylori* Hp P-3 | 685 | 97.0% | 3336 |
| I9Y932 | I9Y932_HELPX | Flagellar hook-associated protein 2 | *Helicobacter pylori* Hp P-4c | 685 | 97.0% | 3336 |
| I9XWQ4 | I9XWQ4_HELPX | Flagellar hook-associated protein 2 | *Helicobacter pylori* Hp P-4d | 685 | 97.0% | 3336 |
| E6NDJ6 | E6NDJ6_HELPI | Flagellar capping protein | *Helicobacter pylori* (strain F16) | 685 | 97.0% | 3334 |
| M3QDF1 | M3QDF1_HELPX | Flagellar hook-associated protein 2 | *Helicobacter pylori* GAM80Ai | 685 | 97.0% | 3334 |
| M3Q5B9 | M3Q5B9_HELPX | Flagellar hook-associated protein 2 | *Helicobacter pylori* GAM42Ai | 685 | 97.0% | 3334 |
| M3P646 | M3P646_HELPX | Flagellar hook-associated protein 2 | *Helicobacter pylori* GAM245Ai | 685 | 97.0% | 3334 |
| M3LV71 | M3LV71_HELPX | Flagellar hook-associated protein 2 | *Helicobacter pylori* GAM112Ai | 685 | 97.0% | 3334 |
| M3L655 | M3L655_HELPX | Flagellar hook-associated protein 2 | *Helicobacter pylori* GAM101Biv | 685 | 97.0% | 3334 |
| E1S8R1 | E1S8R1_HELP9 | Flagellar hook-associated protein | *Helicobacter pylori* (strain 908) | 685 | 97.0% | 3333 |
| E1PVI4 | E1PVI4_HELPT | Flagellar capping protein | *Helicobacter pylori* (strain Sat464) | 685 | 98.0% | 3333 |
| D0JZC3 | D0JZC3_HELP5 | Flagellar capping protein | *Helicobacter pylori* (strain 52) | 685 | 97.0% | 3333 |
| M3RS44 | M3RS44_HELPX | Flagellar hook-associated protein 2 | *Helicobacter pylori* HP116Bi | 685 | 97.0% | 3333 |
| M3R005 | M3R005_HELPX | Flagellar hook-associated protein 2 | *Helicobacter pylori* GAM264Ai | 685 | 97.0% | 3333 |
| M3MJ19 | M3MJ19_HELPX | Flagellar hook-associated protein 2 | *Helicobacter pylori* GAM103Bi | 685 | 97.0% | 3333 |
| J0I156 | J0I156_HELPX | Flagellar capping protein | *Helicobacter pylori* CPY3281 | 685 | 98.0% | 3333 |
| J0AJS5 | J0AJS5_HELPX | Flagellar hook-associated protein | *Helicobacter pylori* Hp H-16 | 685 | 97.0% | 3333 |
| I0E947 | I0E947_HELPX | Flagellar capping protein | *Helicobacter pylori* Shi169 | 685 | 98.0% | 3333 |
| F2JET0 | F2JET0_HELP9 | Flagellar hook-associated protein | *Helicobacter pylori* 2018 | 685 | 97.0% | 3333 |
| F2JAT7 | F2JAT7_HELP9 | Flagellar hook-associated protein | *Helicobacter pylori* 2017 | 685 | 97.0% | 3333 |
| Q9ZL91 | FLID_HELPJ | Flagellar hook-associated protein 2 (HAP2) (Filament cap protein) (Flagellar cap protein) | *Helicobacter pylori* (strain J99) (*Campylobacter pylori* J99) | 685 | 97.0% | 3333 |
| M3NID0 | M3NID0_HELPX | Flagellar hook-associated protein 2 | *Helicobacter pylori* GAM270ASi | 685 | 97.0% | 3332 |
| J0DCU5 | J0DCU5_HELPX | Flagellar hook-associated protein 2 | *Helicobacter pylori* Hp H-6 | 685 | 97.0% | 3332 |
| I9V408 | I9V408_HELPX | Flagellar capping protein | *Helicobacter pylori* Hp H-10 | 685 | 97.0% | 3332 |
| J0U3G8 | J0U3G8_HELPX | Flagellar hook-associated protein 2 | *Helicobacter pylori* Hp P-62 | 685 | 97.0% | 3331 |
| I9SL37 | I9SL37_HELPX | Flagellar hook-associated protein | *Helicobacter pylori* Hp H-29 | 685 | 97.0% | 3331 |
| E8QM56 | E8QM56_HELP4 | Flagellar capping protein | *Helicobacter pylori* (strain Gambia94/24) | 685 | 97.0% | 3330 |
| M5YNV6 | M5YNV6_HELPX | Flagellar hook-associated protein 2 | *Helicobacter pylori* GAMchJs136i | 685 | 97.0% | 3330 |
| M3TQ89 | M3TQ89_HELPX | Flagellar hook-associated protein 2 | *Helicobacter pylori* HP260Bi | 685 | 97.0% | 3330 |
| M3QIV4 | M3QIV4_HELPX | Flagellar hook-associated protein 2 | *Helicobacter pylori* GAM260Bi | 685 | 97.0% | 3330 |
| M3Q2L5 | M3Q2L5_HELPX | Flagellar hook-associated protein 2 | *Helicobacter pylori* GAM263BFi | 685 | 97.0% | 3330 |
| M3M583 | M3M583_HELPX | Flagellar hook-associated protein 2 | *Helicobacter pylori* GAM115Ai | 685 | 97.0% | 3330 |
| J0SFX5 | J0SFX5_HELPX | Flagellar hook-associated protein 2 | *Helicobacter pylori* Hp P-25c | 685 | 97.0% | 3330 |
| J0HGQ0 | J0HGQ0_HELPX | Flagellar hook-associated protein 2 | *Helicobacter pylori* Hp P-25d | 685 | 97.0% | 3330 |
| I9X9I1 | I9X9I1_HELPX | Flagellar hook-associated protein 2 | *Helicobacter pylori* Hp P-25 | 685 | 97.0% | 3330 |
| I9VCT9 | I9VCT9_HELPX | Flagellar hook-associated protein | *Helicobacter pylori* Hp H-19 | 685 | 97.0% | 3330 |
| M3S7G6 | M3S7G6_HELPX | Flagellar hook-associated protein 2 | *Helicobacter pylori* GAM83T | 685 | 97.0% | 3329 |
| M3PEV1 | M3PEV1_HELPX | Flagellar hook-associated protein 2 | *Helicobacter pylori* GAM244Ai | 685 | 97.0% | 3329 |
| M3P9F3 | M3P9F3_HELPX | Flagellar hook-associated protein 2 | *Helicobacter pylori* GAM83Bi | 685 | 97.0% | 3329 |
| M3NFC4 | M3NFC4_HELPX | Flagellar hook-associated protein 2 | *Helicobacter pylori* GAM118Bi | 685 | 97.0% | 3329 |
| K8GY42 | K8GY42_HELPX | Flagellar hook-associated protein 2 | *Helicobacter pylori* GAM100Ai | 685 | 97.0% | 3329 |
| J0UFU9 | J0UFU9_HELPX | Flagellar hook-associated protein 2 | *Helicobacter pylori* Hp M9 | 685 | 97.0% | 3329 |
| J0T5P3 | J0T5P3_HELPX | Flagellar hook-associated protein 2 | *Helicobacter pylori* Hp M4 | 685 | 97.0% | 3329 |
| J0REL3 | J0REL3_HELPX | Flagellar hook-associated protein 2 | *Helicobacter pylori* Hp H-24c | 685 | 97.0% | 3329 |
| J0I743 | J0I743_HELPX | Flagellar hook-associated protein 2 | *Helicobacter pylori* Hp M5 | 685 | 97.0% | 3329 |
| J0I1J2 | J0I1J2_HELPX | Flagellar hook-associated protein 2 | *Helicobacter pylori* Hp M3 | 685 | 97.0% | 3329 |
| J0HJK5 | J0HJK5_HELPX | Flagellar hook-associated protein 2 | *Helicobacter pylori* Hp M1 | 685 | 97.0% | 3329 |
| I9ZYP3 | I9ZYP3_HELPX | Flagellar hook-associated protein 2 | *Helicobacter pylori* Hp M6 | 685 | 97.0% | 3329 |
| I9XJ16 | I9XJ16_HELPX | Flagellar hook-associated protein 2 | *Helicobacter pylori* Hp H-24b | 685 | 97.0% | 3329 |
| M3UI84 | M3UI84_HELPX | Flagellar hook-associated protein 2 | *Helicobacter pylori* HP260BFii | 685 | 97.0% | 3328 |
| M3U8F0 | M3U8F0_HELPX | Flagellar hook-associated protein 2 | *Helicobacter pylori* HP250BSi | 685 | 97.0% | 3328 |
| M3T9M6 | M3T9M6_HELPX | Flagellar hook-associated protein 2 | *Helicobacter pylori* HP250ASi | 685 | 97.0% | 3328 |
| M3T443 | M3T443_HELPX | Flagellar hook-associated protein 2 | *Helicobacter pylori* HP250ASii | 685 | 97.0% | 3328 |
| M3T0U7 | M3T0U7_HELPX | Flagellar hook-associated protein 2 | *Helicobacter pylori* HP250AFiV | 685 | 97.0% | 3328 |
| M3SWF6 | M3SWF6_HELPX | Flagellar hook-associated protein 2 | *Helicobacter pylori* HP250BFiV | 685 | 97.0% | 3328 |
| M3SP57 | M3SP57_HELPX | Flagellar hook-associated protein 2 | *Helicobacter pylori* HP250AFiii | 685 | 97.0% | 3328 |
| M3S6F4 | M3S6F4_HELPX | Flagellar hook-associated protein 2 | *Helicobacter pylori* HP250BFiii | 685 | 97.0% | 3328 |
| M3R7T2 | M3R7T2_HELPX | Flagellar hook-associated protein 2 | *Helicobacter pylori* HP250AFii | 685 | 97.0% | 3328 |
| M3QV83 | M3QV83_HELPX | Flagellar hook-associated protein 2 | *Helicobacter pylori* GAM260BSi | 685 | 97.0% | 3328 |
| M3QS41 | M3QS41_HELPX | Flagellar hook-associated protein 2 | *Helicobacter pylori* HP250BFii | 685 | 97.0% | 3328 |
| M3QQ64 | M3QQ64_HELPX | Flagellar hook-associated protein 2 | *Helicobacter pylori* HP250BFi | 685 | 97.0% | 3328 |
| M3Q6I7 | M3Q6I7_HELPX | Flagellar hook-associated protein 2 | *Helicobacter pylori* GAM250T | 685 | 97.0% | 3328 |
| M3NV58 | M3NV58_HELPX | Flagellar hook-associated protein 2 | *Helicobacter pylori* GAM252Bi | 685 | 97.0% | 3328 |
| M3NKC5 | M3NKC5_HELPX | Flagellar hook-associated protein 2 | *Helicobacter pylori* GAM252T | 685 | 97.0% | 3328 |
| M3LZX8 | M3LZX8_HELPX | Flagellar hook-associated protein 2 | *Helicobacter pylori* GAM250AFi | 685 | 97.0% | 3328 |
| J0CLQ3 | J0CLQ3_HELPX | Flagellar hook-associated protein 2 | *Helicobacter pylori* Hp A-16 | 685 | 97.0% | 3328 |
| I9XTZ6 | I9XTZ6_HELPX | Flagellar capping protein | *Helicobacter pylori* CPY1962 | 685 | 98.0% | 3328 |
| B2UT80 | B2UT80_HELPS | Flagellar capping protein | *Helicobacter pylori* (strain Shi470) | 685 | 97.0% | 3327 |
| M7SW73 | M7SW73_HELPX | Flagellar hook-associated protein 2 | *Helicobacter pylori* Hp H-1 | 685 | 97.0% | 3327 |
| M3P129 | M3P129_HELPX | Flagellar hook-associated protein 2 | *Helicobacter pylori* GAM254Ai | 685 | 97.0% | 3327 |
| I9P985 | I9P985_HELPX | Flagellar capping protein | *Helicobacter pylori* CPY6081 | 685 | 97.0% | 3326 |

-continued

| Entry | Entry name | Protein names | Organism | Length | Identity | Score |
|---|---|---|---|---|---|---|
| K7YA88 | K7YA88_HELPX | Flagellar capping protein | *Helicobacter pylori* Aklavik86 | 685 | 97.0% | 3325 |
| M3RIK8 | M3RIK8_HELPX | Flagellar hook-associated protein 2 | *Helicobacter pylori* GAM93Bi | 685 | 97.0% | 3324 |
| J0M8U8 | J0M8U8_HELPX | Flagellar hook-associated protein 2 | *Helicobacter pylori* Hp A-6 | 685 | 97.0% | 3324 |
| M3NGP1 | M3NGP1_HELPX | Flagellar hook-associated protein 2 | *Helicobacter pylori* GAM265BSii | 685 | 97.0% | 3323 |
| M3KZM7 | M3KZM7_HELPX | Flagellar hook-associated protein 2 | *Helicobacter pylori* GAM120Ai | 685 | 97.0% | 3323 |
| M3PUQ6 | M3PUQ6_HELPX | Flagellar hook-associated protein 2 | *Helicobacter pylori* GAM249T | 685 | 97.0% | 3322 |
| M3PCL7 | M3PCL7_HELPX | Flagellar hook-associated protein 2 | *Helicobacter pylori* GAM239Bi | 685 | 97.0% | 3322 |
| M3NM23 | M3NM23_HELPX | Flagellar hook-associated protein 2 | *Helicobacter pylori* GAM121Aii | 685 | 97.0% | 3322 |
| J0IWR3 | J0IWR3_HELPX | Flagellar hook-associated protein 2 | *Helicobacter pylori* NQ4200 | 685 | 97.0% | 3322 |
| J0PFP0 | J0PFP0_HELPX | Flagellar hook-associated protein 2 | *Helicobacter pylori* Hp P-1 | 685 | 97.0% | 3321 |
| I9XPS7 | I9XPS7_HELPX | Flagellar hook-associated protein 2 | *Helicobacter pylori* Hp P-1b | 685 | 97.0% | 3321 |
| J0N254 | J0N254_HELPX | Flagellar hook-associated protein 2 | *Helicobacter pylori* Hp H-3 | 685 | 97.0% | 3320 |
| M3U8B7 | M3U8B7_HELPX | Flagellar hook-associated protein 2 | *Helicobacter pylori* HP260AFii | 685 | 97.0% | 3319 |
| M3U287 | M3U287_HELPX | Flagellar hook-associated protein 2 | *Helicobacter pylori* HP260AFi | 685 | 97.0% | 3319 |
| M3RLI9 | M3RLI9_HELPX | Flagellar hook-associated protein 2 | *Helicobacter pylori* HP260ASii | 685 | 97.0% | 3319 |
| M3Q751 | M3Q751_HELPX | Flagellar hook-associated protein 2 | *Helicobacter pylori* GAM268Bii | 685 | 97.0% | 3319 |
| M3P4U3 | M3P4U3_HELPX | Flagellar hook-associated protein 2 | *Helicobacter pylori* GAM260ASi | 685 | 97.0% | 3319 |
| M3LLE6 | M3LLE6_HELPX | Flagellar hook-associated protein 2 | *Helicobacter pylori* GAM201Ai | 685 | 97.0% | 3318 |
| J0JT98 | J0JT98_HELPX | Flagellar hook-associated protein 2 | *Helicobacter pylori* Hp A-5 | 680 | 98.0% | 3318 |
| I9SDQ6 | I9SDQ6_HELPX | Flagellar hook-associated protein 2 | *Helicobacter pylori* Hp H-30 | 685 | 97.0% | 3314 |
| J0BNB3 | J0BNB3_HELPX | Flagellar hook-associated protein | *Helicobacter pylori* Hp H42 | 677 | 97.0% | 3311 |
| G2MEG6 | G2MEG6_HELPX | Flagellar capping protein | *Helicobacter pylori* SNT49 | 685 | 97.0% | 3311 |
| J0UBP3 | J0UBP3_HELPX | Flagellar hook-associated protein 2 | *Helicobacter pylori* Hp P-2b | 677 | 97.0% | 3308 |
| I9QNB9 | I9QNB9_HELPX | Flagellar hook-associated protein 2 | *Helicobacter pylori* NQ4044 | 685 | 96.0% | 3302 |
| I9ZZM5 | I9ZZM5_HELPX | Flagellar hook-associated protein 2 | *Helicobacter pylori* Hp A-4 | 677 | 97.0% | 3300 |
| M7SHH3 | M7SHH3_HELPX | Flagellar hook-associated protein 2 | *Helicobacter pylori* CCHI 33 | 677 | 97.0% | 3297 |
| I9TJA1 | I9TJA1_HELPX | Flagellar hook-associated protein 2 | *Helicobacter pylori* Hp A-8 | 677 | 97.0% | 3297 |
| M3NMW6 | M3NMW6_HELPX | Flagellar hook-associated protein 2 | *Helicobacter pylori* GAM210Bi | 685 | 96.0% | 3296 |
| I9YL06 | I9YL06_HELPX | Flagellar hook-associated protein 2 | *Helicobacter pylori* Hp P-11b | 677 | 97.0% | 3293 |
| I9WS67 | I9WS67_HELPX | Flagellar hook-associated protein 2 | *Helicobacter pylori* Hp P-11 | 677 | 97.0% | 3293 |
| J0PC82 | J0PC82_HELPX | Flagellar hook-associated protein | *Helicobacter pylori* Hp H-34 | 677 | 97.0% | 3292 |
| I9VJH4 | I9VJH4_HELPX | Flagellar hook-associated protein | *Helicobacter pylori* Hp H-21 | 677 | 97.0% | 3292 |
| J0PV65 | J0PV65_HELPX | Flagellar hook-associated protein 2 | *Helicobacter pylori* Hp P-8 | 677 | 97.0% | 3291 |
| I9YHM9 | I9YHM9_HELPX | Flagellar hook-associated protein 2 | *Helicobacter pylori* Hp P-8b | 677 | 97.0% | 3291 |
| J0TUW0 | J0TUW0_HELPX | Flagellar hook-associated protein 2 | *Helicobacter pylori* Hp P41 | 677 | 97.0% | 3289 |
| J0NSR5 | J0NSR5_HELPX | Flagellar hook-associated protein 2 | *Helicobacter pylori* Hp H-36 | 677 | 97.0% | 3289 |
| J0BAE3 | J0BAE3_HELPX | Flagellar hook-associated protein | *Helicobacter pylori* Hp H-36 | 677 | 97.0% | 3289 |
| J0LI78 | J0LI78_HELPX | Flagellar hook-associated protein 2 | *Helicobacter pylori* Hp H-41 | 677 | 96.0% | 3278 |
| E8QRV3 | E8QRV3_HELPW | Flagellar capping protein | *Helicobacter pylori* (strain SouthAfrica7) | 685 | 95.0% | 3264 |
| Q17Y06 | Q17Y06_HELAH | Flagellar hook-associated protein | *Helicobacter acinonychis* (strain Sheeba) | 685 | 94.0% | 3249 |
| K4NRS2 | K4NRS2_HELPY | Flagellar capping protein | *Helicobacter pylori* (strain ATCC 700392/26695) (*Campylobacter pylori*) | 674 | 97.0% | 3190 |
| K4NL36 | K4NL36_HELPX | Flagellar capping protein | *Helicobacter pylori* Rif2 | 674 | 97.0% | 3190 |
| K4NJJ9 | K4NJJ9_HELPX | Flagellar capping protein | *Helicobacter pylori* Rif1 | 674 | 97.0% | 3190 |
| M3QVV4 | M3QVV4_HELPX | Flagellar hook-associated protein 2 (Fragment) | *Helicobacter pylori* GAM71Ai | 647 | 97.0% | 3146 |
| I0ETW0 | I0ETW0_HELCM | Flagellar capping protein | *Helicobacter cetorum* (strain ATCC BAA-540/MIT 99-5656) | 685 | 88.0% | 3065 |
| I0EMR1 | I0EMR1_HELC0 | Flagellar capping protein | *Helicobacter cetorum* (strain ATCC BAA-429/MIT 00-7128) | 685 | 81.0% | 2861 |
| E7ADC3 | E7ADC3_HELFC | Flagellar hook-associated protein | *Helicobacter felis* (strain ATCC 49179/NCTC 12436/CS1) | 684 | 63.0% | 2190 |
| E7FYJ6 | E7FYJ6_9HELI | Flagellar capping protein | *Helicobacter suis* HS1 | 689 | 61.0% | 2158 |
| F8KTH3 | F8KTH3_HELBC | Flagellar hook-associated protein FliD | *Helicobacter bizzozeronii* (strain CIII-1) | 694 | 59.0% | 2091 |
| K4RHP3 | K4RHP3_HELHE | Flagellar hook-associated protein FliD | *Helicobacter heilmannii* ASB1.4 | 691 | 58.0% | 2073 |
| D3UGM5 | D3UGM5_HELM1 | Putative flagellar hook-associated protein | *Helicobacter mustelae* (strain ATCC 43772/LMG 18044/NCTC 12198/12198) (*Campylobacter mustelae*) | 674 | 52.0% | 1778 |
| Q7VI19 | Q7VI19_HELHP | Flagellar filament capping protein FliD | *Helicobacter hepaticus* (strain ATCC 51449/3B1) | 682 | 51.0% | 1698 |
| I2FDC5 | I2FDC5_HELCP | Flagellar capping protein | *Helicobacter cinaedi* (strain PAGU611) | 682 | 51.0% | 1690 |
| I7GZJ0 | I7GZJ0_9HELI | Flagellar capping protein | *Helicobacter cinaedi* ATCC BAA-847 | 682 | 51.0% | 1689 |
| E4VHL6 | E4VHL6_9HELI | Flagellar hook-protein 2 | *Helicobacter cinaedi* CCUG 18818 | 682 | 51.0% | 1689 |
| N2BQN7 | N2BQN7_9HELI | Uncharacterized protein | *Helicobacter bilis* WiWa | 679 | 45.0% | 1589 |
| C3XDT1 | C3XDT1_9HELI | Flagellar capping protein | *Helicobacter bilis* ATCC 43879 | 679 | 45.0% | 1583 |
| Q7MAM3 | Q7MAM3_WOLSU | FLAGELLAR HOOK-ASSOCIATED PROTEIN 2 | *Wolinella succinogenes* (strain ATCC 29543/DSM 1740/LMG 7466/NCTC 11488/FDC 602W) (*Vibrio succinogenes*) | 682 | 45.0% | 1479 |
| C5EXF0 | C5EXF0_9HELI | Flagellar hook-protein 2 | *Helicobacter pullorum* MIT 98-5489 | 685 | 39.0% | 1272 |
| C5ZWT4 | C5ZWT4_9HELI | Flagellar hook-associated protein (Flagellar hook-protein 2) | *Helicobacter canadensis* MIT 98-5491 | 689 | 39.0% | 1262 |

-continued

| Entry | Entry name | Protein names | Organism | Length | Identity | Score |
|---|---|---|---|---|---|---|
| H5VEC0 | H5VEC0_HELBI | Flagellar hook-associated protein FliD | *Helicobacter bizzozeronii* CCUG 35545 | 458 | 53.0% | 1185 |
| C3XLS4 | C3XLS4_9HELI | Flagellar hook-associated protein 2 | *Helicobacter winghamensis* ATCC BAA-430 | 689 | 37.0% | 1175 |
| H5VEC1 | H5VEC1_HELBI | Flagellar hook-associated protein FliD | *Helicobacter bizzozeronii* CCUG 35545 | 231 | 66.0% | 807 |
| H8CS11 | H8CS11_CAMJU | Flagellar capping protein | *Campylobacter jejuni* subsp. *jejuni* LMG 9872 | 645 | 27.0% | 474 |
| B9KGA6 | B9KGA6_CAMLR | Flagellar filament cap protein FliD | *Campylobacter lari* (strain RM2100/D67/ATCC BAA-1060) | 766 | 26.0% | 471 |
| C6RGG2 | C6RGG2_9PROT | SMR-type multidrug efflux transporter | *Campylobacter showae* RM3277 | 577 | 29.0% | 465 |
| D2MX77 | D2MX77_CAMJU | Flagellar hook-associated protein | *Campylobacter jejuni* subsp. *jejuni* 414 | 642 | 28.0% | 461 |
| M3I083 | M3I083_9PROT | Flagellar capping protein | *Campylobacter showae* CC57C | 577 | 28.0% | 457 |
| H7SA14 | H7SA14_CAMCO | Flagellar capping protein | *Campylobacter coli* 84-2 | 644 | 26.0% | 452 |
| D2MS44 | D2MS44_CAMJU | Flagellar hook-associated protein FliD | *Campylobacter jejuni* subsp. *jejuni* 1336 | 647 | 26.0% | 451 |
| H7XBH0 | H7XBH0_CAMJU | Flagellar capping protein | *Campylobacter jejuni* subsp. *jejuni* LMG 23216 | 648 | 26.0% | 451 |
| H7YRN9 | H7YRN9_CAMJU | Flagellar capping protein | *Campylobacter jejuni* subsp. *jejuni* LMG 23357 | 648 | 27.0% | 449 |
| Q30U48 | Q30U48_SULDN | Flagellar hook-associated protein 2-like protein | *Sulfurimonas denitrificans* (strain ATCC 33889/DSM 1251) (*Thiomicrospira denitrificans* (strain ATCC 33889/DSM 1251)) | 462 | 31.0% | 441 |
| H8BWB9 | H8BWB9_CAMJU | Flagellar capping protein | *Campylobacter jejuni* subsp. *jejuni* 1213 | 642 | 27.0% | 447 |
| H8AWN7 | H8AWN7_CAMJU | Flagellar capping protein | *Campylobacter jejuni* subsp. *jejuni* 1997-11 | 643 | 26.0% | 447 |
| A3ZDR2 | A3ZDR2_CAMJU | Flagellar hook-associated protein FliD | *Campylobacter jejuni* subsp. *jejuni* HB93-13 | 643 | 26.0% | 447 |
| A7H4J4 | A7H4J4_CAMJD | Flagellar hook-associated protein FliD | *Campylobacter jejuni* subsp. *doylei* (strain ATCC BAA-1458/RM4099/269.97) | 646 | 26.0% | 447 |
| A3YRI3 | A3YRI3_CAMJU | Flagellar hook-associated protein FliD | *Campylobacter jejuni* subsp. *jejuni* 260.94 | 642 | 25.0% | 442 |
| H7WEH0 | H7WEH0_CAMCO | Flagellar capping protein | *Campylobacter coli* H8 | 637 | 26.0% | 441 |
| E1PLQ8 | E1PLQ8_CAMJM | Flagellar hook-associated protein 2 | *Campylobacter jejuni* subsp. *jejuni* serotype HS21 (strain M1/99/308) | 643 | 27.0% | 441 |

EXAMPLE 9: PRESENCE AND EXPRESSION OF THE FLID IN *H. PYLORI*

Samples

81 *H. pylori* isolates from human patients were enrolled in the study. The samples were diagnosed as positive by conventional bacterial culture on selective plates. In such testing, bacteria were grown on Wilkins-Chalgren blood agar plates under microaerobic conditions (10% CO2, 5% O2, 8.5% N2, and 37° C.) for 36 hours, and positivity for oxidase, catalase and urease was confirmed by biochemical testing. A part of the cultured bacteria was used for DNA isolation and the remainder was applied for preparation of protein lysate for Western blot analysis.

Polyclonal Mouse Anti-FliD Sera

Three C57BL6 mice were immunized 3 times (weekly) with 30 µg of recombinant *H. pylori* FliD as antigen and 10 µg CT (cholera toxin) as adjuvant re-suspended in PBS. One week after the last immunization boost, mice were bleed and sera were pooled. The antigenicity and specificity of the pooled sera was tested in a Western blot analysis.

Western Blot Analysis

To establish the optimal conditions of the assay, different concentration of the recombinant FliD protein as well as other recombinant control proteins (Tig (Trigger factor (Tomb et al., 1997)) and gGT) generated and purified under the same conditions, were applied on 8% SDS gels. After blotting of the proteins on nitrocellulose membrane (Whatman/GE Healthcare, Freiburg, Germany), membranes were blocked in 5% non-fat milk for 1 h at room temperature and incubated overnight with different dilutions of the anti-sera as primary antibodies. After incubation of the membranes with HRP-labeled anti-mouse IgG, bands were detectable by adding of ECL Western Blotting Detection reagents.

Figure 5:
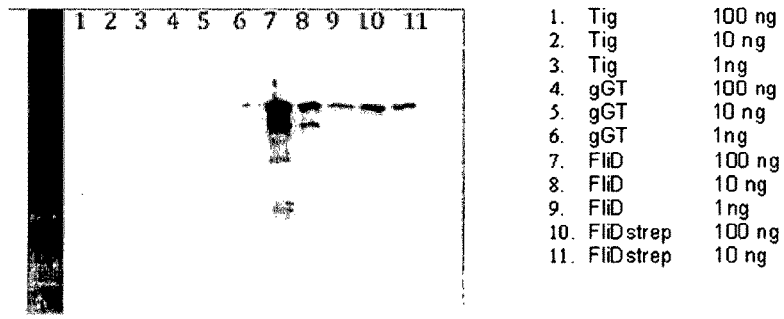
FIG. 5 shows the result of a Western blot analysis detecting FliD at various concentrations using mouse anti-FliD serum, but not Tig or gGT.

The results are shown in FIG. 5, whereby on the right side of the depicted SDS gel the antigen and its amount applied to the individual lanes is indicated. An optimal dilution (1:2000) of mouse anti serum was used.

PCR Analysis of the Presence of the FliD's ORF in *H. pylori*'s Genome

Four PCRs were designed based on the DNA sequence of the FliD as subject to SEQ ID NO: 2. Specificity of each primer pair as indicated in Table 5 was confirmed by blast analysis against all bacterial nucleotide sequences of the gene bank. PCRs were established using *H. pylori* DNA as positive control and genomic DNA of 10 other microorganisms as negative controls. PCRs were performed using GoTaq polymerase master mix (Promega), annealing temperature of 56° C. and 30 seconds extension time.

TABLE 5

Primers used for PCR analysis.

| | Forward primer | Reverse primer | Length of the amplicon (bp) |
|---|---|---|---|
| PCR1 | AGC TCA TTA GGG CTT GGC AG (SEQ ID NO: 21) | GCT CGC GCT CAA CGC ATC (SEQ ID NO: 22) | 246 |
| PCR2 | ATC ACG GAC GCT ACC AAT GG (SEQ ID NO: 23) | AGG GAC TTC ATG CAT GCT CC (SEQ ID NO: 24) | 288 |
| PCR3 | CAC AGA CGC TAT CAT TCA AGC (SEQ ID NO: 25) | CCC GCT GAT CAC ATC ATT GAC (SEQ ID NO: 26) | 300 |
| PCR4 | CGC TAA CCT CAT AGA TGG AGG (SEQ ID NO: 27) | TAA GCG GCA AAG CGC TCC G (SEQ ID NO: 28) | 150 |

Results

ORF of the FliD is presented in all *H. pylori* patient isolates (cultured bacteria isolated from patient biopsies). Presence of the ORF of the FliD could be confirmed by all four PCRs used for this assay. PCR1, PCR2 and PCR3 performed by isolated DNA from 81 *H. pylori* samples were overall positive. Whereas the PCR4 was positive for 79 samples (FIG. 6). Specificity of the assay was confirmed by applying DNA isolated from *P. aeruginosa* (ATCC 27813), *Klebsiella oxytoca* (ATCC 700324), *Candida albicans* (ATCC 90028), *Entrococcus faecalis* (ATCC 29292), Strep. Group A (ATCC 19615), *S. thyphimurium* (ATCC 13311), *S. aureus* (ATCC 25923), *S. epidermidis* (ATCC 18228), *H. influensae* (ATCC 49247) and *E. coli* (ATCC 25922).

As may be taken from FIG. 6 depicting the results of a representative PCR analysis performed using genomic DNA isolated from cultured *H. pylori* isolated from patient biopsies, FliD's ORF (open reading frame) is presented in almost all *H. pylori* isolates. Thus, PCR results confirm the presence of the FliD in genomic DNA. In FIG. 6, numbers above lanes indicate internal sample number.

As to the detection of FliD protein in samples from patients having been diagnosed as *H. pylori*-positive, FliD protein is detectable in 97.5% of the samples. Using Western blot analysis it could be demonstrated that the expression of the FliD protein is detectable in 79 out of 81 *H. pylori* protein lysates. The results are shown in FIG. 7. In FIG. 7 numbers above lanes indicate internal sample number.

The specificity of the assay was confirmed through negative results when protein lysates from other microorganisms were analyzed by Western blot analysis. The results thereof are indicated in FIG. 8. As may be taken from FIG. 8 apart from recombinant FliD with streptavidin tag (lanes 2 of both Western Blots) and without streptavidin tag (lanes 3 of both Western blots) protein lysates from *P. aeruginosa* (ATCC 27813) (left Western blot, lane 4), *Klebsiella oxytoca* (ATCC 700324) (left Western blot, lane 5), *Candida albicans* (ATCC 90024) (left Western blot, lane 6), *Enterococcus faecalis* (ATCC 29292) (left Western blot, lane 7), *Streptococcus* Group A (ATCC 19615) (left Western blot, lane 8), *S. thyphimurium* (ATCC 13311) (right Western blot, lane 4), *S. aureus* (ATCC 25923) (right Western blot, lane 5), *S. epidermidis* (ATCC 18228) (right Western blot, lane 6), *H. influensae* (ATCC 49247) (right Western blot, lane 7), and *E. coli* (ATCC 25922) (right Western blot, lane 8).

In the instant specification it is referred to various documents of the prior art the complete reference of which reads as follows and which are incorporated by reference.

Arnold, I. C., Hitzler, I., & Muller, A. (2012). The Immunomodulatory Properties of *Helicobacter pylori* Confer Protection Against Allergic and Chronic Inflammatory Disorders. Front Cell Infect Microbiol, 2, 10.

Atherton, J. C., Cao, P., Peek, R. M., Jr., Tummuru, M. K., Blaser, M. J., & Cover, T. L. (1995). Mosaicism in vacuolating cytotoxin alleles of *Helicobacter pylori*. Association of specific vacA types with cytotoxin production and peptic ulceration. J Biol Chem, 270(30), 17771-17777.

Chen, Y., Wang, J., & Shi, L. (2001). [In vitro study of the biological activities and immunogenicity of recombinant adhesin of *Heliobacter pylori* rHpaA]. Zhonghua Yi Xue Za Zhi, 81(5), 276-279.

Cover, T. L., & Blaser, M. J. (1992). Purification and characterization of the vacuolating toxin from *Helicobacter pylori*. J Biol Chem, 267(15), 10570-10575.

Dunn, B. E., Roop, R. M., 2nd, Sung, C. C., Sharma, S. A., Perez-Perez, G. I., & Blaser, M. J. (1992). Identification and purification of a cpn60 heat shock protein homolog from *Helicobacter pylori*. Infect Immun, 60(5), 1946-1951.

Eaton, K. A., Suerbaum, S., Josenhans, C., & Krakowka, S. (1996). Colonization of gnotobiotic piglets by *Helicobacter pylori* deficient in two flagellin genes. Infect Immun, 64(7), 2445-2448.

Franco, A. T., Israel, D. A., Washington, M. K., Krishna, U., Fox, J. G., Rogers, A. B., et al. (2005). Activation of beta-catenin by carcinogenic *Helicobacter pylori*. Proc Natl Acad Sci USA, 102(30), 10646-10651.

Fusconi, M., Vaira, D., Menegatti, M., Farinelli, S., Figura, N., Holton, J., et al. (1999). Anti-CagA reactivity in *Helicobacter pylori*-negative subjects: a comparison of three different methods. Dig Dis Sci, 44(8), 1691-1695.

Gao, L., Michel, A., Weck, M. N., Arndt, V., Pawlita, M., & Brenner, H. (2009). *Helicobacter pylori* infection and gastric cancer risk: evaluation of 15 *H. pylori* proteins determined by novel multiplex serology. Cancer Res, 69(15), 6164-6170.

Goto, T., Nishizono, A., Fujioka, T., Ikewaki, J., Mifune, K., & Nasu, M. (1999). Local secretory immunoglobulin A and postimmunization gastritis correlate with protection against *Helicobacter pylori* infection after oral vaccination of mice. Infect Immun, 67(5), 2531-2539.

Hay, F. C., Westwood, O. M. R., Nelson, P. N., & Hudson, L. (2002). Practical immunology: Wiley-Blackwell.

Honda, S., Fujioka, T., Tokieda, M., Satoh, R., Nishizono, A., & Nasu, M. (1998). Development of *Helicobacter* pylori-induced gastric carcinoma in Mongolian gerbils. Cancer Res, 58(19), 4255-4259.

Kim, J. S., Chang, J. H., Chung, S. I., & Yum, J. S. (1999). Molecular cloning and characterization of the *Helicobacter pylori* fliD gene, an essential factor in flagellar structure and motility. J Bacteriol, 181(22), 6969-6976.

Mittel P. R. E., Luethy L., Reinhardt C., Joller H. (2003). Detection of high titers of antibody against *Helicobacter* cysteine-rich proteins A, B, C, and E in *Helicobacter pylori*-infected individuals. Clin. Diagn. Lab. Immunol. 10:542-545.

Macchia, G., Massone, A., Burroni, D., Covacci, A., Censini, S., & Rappuoli, R. (1993). The Hsp60 protein of *Helicobacter pylori*: structure and immune response in patients with gastroduodenal diseases. Mol Microbiol, 9(3), 645-652.

Michetti, P., Kreiss, C., Kotloff, K. L., Porta, N., Blanco, J. L., Bachmann, D., et al. (1999). Oral immunization with urease and *Escherichia coli* heat-labile enterotoxin is safe and immunogenic in *Helicobacter pylori*-infected adults. Gastroenterology, 116(4), 804-812.

Montecucco, C., & de Bernard, M. (2003). Molecular and cellular mechanisms of action of the vacuolating cytotoxin (VacA) and neutrophil-activating protein (HP-NAP) virulence factors of *Helicobacter pylori*. Microbes Infect, 5(8), 715-721.

Murata-Kamiya, N., Kurashima, Y., Teishikata, Y., Yamahashi, Y., Saito, Y., Higashi, H., et al. (2007). *Helicobacter pylori* CagA interacts with E-cadherin and deregulates the beta-catenin signal that promotes intestinal transdifferentiation in gastric epithelial cells. Oncogene, 26(32), 4617-4626.

Oertli, M., Sundquist, M., Hitzler, I., Engler, D. B., Arnold, I. C., Reuter, S., et al. (2012). DC-derived IL-18 drives Treg differentiation, murine *Helicobacter pylori*-specific immune tolerance, and asthma protection. J Clin Invest, 122(3), 1082-1096.

Opazo, P., Muller, I., Rollan, A., Valenzuela, P., Yudelevich, A., Garcia-de la Guarda, R., et al. (1999). Serological response to *Helicobacter pylori* recombinant antigens in Chilean infected patients with duodenal ulcer, non-ulcer dyspepsia and gastric cancer. APMIS, 107(12), 1069-1078.

Pharmacia. (1988). Affinity chromatography LKB Biotechnology Uppsala, Sweden. Sambrook, J., Fritsch, E., & Maniatis, T. (1989). Molecular Cloning: A Laboratory Manuel, Book 1: New York: Cold Spring Harbor Laboratory Press.

Suerbaum, S., Thiberge, J. M., Kansau, I., Ferrero, R. L., & Labigne, A. (1994). *Helicobacter pylori* hspA-hspB heat-shock gene cluster: nucleotide sequence, expression, putative function and immunogenicity. Mol Microbiol, 14(5), 959-974.

Suganuma, M., Kurusu, M., Okabe, S., Sueoka, N., Yoshida, M., Wakatsuki, Y., et al. (2001). *Helicobacter pylori* membrane protein 1: a new carcinogenic factor of *Helicobacter pylori*. Cancer Res, 61(17), 6356-6359.

Tomb J. F., et al. 1997. The complete genome sequence of the gastric pathogen *Helicobacter pylori*. Nature, 7; 388 (6642):539-47.

Uemura, N., Okamoto, S., Yamamoto, S., Matsumura, N., Yamaguchi, S., Yamakido, M., et al. (2001). *Helicobacter pylori* infection and the development of gastric cancer. N Engl J Med, 345(11), 784-789.

Urita, Y., Hike, K., Torii, N., Kikuchi, Y., Kurakata, H., Kanda, E., et al. (2004). Comparison of serum IgA and IgG antibodies for detecting *Helicobacter pylori* infection. Intern Med, 43(7), 548-552.

Watanabe, S., Takagi, A., Tada, U., Kabir, A. M., Koga, Y., Kamiya, S., et al. (1997). Cytotoxicity and motility of *Helicobacter pylori*. J Clin Gastroenterol, 25 Suppl 1, S169-171.

Watanabe, T., Tada, M., Nagai, H., Sasaki, S., & Nakao, M. (1998). *Helicobacter pylori* infection induces gastric cancer in mongolian gerbils. Gastroenterology, 115(3), 642-648.

Yamaoka, Y., Kodama, T., Kita, M., Imanishi, J., Kashima, K., & Graham, D. Y. (1998). Relationship of vacA genotypes of *Helicobacter pylori* to cagA status, cytotoxin production, and clinical outcome. *Helicobacter*, 3(4), 241-253.

Yan, J., Liang, S. H., Mao, Y. F., Li, L. W., & Li, S. P. (2003). Construction of expression systems for flaA and flaB genes of *Helicobacter pylori* and determination of immunoreactivity and antigenicity of recombinant proteins. World J Gastroenterol, 9(10), 2240-2250.

Yan, J., & Mao, Y. F. (2004). Construction of a prokaryotic expression system of vacA gene and detection of vacA gene, VacA protein in *Helicobacter pylori* isolates and anti-VacA antibody in patients' sera. World J Gastroenterol, 10(7), 985-990.

The features of the present invention disclosed in the specification, the sequence listing, the claims and/or the drawings may both separately and in any combination thereof be material for realizing the invention in various forms thereof.

The invention claimed is:

1. A kit for detecting *H. pylori* infection in a subject, wherein detecting *H. pylori* infection comprises detecting in a sample from the subject an immune response against FliD, wherein the immune response comprises an anti-FliD antibody, wherein the kit comprises recombinant full-length FliD, wherein the recombinant full-length FliD is attached to a solid phase.

2. The kit of claim 1, further comprising one or more antigens selected from the group consisting of CagA, VacA, GroEL, Hp 0231, JHp 0940 and HtrA for detecting one or more antigens of *Helicobacter*.

3. The kit of claim 1, wherein the kit is configured to detect *H. pylori* infection in a sample is selected from the group consisting of blood serum, blood plasma, whole blood and stool.

4. The kit of claim 2, wherein the one or more antigens are of *H. pylori*.

5. The kit of claim 1, wherein the kit is configured to detect an anti-FliD antibody that is an IgG antibody, an IgA antibody, or an IgG antibody and an IgA antibody.

6. The kit of claim 1, configured for use in an ELISA, a lateral flow assay or a line assay.

7. The kit of claim 1, wherein the kit further comprises recombinant CagA.

8. The kit of claim 1, wherein FliD comprises an amino acid sequence selected from the group consisting of SEQ ID NO: 1, SEQ ID NO: 3, and SEQ ID NO: 5.

9. The kit of claim 7, wherein CagA comprises the amino acid sequence of SEQ ID NO: 7.

10. The kit of claim 1, wherein the kit is a ready-for-use kit.

11. The kit of claim 7, wherein the recombinant CagA is attached to the solid phase.

12. The kit of claim 1, wherein the kit further comprises a buffer and/or an instruction leaflet.

13. The kit of claim 1, wherein the recombinant full-length FliD further comprises a histidine tag.

14. The kit of claim 1, wherein the recombinant full-length FliD attached to the solid phase provides a sensitivity of more than 90% and a specificity of more than 90%.

15. The kit of claim 1, wherein the recombinant full-length FliD attached to the solid phase provides a sensitivity of up to 97.4% and a specificity of up to 99%.

16. The kit of claim 1, wherein the solid phase is selected from the group consisting of an ELISA plate, nitrocellulose and gold nanoparticles.

17. The kit of claim 1, wherein the solid phase comprises gold nanoparticles.

* * * * *

SEQUENCE LISTING

```
<160> NUMBER OF SEQ ID NOS: 28

<210> SEQ ID NO 1
<211> LENGTH: 685
<212> TYPE: PRT
<213> ORGANISM: H. pylori
<220> FEATURE:
<221> NAME/KEY: MISC_FEATURE
<223> OTHER INFORMATION: H. pylori strain G27

<400> SEQUENCE: 1

Met Ala Ile Gly Ser Leu Ser Ser Leu Gly Leu Gly Ser Lys Val Leu
1               5                   10                  15

Asn Tyr Asp Val Ile Asp Lys Leu Lys Asp Ala Asp Glu Lys Ala Leu
            20                  25                  30
```

```
Ile Ala Pro Leu Asp Lys Lys Met Glu Gln Asn Val Glu Lys Gln Lys
         35                  40                  45

Ala Leu Val Glu Ile Lys Thr Leu Leu Ser Ser Leu Lys Gly Pro Val
 50                  55                  60

Lys Thr Leu Ser Asp Tyr Ser Thr Tyr Ile Ser Arg Lys Ser Asn Val
 65                  70                  75                  80

Thr Gly Asp Ala Leu Ser Ala Ser Val Gly Ala Gly Val Pro Ile Gln
                 85                  90                  95

Asp Ile Lys Val Asp Val Gln Asn Leu Ala Gln Gly Asp Ile Asn Glu
                100                 105                 110

Leu Gly Ala Lys Phe Ser Ser Arg Asp Asp Ile Phe Ser Gln Val Asp
            115                 120                 125

Thr Thr Leu Lys Phe Tyr Thr Gln Asn Lys Asp Tyr Ala Val Asn Ile
        130                 135                 140

Lys Ala Gly Met Thr Leu Gly Asp Val Ala Gln Ser Ile Thr Asp Ala
145                 150                 155                 160

Thr Asn Gly Glu Val Met Gly Ile Val Met Lys Thr Gly Gly Asn Asp
                165                 170                 175

Pro Tyr Gln Leu Met Val Asn Thr Lys Asn Thr Gly Glu Asp Asn Arg
                180                 185                 190

Ile Tyr Phe Gly Ser His Leu Gln Ser Thr Leu Thr Asn Lys Asn Ala
            195                 200                 205

Leu Ser Leu Gly Val Asp Gly Ser Gly Lys Ser Glu Val Ser Leu Asn
        210                 215                 220

Leu Lys Gly Ala Asp Gly Asn Thr His Glu Val Pro Ile Met Leu Glu
225                 230                 235                 240

Leu Pro Glu Ser Ala Ser Ile Lys Gln Lys Asn Thr Ala Ile Gln Lys
                245                 250                 255

Ala Ile Glu Gln Ala Leu Glu Asn Asp Pro Asn Phe Lys Asp Leu Ile
            260                 265                 270

Ala Asn Gly Asp Ile Ser Ile Asp Thr Leu His Gly Gly Glu Ser Leu
        275                 280                 285

Ile Ile Asn Asp Arg Arg Gly Gly Asn Ile Glu Ile Lys Gly Ser Lys
290                 295                 300

Ala Lys Glu Leu Gly Phe Leu Gln Thr Thr Gln Glu Ser Asp Leu
                310                 315                 320

Leu Lys Ser Ser Arg Thr Ile Lys Glu Gly Lys Leu Glu Gly Val Ile
            325                 330                 335

Ser Leu Asn Gly Gln Lys Leu Asp Leu Lys Ala Leu Thr Lys Glu Gly
        340                 345                 350

Asn Thr Ser Glu Glu Asn Thr Asp Ala Ile Ile Gln Ala Ile Asn Ala
    355                 360                 365

Lys Glu Gly Leu Ser Ala Phe Lys Asn Ala Glu Gly Lys Leu Val Ile
370                 375                 380

Asn Ser Lys Thr Gly Met Leu Thr Ile Lys Gly Glu Asp Ala Leu Gly
385                 390                 395                 400

Lys Ala Ser Leu Lys Asp Leu Gly Leu Asn Ala Gly Met Val Gln Ser
                405                 410                 415

Tyr Glu Ala Ser Gln Asp Thr Leu Phe Met Ser Lys Asn Leu Gln Lys
            420                 425                 430

Ala Ser Asp Ser Gln Phe Thr Tyr Asn Gly Val Ser Ile Thr Arg Pro
        435                 440                 445
```

```
Thr Asn Glu Val Asn Asp Val Ile Asn Gly Val Asn Ile Thr Leu Glu
    450                 455                 460
Gln Thr Thr Glu Pro Asn Lys Pro Ala Ile Ile Ser Val Ser Arg Asp
465                 470                 475                 480
Asn Gln Ala Ile Ile Asp Ser Leu Lys Glu Phe Val Lys Ala Tyr Asn
                485                 490                 495
Glu Leu Ile Pro Lys Leu Asp Glu Asp Thr Arg Tyr Asp Ala Asp Thr
                500                 505                 510
Lys Ile Ala Gly Ile Phe Asn Gly Val Gly Asp Ile Arg Thr Ile Arg
                515                 520                 525
Ser Ser Leu Asn Asn Val Phe Ser Tyr Ser Val His Thr Asp Asn Gly
530                 535                 540
Val Glu Ser Leu Met Lys Tyr Gly Leu Ser Leu Asp Asp Lys Gly Val
545                 550                 555                 560
Met Ser Leu Asp Glu Ala Lys Leu Ser Ser Thr Leu Asn Ser Asn Pro
                565                 570                 575
Lys Ala Thr Gln Asp Phe Phe Tyr Gly Ser Asp Ser Lys Asp Met Gly
                580                 585                 590
Gly Arg Glu Ile His Gln Glu Gly Ile Phe Ser Lys Phe Asn Gln Val
                595                 600                 605
Ile Ala Asn Leu Ile Asp Gly Gly Asn Ala Lys Leu Lys Ile Tyr Glu
610                 615                 620
Asp Ser Leu Asp Arg Asp Ala Lys Ser Leu Thr Lys Asp Lys Glu Asn
625                 630                 635                 640
Ala Gln Glu Leu Leu Lys Thr Arg Tyr Asn Ile Met Ala Glu Arg Phe
                645                 650                 655
Ala Ala Tyr Asp Ser Gln Ile Ser Lys Ala Asn Gln Lys Phe Asn Ser
                660                 665                 670
Val Gln Met Met Ile Asp Gln Ala Ala Ala Lys Lys Asn
                675                 680                 685

<210> SEQ ID NO 2
<211> LENGTH: 2058
<212> TYPE: DNA
<213> ORGANISM: H. pylori
<220> FEATURE:
<221> NAME/KEY: misc_feature
<223> OTHER INFORMATION: H. pylori strain G27

<400> SEQUENCE: 2
atggcaatag gttcattaag ctcattaggg cttggcagta aggttttgaa ttacgatgtg      60
attgacaagc ttaaggacgc cgatgaaaaa gcgttaatcg ccccccttaga caagaaaatg     120 gagcaaaatg ttgaaaagca aaagccctt gtagaaatta aaacgctcct ttcatctcta      180
aaaggcccgg ttaaaacgct ttcggattat tccacttata tcagccgaaa aagcaatgtt     240
acaggcgatg cgttgagtgc gagtgtgggg gctggcgtgc ctattcaaga cattaaagtg     300
gatgtgcaaa atttagcgca aggcgatatt aacgaactag gggcgaaatt ttcttcaaga    360
gacgatattt ttagccaagt ggataccacg ctcaaatttt acacgcaaaa caaggactac     420
gccgttaata ttaaagcagg aatgacttta ggcgatgtgg ctcaaagcat cacgacgct     480 accaatggcg aagtgatggg cattgtgatg aaaacaggag ggaatgaccc ctaccaatta     540
atggtgaata ccaaaaacac cggcgaagac aaccgcatct attttggctc acacctccaa    600
tccacgctca ctaacaaaaa cgcccttct ttggggggttg atggaagcgg aaagagtgaa    660
gtgagtttga atttaaaggg ggctgatggg aacacgcatg aagtccccat catgctagag   720
```

```
ctccctgaaa gcgcttctat caaacaaaaa aacaccgcga tccaaaaagc gatagagcag    780
gctttagaaa acgaccctaa ttttaaagac ttgatcgcta atggggatat ttccatagac    840
actcttcatg gggggggaatc tttaatcatt aatgacaggc gtgggggaaa cattgaaatt    900
aaagggagca aggctaaaga gcttgggttt ttgcaaacca ccacccaaga aagcgatttg    960
ttaaaaagct ctcgcaccat taaagagggt aaattagaag gggtaattag cttgaatggc    1020
caaaaactgg atttaaaagc cttaaccaaa gagggcaaca ccagcgaaga aaacacagac    1080
gctatcattc aagcgattaa cgctaaagaa ggcttgagtg cgtttaaaaa cgccgaaggc    1140
aagcttgtga tcaattctaa accggaatg ctaacgatta agggcgagga cgctttaggc    1200
aaggccagtt tgaaggattt gggtttgaac gctggcatgg tgcaatctta tgaagcttca    1260
caagacacgc tttttatgtc taagaatttg caaaaagcga gcgattcgca attcacttat    1320
aatggggtga gcatcacacg ccccactaat gaggtcaatg atgtgattaa cggggttaat    1380
atcactttag agcaaaccac agagcctaat aaacctgcga ttatcagcgt gagcagggac    1440
aatcaagcca ttatagacag ccttaaagaa tttgtcaaag cctataatga gcttatccct    1500
aaactagatg aagacacgcg ttatgacgct gacactaaaa tcgctgggat ttttaacggc    1560
gtgggcgata ttcgcaccat tagatcctct cttaataacg tgttttctta tagcgtgcat    1620
acggataacg gggtagaaag cttgatgaaa tacgggctta gtttagacga taagggcgtg    1680
atgagtttag atgaggctaa attgagtagc accttaaatt ctaaccctaa agcgactcaa    1740
gattttttct atgggagcga tagcaaggat atggggggca gagaaatcca ccaagagggc    1800
atttttttcta aattcaatca agtcatcgct aatctcatag atggagggaa cgctaaatta    1860
aagatttatg aagattccct agacagagac gctaaaagct tgaccaaaga caaagaaaac    1920
gctcaagagc ttttaaaaac ccgctacaac atcatggcgg agcgctttgc ggcttatgac    1980
agccaaatct ctaaagccaa tcaaaaattc aattccgtgc aaatgatgat cgatcaagcg    2040
gcggctaaaa agaattaa                                                  2058
```

<210> SEQ ID NO 3
<211> LENGTH: 689
<212> TYPE: PRT
<213> ORGANISM: H. suis

<400> SEQUENCE: 3

Met Ala Ile Gly Lys Leu Ser Ser Leu Gly Ile Gly Ser Lys Val Leu
1               5                   10                  15

Asn Tyr Asp Val Ile Asp Lys Leu Lys Ser Ala Asp Glu Lys Thr Met
            20                  25                  30

Val Ala Pro Ile Asp Arg Lys Met Glu Val Asn Leu Glu Lys Gln Lys
        35                  40                  45

Ala Leu Val Glu Ile Lys Thr Leu Leu Ala Asn Leu Lys Ala Pro Val
    50                  55                  60

Ser Ala Leu Thr Asp Tyr Ser Thr Tyr Thr Ser Arg Ser Ser Ser Val
65                  70                  75                  80

Ser Ser Gly Ala Leu Lys Ala Ser Val Ser Pro Gly Ile Pro Val Gln
                85                  90                  95

Asp Ile Lys Val Glu Val Glu Asp Leu Ala Gln Gly Asp Ile Asn Glu
            100                 105                 110

Val Gly Thr His Phe Arg Asp Arg Asp Asp Ala Phe Ser Gln Ala Asn
        115                 120                 125

-continued

```
Thr Lys Leu His Phe Tyr Thr Asn Asn Lys Asn Tyr Thr Val Asn Ile
        130                 135                 140

Lys Ala Gly Met Ser Val Gly Asp Val Ala Gln Ala Ile Thr Asp Ala
145                 150                 155                 160

Thr Gly Gly Glu Val Met Gly Ile Val Met Lys Thr Gly Gly Asp Lys
                165                 170                 175

Pro Tyr Gln Leu Met Ile Asn Thr Lys Asn Pro Gly Ala Asn Asn Arg
            180                 185                 190

Leu Tyr Phe Gly Ser Ser Val Ile Ser Thr Leu Ala Ser Asp Ala Pro
        195                 200                 205

Ile Asn Leu Ala Ile Gly Gly Thr Thr Ala Asp Gly Lys Ser Thr Glu
210                 215                 220

Asp Asp Phe Phe Ile Lys Val Lys Asp Asp Lys Gly Glu Val Val Lys
225                 230                 235                 240

Ile Pro Ile Ser Leu Asn Leu Asp Lys Ala Ser Val Gln Asp Lys Asn
                245                 250                 255

Lys Ala Leu Gln Thr Ala Ile Lys Lys Ala Leu Glu Asp Asn Ala Gln
            260                 265                 270

Thr Lys Asp Leu Val Asp Ser Gly Gln Ile Asn Ile Gly Leu Ile Asn
        275                 280                 285

Asp Gly Lys Ser Leu Val Leu Asn Asp Gln Arg Gly Leu Glu Val Glu
290                 295                 300

Val Gly Gly Ala Lys Ala Ala Glu Leu Gly Phe Val Lys Thr Lys Ser
305                 310                 315                 320

Asp Gln Glu Asp Leu Leu Lys Gly Thr Ala Gly Ile Ala Ser Gly Gln
                325                 330                 335

Ile Lys Gly Thr Ile Asn Phe Asn Gly Gln Ala Ile Asn Leu Gly Ala
            340                 345                 350

Ile Thr Ala Thr Gly Asn Ser Ser Asp Ala Asn Ala Gln Ala Ile Val
        355                 360                 365

Lys Ala Ile Asn Gly Ile Gln Gly Leu His Ala Ser Leu Gly Thr Asp
370                 375                 380

Gly Lys Leu Ile Leu Asn Ser Glu Ser Gly Glu Leu Arg Ile Thr Gly
385                 390                 395                 400

Val Gly Ala Asp Gly Lys Ala Ala Val Asn Ser Leu Gly Leu Ser Glu
                405                 410                 415

Gly Leu Ser Gln Ser Tyr Ala Lys Leu His Asp Leu Phe Ala Phe Lys
            420                 425                 430

Lys Leu Gln Ser Ala Ser Asp Ala Arg Phe Thr Tyr Asn Gly Ala Thr
        435                 440                 445

Ile Thr Arg Pro Thr Asn Glu Val Asn Asp Val Ile Asn Gly Val Ser
450                 455                 460

Leu Ser Leu Leu Ala Lys Thr Glu Pro Gly Lys Pro Ala Ile Ile Ser
465                 470                 475                 480

Ile Thr Arg Asp Ser Lys Ala Ile Val Asp His Val Lys Glu Phe Val
                485                 490                 495

Lys Ala Tyr Asn Ala Leu Ile Pro Lys Leu Asp Glu Thr Thr Arg Tyr
            500                 505                 510

Asp Pro Asp Thr Lys Ile Ala Gly Val Phe Asn Gly Val Gly Asp Ile
        515                 520                 525

Arg Thr Ile Arg Ser Ser Ile Asn Asn Ala Ile Ala Phe Thr Ile Thr
530                 535                 540

Thr Ala Lys Gly Val Asp Ser Leu Met Lys Tyr Gly Ile Thr Leu Asp
```

```
                 545                 550                 555                 560
            Glu His Gly Lys Met Ser Leu Asp Glu Ser Arg Leu Thr Asn Ala Leu
                                 565                 570                 575

Asn Ala Asp Pro Gln Ala Ala Gln Asp Phe Phe Tyr Gly Gly Asp Ile
                             580                 585                 590

Lys Ser Met Gly Gly Lys Glu Ile His Gln Asp Gly Ile Phe Ile Lys
                         595                 600                 605

Leu Asp Lys Val Leu Gln Gly Leu Val Asp Gly Asn Ala Arg Leu
            610                 615                 620

Lys Leu Tyr Glu Asp Ser Leu Asp Gln Asp Ala Lys Asn Leu Arg Arg
            625                 630                 635                 640

Asp Lys Glu Asn Ala Met Glu Met Leu Lys Thr Arg Tyr Asp Met Met
                             645                 650                 655

Ala Glu Arg Phe Ala Ala Tyr Asp Glu Arg Ile Ser Lys Ala Asn Lys
                         660                 665                 670

Ser Phe Asp Ala Val Gln Met Met Ile Asp Gln Ala Ala Ala Lys Lys
                     675                 680                 685

Asn

<210> SEQ ID NO 4
<211> LENGTH: 2070
<212> TYPE: DNA
<213> ORGANISM: H. suis

<400> SEQUENCE: 4
atggcgattg aaagttaag ttctttaggg attgggagca aggttttaaa ctacgatgtg      60
attgataaac ttaaaagcgc tgatgaaaaa actatggtgg ctcccattga tcgaaaaatg     120
gaagtcaatc ttgaaaaaca aaaggcttta gttgagatta aactttgct tgccaatctt     180 aaagcgcccg ttagtgcttt aacggattat tcaacttata cgagccgcag tagcagtgtg     240
agcagtggag cgcttaaagc cagtgtaagc ccgggtatcc ctgtgcaaga tattaaagta     300
gaagttgagg atttggctca aggcgatatt aatgaagtcg gtacacattt tagagatcgc     360
gatgatgcct ttagccaagc taacaccaaa ttacactttt ataccaataa taaaaactac     420
acagtcaata ttaaggctgg tatgagtgta ggcgatgtcg cccaagccat tacagatgct     480
acggggggcg aggtgatggg gattgtgatg aaaaccgggg gggataaacc ctatcagtta     540
atgattaata ctaaaaaccc cggggctaat aaccgcttgt attttggctc tagtgttatt     600
tctactcttg ctagtgatgc gcctattaat ttagccatag ggggcactac tgcagatggg     660
aaaagtacag aagatgattt ttttattaaa gttaagatg ataagggcga agtggttaaa      720
atccctatta gtcttaatct tgataaggct tctgtgcaag ataaaaataa agccctgcaa     780
acagctatta aaaagcccct agaggataat gcacaaacca agacctagt agatagcgga     840 cagatcaata tcggtttgat taatgatggc aaatctttag tacttaacga tcaaagaggg     900
ttagaagttg aagttggggg agctaaagca gctgaactag ttttgttaa aactaaatca     960 gatcaagaag atttactcaa aggcacagca gggattgcat ccggtcaaat caagggcact    1020
attaatttta tgggcaagc cattaattta ggggctatca ccgcaacggg caattctagc    1080
gatgctaacg ctcaagccat cgttaaagcc attaatggca ttcaagggtt gcacgcttct    1140
ttaggcacgg acgggaaatt aatccttaat agtgaaagcg gcgagttgcg tataaccggt    1200 gtggggggccg atggtaaagc ggctgtaaat agtttaggtt tgtctgaggg cttaagccaa    1260
tcctatgcta aattacacga tctctttgcc tttaaaaaac tacaaagtgc ctctgatgct    1320
```

-continued

```
agatttactt acaatggtgc gacaatcacc cgccctacaa atgaggtaaa cgatgtgatt    1380
aacggtgtat ctttgagttt attagccaaa actgagccgg gtaaaccagc cattattagc    1440
attacccgcg acagtaaggc cattgttgat catgttaaag aatttgtcaa agcctataat    1500
gcattaatcc ctaaactaga tgaaacaacc cgttacgatc cagatactaa aattgccggc    1560
gtgtttaatg gcgtggggga tatccgcaca attcgctctt caattaataa tgccattgct    1620
tttacaatca caacggctaa aggtgtggat agtctcatga agtatgggat tacacttgat    1680
gagcatggaa agatgagctt agatgagagc agactcacaa acgcgcttaa tgccgatcca    1740
caagccgctc aagatttctt ctatggtggc gatattaaaa gtatgggggg taaggagatt    1800
caccaagacg ggattttat caagttagat aaagttttgc aaggtttggt cgatggtggt     1860
aacgcgaggt tgaagttata cgaggattct ttagatcaag acgctaaaaa tttgagaaga    1920
gataaggaga atgcaatgga gatgcttaaa acccgttatg acatgatggc agaacgcttt    1980
gcagcttatg atgagcgtat ttctaaggcg aataaatcct ttgatgcggt gcagatgatg    2040
atcgatcaag cagccgccaa aaagaattaa                                     2070
```

<210> SEQ ID NO 5
<211> LENGTH: 684
<212> TYPE: PRT
<213> ORGANISM: H. felis

<400> SEQUENCE: 5

```
Met Ala Val Gly Gln Leu Ser Ser Leu Gly Ile Gly Ser Lys Val Leu
1               5                   10                  15

Asn Tyr Asp Val Ile Asp Lys Leu Lys Lys Ala Asp Glu Asn Thr Met
            20                  25                  30

Val Lys Pro Ile Glu Arg Lys Met Glu Ala Asn Leu Gly Lys Gln Lys
        35                  40                  45

Ala Leu Val Glu Ile Gln Thr Leu Leu Gly Asn Leu Arg Thr Pro Val
    50                  55                  60

Arg Ala Leu Ser Asp Tyr Ser Thr Tyr Thr Ala Arg His Ser Asn Val
65                  70                  75                  80

Thr Gly Asp Ala Leu Lys Val Ser Val Ser Pro Gly Ile Pro Ile Gln
                85                  90                  95

Asn Ile Lys Val Asp Val Glu Ser Leu Ala Gln Gly Asp Ile Asn Glu
            100                 105                 110

Val Gly Thr His Phe Ser Ser Arg Asp Asp Ser Phe Ala Gln Phe Asp
        115                 120                 125

Thr Thr Leu His Phe Tyr Thr Asn His Gln Asp Tyr Ala Val Lys Ile
    130                 135                 140

Lys Ala Gly Met Thr Leu Ser Asp Val Ala Gln Ala Ile Thr Asp Ala
145                 150                 155                 160

Thr Asp Gly Lys Val Met Gly Ile Val Met Lys Thr Gly Gly Asn Lys
                165                 170                 175

Pro Tyr Gln Leu Met Ile Asn Ser Lys Gly Thr Gly Ala Asp Asn Arg
            180                 185                 190

Ile Phe Phe Gly Ser Ser Val Ile Ser His Leu Ser Asn Asp Ala Thr
        195                 200                 205

Ile Asn Leu Glu Ala Lys Ser Glu Thr Lys Pro Glu Asp Asp Phe Phe
    210                 215                 220

Ile Lys Val His Asp Glu Gln Asn Val Ile Glu Ile Pro Ile Ala Leu
225                 230                 235                 240
```

```
Lys Leu Gln Gly Ser Ile Glu Ser Lys Asn Ala Ala Leu Arg Ala Ala
                245                 250                 255

Ile Gln Lys Ala Leu Glu Asp Asn Pro Ala Thr Lys Ser Leu Ala Asp
            260                 265                 270

Asn Gly Gln Leu Asn Val Gly Val Ile Asn Glu Gly Lys Ser Leu Val
        275                 280                 285

Ile Asn Asp Lys Arg Gly Leu Ser Val Glu Val Gly Ala Lys Ala
    290                 295                 300

Arg Glu Leu Gly Phe Ile Gln Asp Lys Ser Gln Ala Glu Gly Asp Leu
305                 310                 315                 320

Leu Lys Ala Leu Thr Ala Pro Gln Ser Gly Lys Ile Lys Gly Ile Ile
                325                 330                 335

Ser Leu Asn Gly Gln Asn Ile Asp Met Gly Ala Ile Thr Ala Glu His
            340                 345                 350

Asn Ser Ser Gln Asp Asn Ala Asn Ala Leu Ile Lys Ala Val Asn Gly
        355                 360                 365

Ile Ala Gly Leu Ser Ala Ser Val Gly Ala Asp Gly Lys Leu Val Leu
    370                 375                 380

Asn Ser Ala Ser Gly Gln Leu Arg Leu Thr Gly Ala Asn Ala Glu Gly
385                 390                 395                 400

Lys Lys Ala Leu Lys Asp Leu Gly Leu Ser Glu Gly Phe Ser Arg Ser
                405                 410                 415

Tyr Ala Asn Ala Gln Glu Leu Phe Ser Val Lys Asn Leu Gln Ser Ala
            420                 425                 430

Ser Asp Ala Lys Phe Thr Tyr Asn Gly Ala Ser Ile Thr Arg Pro Thr
        435                 440                 445

Asn Glu Val Asn Asp Val Ile Asn Gly Val Ser Leu Ser Leu Leu Gly
    450                 455                 460

Thr Thr Glu Pro Gly Lys Gly Ala Val Val Ser Ile Thr Arg Asp Asp
465                 470                 475                 480

Lys Ala Ile Ile Asp Asn Val Lys Glu Phe Val Lys Ala Tyr Asn Glu
                485                 490                 495

Leu Met Pro Lys Leu Asp Glu Thr Thr Arg Tyr Asp Pro Asp Thr Arg
            500                 505                 510

Ile Ala Gly Ile Phe Asn Gly Val Ser Asp Ile Arg Thr Ile Arg Ser
        515                 520                 525

Ser Leu Ile Ser Ala Val Thr Phe Thr Ile Thr Asn Ser Lys Gly Val
    530                 535                 540

Ala Ser Leu Met Lys Tyr Gly Ile Met Leu Asp Asp His Gly Lys Met
545                 550                 555                 560

Ser Leu Asp Glu Ser Arg Leu Ala Ser Ala Ile Asn Ala Asp Pro Gln
                565                 570                 575

Gly Thr Gln Asp Phe Phe Tyr Gly Ser Asp Val Lys Ser Met Gly Gly
            580                 585                 590

Lys Glu Thr His Gln Asp Gly Ile Phe Glu Arg Val Asp Lys Val Leu
        595                 600                 605

Ala Asn Leu Val Asp Gly Gly His Ala Arg Leu Lys Leu Tyr Glu Asp
    610                 615                 620

Ser Leu Asp Gln Asp Ala Lys Ser Leu Lys Lys Asp Lys Glu Asn Ala
625                 630                 635                 640

Met Glu Leu Leu Lys Thr Arg Tyr Asp Ile Met Ala Glu Arg Phe Ala
                645                 650                 655
```

Ala Tyr Asp Glu Gln Ile Ser Lys Ala Asn Arg Ser Phe Asn Ala Val
        660                 665                 670

Gln Met Met Ile Asp Gln Ala Ala Ala Lys Lys Asn
        675                 680

<210> SEQ ID NO 6
<211> LENGTH: 2055
<212> TYPE: DNA
<213> ORGANISM: H. felis

<400> SEQUENCE: 6

| | | | | | |
|---|---|---|---|---|---|
| atggcagtag | ggcaattaag | ttctttggga | attggtagca | aagttttaaa | ctacgatgtg | 60 |
| atcgataagc | ttaaaaaagc | ggacgaaaac | acgatggtta | aacccatcga | gagaaagatg | 120 |
| gaggccaatt | tagaaaaaca | aaaagcccct | gtagaaatcc | aaactttgct | tgggaatttg | 180 |
| cgcacacctg | tcagagctct | aagcgattat | tccacttata | cagctagaca | tagcaatgta | 240 |
| accggggatg | cgcttaaagt | gagtgtgagt | ccgggtatcc | ccattcaaaa | tatcaaagtg | 300 |
| gatgtagaga | gtttagcaca | ggggatatt | aatgaggtgg | gcactcattt | tagctccaga | 360 |
| gacgactcgt | ttgcgcagtt | tgatactact | ttgcatttt | taccaatca | tcaggattac | 420 |
| gcggttaaaa | ttaagctgg | gatgacctta | agcgatgtcc | ctcaggcaat | cacgatgct | 480 |
| actgatggca | aggtgatggg | gattgtgatg | aaaaccgggg | ggaataaacc | ctatcagcta | 540 |
| atgatcaata | gtaagggcac | gggcgcggat | aatcgtatct | tttttggttc | tagtgtcatc | 600 |
| tcccatttga | gcaatgatgc | gaccattaat | ttagaagcca | agagcgagac | aaagcctgag | 660 |
| gatgattttt | ttatcaaagt | gcatgacgaa | caaaatgtga | tagaaattcc | tatcgctctc | 720 |
| aagttgcagg | gctctattga | gagtaaaaac | gcggctctgc | gtgcagccat | ccaaaaagcc | 780 |
| ttagaggata | atcccgctac | aaaatcttta | gcagacaatg | gcagttaaa | tgtggggtc | 840 |
| atcaatgagg | gtaaatcttt | ggtgatcaat | gataaacgag | gtttgagcgt | agaggtaggg | 900 |
| gggctaagc | cgcgcgaact | aggtttcatc | caagataaat | cccaagctga | gggtgattta | 960 |
| ctaaaagccc | tcaccgcccc | gcaatctggc | aagatcaaag | gcattattag | tctgaatgga | 1020 |
| caaaacattg | acatgggggc | gatcacagct | gaacataatt | ctagtcaaga | caacgctaac | 1080 |
| gctctgatta | agctgtcaa | tggcattgca | ggtttgagcg | cgtctgtggg | cgcggatggg | 1140 |
| aagttagtgc | tcaatagtgc | cagcgggcaa | ttacgcttaa | ccggagctaa | tgcagagggt | 1200 |
| aaaaaggctc | tcaaagattt | aggcctctca | gaggggttta | gccgctctta | tgctaatgct | 1260 |
| caagaactct | tttctgttaa | aaacttacag | agtgctagcg | atgctaaatt | tacctacaat | 1320 |
| ggggctagta | tcacgcgccc | taccaatgaa | gttaatgatg | taattaatgg | cgtgtctta | 1380 |
| agtttgctag | gcacaacaga | gccgggcaag | gggctgttg | tgagcatcac | acgagatgac | 1440 |
| aaggcgatca | tcgataatgt | caaagagttt | gtcaaagcct | ataatgagtt | gatgccaaaa | 1500 |
| ttagatgaga | ccacccgtta | cgatccggac | acaagaattg | ccgggatctt | taatggagtg | 1560 |
| agcgatatcc | gcactatccg | ctcttcactt | atcagtgcag | ttacttttac | aatcactaat | 1620 |
| agcaagggcg | tggctagctt | gatgaagtat | gggatcatgc | tagatgacca | tggcaagatg | 1680 |
| agtttagaca | aaagccgtct | tgctagcgca | atcaacgccg | atccgcaagg | cacccaagac | 1740 |
| ttcttttatg | gaagcgatgt | gaagagtatg | ggggcaagg | aaacccacca | agatggaatc | 1800 |
| tttgagcgcg | tggataaagt | tttggctaat | ttggtcgatg | gtggtcatgc | gcgtttgaag | 1860 |
| ctctatgaag | actctctaga | tcaagatgcc | aaaagcctca | aaaagataa | agagaacgct | 1920 |
| atggagttat | taaaaacccg | ctatgacatc | atggcagagc | gttttgctgc | ctatgacgag | 1980 |

```
cagatttcta aggctaaccg atcatttaac gctgtgcaga tgatgatcga tcaagctgct    2040
gctaagaaaa actaa                                                    2055
```

<210> SEQ ID NO 7
<211> LENGTH: 1230
<212> TYPE: PRT
<213> ORGANISM: H. pylori
<220> FEATURE:
<221> NAME/KEY: MISC_FEATURE
<223> OTHER INFORMATION: H. pylori strain G27

<400> SEQUENCE: 7

```
Met Thr Asn Glu Thr Ile Asn Gln Gln Pro Gln Thr Glu Ala Ala Phe
1               5                   10                  15

Asn Pro Gln Gln Phe Ile Asn Asn Leu Gln Val Ala Phe Leu Lys Val
            20                  25                  30

Asp Asn Ala Val Ala Ser Tyr Asp Pro Asp Gln Lys Pro Ile Val Asp
        35                  40                  45

Lys Asn Asp Arg Asp Asn Arg Gln Ala Phe Asn Gly Ile Ser Gln Leu
    50                  55                  60

Arg Glu Glu Tyr Ser Asn Lys Ala Ile Lys Asn Pro Ala Lys Lys Asn
65                  70                  75                  80

Gln Tyr Phe Ser Asp Phe Ile Asp Lys Ser Asn Asn Leu Ile Asn Lys
                85                  90                  95

Asp Ala Leu Ile Asp Val Glu Ser Ser Thr Lys Ser Phe Gln Lys Phe
            100                 105                 110

Gly Asp Gln Arg Tyr Gln Ile Phe Thr Ser Trp Val Ser His Gln Asn
        115                 120                 125

Asp Pro Ser Lys Ile Asn Thr Arg Ser Ile Arg Asn Phe Met Glu Asn
    130                 135                 140

Ile Ile Gln Pro Pro Ile Pro Asp Asp Lys Glu Lys Ala Glu Phe Leu
145                 150                 155                 160

Lys Ser Ala Lys Gln Ser Phe Ala Gly Ile Ile Ile Gly Asn Gln Ile
                165                 170                 175

Arg Thr Asp Gln Lys Phe Met Gly Val Phe Asp Glu Ser Leu Lys Glu
            180                 185                 190

Arg Gln Glu Ala Glu Lys Asn Gly Gly Pro Thr Gly Gly Asp Trp Leu
        195                 200                 205

Asp Ile Phe Leu Ser Phe Ile Phe Asp Lys Lys Gln Ser Ser Asp Val
    210                 215                 220

Lys Glu Ala Ile Asn Gln Glu Pro Val Pro His Val Gln Pro Asp Ile
225                 230                 235                 240

Ala Thr Thr Thr Thr Asp Ile Gln Gly Leu Pro Pro Glu Ala Arg Asp
                245                 250                 255

Leu Leu Asp Glu Arg Gly Asn Phe Ser Lys Phe Thr Leu Gly Asp Met
            260                 265                 270

Glu Met Leu Asp Val Glu Gly Val Ala Asp Ile Asp Pro Asn Tyr Lys
        275                 280                 285

Phe Asn Gln Leu Leu Ile His Asn Asn Ala Leu Ser Ser Val Leu Met
    290                 295                 300

Gly Ser His Asn Gly Ile Glu Pro Glu Lys Val Ser Leu Leu Tyr Gly
305                 310                 315                 320

Gly Asn Gly Gly Pro Lys Ala Lys His Asp Trp Asn Ala Thr Val Gly
                325                 330                 335
```

```
Tyr Lys Asp Gln Gln Gly Asn Asn Val Ala Thr Ile Ile Asn Val His
                340                 345                 350

Met Lys Asn Gly Ser Gly Leu Val Ile Ala Gly Gly Glu Lys Gly Ile
            355                 360                 365

Asn Asn Pro Ser Phe Tyr Leu Tyr Lys Glu Asp Gln Leu Thr Gly Ser
        370                 375                 380

Gln Arg Ala Leu Ser Gln Glu Glu Ile Arg Asn Lys Val Asp Phe Met
385                 390                 395                 400

Glu Phe Leu Ala Gln Asn Asn Ala Lys Leu Asp Asn Leu Ser Glu Lys
                405                 410                 415

Glu Glu Glu Lys Phe Arg Asn Glu Ile Lys Asp Phe Gln Lys Asp Ser
            420                 425                 430

Lys Ala Tyr Leu Asp Ala Leu Gly Asn Asp Arg Ile Ala Phe Val Ser
        435                 440                 445

Lys Lys Asp Thr Lys His Ser Ala Leu Ile Thr Glu Phe Gly Asn Gly
450                 455                 460

Asp Leu Ser Tyr Thr Leu Lys Asp Tyr Gly Lys Lys Ala Asp Lys Ala
                465                 470                 475                 480

Leu Asp Arg Glu Lys Asn Val Thr Leu Gln Gly Asn Leu Lys His Asp
            485                 490                 495

Gly Val Met Phe Val Asp Tyr Ser Asn Phe Lys Tyr Thr Asn Ala Ser
        500                 505                 510

Lys Asn Pro Asn Lys Gly Val Gly Val Thr Asn Gly Val Ser His Leu
        515                 520                 525

Glu Ala Gly Phe Ser Lys Val Ala Val Phe Asn Leu Pro Asp Leu Asn
        530                 535                 540

Asn Leu Ala Ile Thr Ser Leu Val Arg Arg Asp Leu Glu Asp Lys Leu
545                 550                 555                 560

Ile Ala Lys Gly Leu Ser Pro Gln Glu Thr Asn Lys Leu Val Lys Asp
                565                 570                 575

Phe Leu Ser Ser Asn Lys Glu Leu Val Gly Lys Ala Leu Asn Phe Asn
            580                 585                 590

Lys Ala Val Ala Glu Ala Lys Asn Thr Gly Asn Tyr Asp Glu Val Lys
        595                 600                 605

Gln Ala Gln Lys Asp Leu Glu Lys Ser Leu Lys Lys Arg Glu Arg Leu
        610                 615                 620

Glu Lys Glu Val Ala Lys Lys Leu Glu Ser Lys Ser Gly Asn Lys Asn
625                 630                 635                 640

Lys Met Glu Ala Lys Ser Gln Ala Asn Ser Gln Lys Asp Glu Ile Phe
                645                 650                 655

Ala Leu Ile Asn Lys Glu Ala Asn Arg Glu Ala Arg Ala Ile Thr Tyr
            660                 665                 670

Ala Gln Asn Leu Lys Gly Ile Lys Arg Glu Leu Ser Asp Lys Leu Glu
        675                 680                 685

Asn Val Asn Lys Asn Leu Lys Asp Phe Ser Lys Ser Phe Asp Glu Phe
        690                 695                 700

Lys Asn Gly Lys Asn Lys Asp Phe Ser Lys Ser Glu Thr Leu Lys
705                 710                 715                 720

Ala Leu Lys Gly Ser Val Lys Asp Leu Gly Ile Asn Pro Glu Trp Ile
                725                 730                 735

Ser Lys Val Glu Asn Leu Asn Ala Ala Leu Asn Glu Phe Lys Asn Gly
            740                 745                 750

Lys Asn Lys Asp Phe Ser Lys Val Thr Gln Ala Lys Ser Asp Leu Glu
```

```
              755                 760                 765
Asn Ser Val Lys Asp Val Ile Ile Asn Gln Lys Val Thr Asp Lys Val
770                 775                 780

Asp Asn Leu Asn Gln Ala Val Ser Val Ala Lys Ala Thr Gly Asp Phe
785                 790                 795                 800

Ser Arg Val Glu Gln Ala Leu Ala Asp Leu Lys Asn Phe Ser Lys Glu
                805                 810                 815

Gln Leu Ala Gln Gln Ala Gln Lys Asn Glu Asp Phe Asn Thr Gly Lys
            820                 825                 830

Asn Ser Ala Leu Tyr Gln Ser Val Lys Asn Gly Val Asn Gly Thr Leu
            835                 840                 845

Val Gly Asn Gly Leu Ser Lys Ala Glu Ala Thr Thr Leu Ser Lys Asn
850                 855                 860

Phe Ser Asp Ile Lys Lys Glu Leu Asn Ala Lys Leu Gly Asn Phe Asn
865                 870                 875                 880

Asn Asn Asn Asn Asn Gly Leu Lys Asn Ser Thr Glu Pro Ile Tyr Ala
                885                 890                 895

Lys Val Asn Lys Lys Ala Gly Gln Ala Ala Ser Pro Glu Glu Pro
            900                 905                 910

Ile Tyr Ala Gln Val Ala Lys Lys Val Asn Ala Lys Ile Asp Arg Leu
            915                 920                 925

Asn Gln Ile Ala Ser Gly Leu Gly Val Val Gly Gln Ala Val Gly Phe
930                 935                 940

Pro Leu Lys Arg His Asp Lys Val Gly Asp Leu Ser Lys Val Gly Gln
945                 950                 955                 960

Ser Val Ser Pro Glu Pro Ile Tyr Ala Thr Ile Asp Asp Leu Gly Gly
                965                 970                 975

Pro Phe Pro Leu Lys Arg His Asp Lys Val Gly Asp Leu Ser Lys Val
            980                 985                 990

Gly Leu Ser Val Ser Pro Glu Pro Ile Tyr Ala Thr Ile Asp Asp Leu
            995                 1000                1005

Gly Gly Pro Phe Pro Leu Lys Arg His Asp Lys Val Gly Asp Leu
         1010                1015                1020

Ser Lys Val Gly Leu Ser Arg Glu Gln Gln Leu Lys Gln Lys Ile
         1025                1030                1035

Asp Asn Leu Ser Gln Ala Val Ser Glu Ala Lys Ala Gly Phe Phe
         1040                1045                1050

Gly Asn Leu Glu Gln Thr Ile Asp Asn Leu Lys Asp Ser Ala Lys
         1055                1060                1065

Asn Asn Pro Val Ser Leu Trp Ala Glu Gly Ala Lys Lys Val Pro
         1070                1075                1080

Ala Ser Leu Ser Ala Lys Leu Asp Asn Tyr Ala Thr Asn Ser His
         1085                1090                1095

Thr Arg Ile Asn Ser Asn Ile Gln Ser Gly Ala Ile Asn Glu Lys
         1100                1105                1110

Ala Thr Gly Met Leu Thr Gln Lys Asn Pro Glu Trp Leu Lys Leu
         1115                1120                1125

Val Asn Asp Lys Ile Val Ala His Asn Val Gly Ser Val Pro Leu
         1130                1135                1140

Leu Glu Tyr Asp Lys Ile Gly Phe Asn Gln Lys Ser Met Lys Asp
         1145                1150                1155

Tyr Ser Asp Ser Phe Lys Phe Ser Thr Glu Leu Asn Asn Ala Val
         1160                1165                1170
```

Lys Asp Val Lys Ser Gly Phe Thr Gln Phe Leu Ala Asn Ala Phe
1175                1180                1185

Ser Thr Gly Tyr Tyr Arg Leu Ala Gly Glu Asn Ala Glu His Gly
1190                1195                1200

Ile Lys Asn Val Asn Thr Lys Gly Gly Ser Lys Asn Leu Lys Gly
    1205                1210                1215

Leu Arg Asn Thr Lys Asn Ala Lys Thr Thr Pro Cys
1220                1225                1230

<210> SEQ ID NO 8
<211> LENGTH: 3726
<212> TYPE: DNA
<213> ORGANISM: H. pylori
<220> FEATURE:
<221> NAME/KEY: misc_feature
<223> OTHER INFORMATION: H. pylori strain G27

<400> SEQUENCE: 8
aaggagaaac aatgactaac gaaactattg accaacaacc acaaaccgaa gcggctttta        60 accccgcagca atttatcaat aatcttcaag tagctttct taagcttgat aacgctgtcg      120
cttcatttga tcctgatcaa aaaccaatcg ttgataagaa cgatagggat aacaggcaag      180
cttttgatgg aatctcgcaa ttaagggaag aatactccaa taaagcgatc aaaaatccta      240
ccaaaaagaa tcagtatttt tcagacttta tcaataagag caatgattta atcaacaaag      300
acaatctcat tgatgtggaa tcttccacaa agagctttca gaaatttggg gatcagcgtt      360
accgaatttt cacaagttgg gtgtcccatc aaaacgatcc gtctaaaatc aacacccgat      420
cgatccgaaa ttttatggaa aatatcatac aacccctat ccatgatgac aaagaaaaag      480
cagagttttt gaaatctgcc aaacaatctt ttgcaggaat tatcataggg aatcaaatcc      540
gaacggatca aaagttcatg ggcgtgtttg atgaatcctt gaaagaaagg caagaagcag      600
aaaaaaatgg agagcctact ggtgggggatt ggttggatat tttttttatca tttatatttg      660 acaaaaaaca atcttctgat gtcaaagaag caatcaatca gaaccagtt cctcatgtcc      720 agccagatat agccactact accaccgaca tacaaggctt accgcctgaa tctagggatt      780
tgcttgatga aggggtaat ttttctaaat tcactcttgg cgatatggaa atgttagatg      840
ttgagggtgt cgctgacatt gatcctaatt acaagttcaa tcaattattg attcacaata      900
acgctctgtc ttctgtgtta atggggagtc ataatggcat agaacctgaa aaagtttcat      960
tattgtatgc gggcaatggt ggttttggag ccaagcacga ttggaacgcc accgttggtt     1020
ataaagacca acaaggtaac aatgtggcta caataattaa tgtgcatatg aaaaacggca     1080
gtggcttagt catagcaggt ggtgagaaag ggattaacaa ccctagtttt tatctctaca     1140
aagaagacca actcacaggc tcacaacgag cattgagtca agaagagatc cgaaacaaaa     1200
tagatttcat ggaatttctt gcacaaaaca atgctaaatt agacaacttg agcgagaaag     1260
agaaagaaaa attccgaaat gagattaagg atttccaaaa agactctaag gcttatttag     1320
acgccctagg gaatgatcgt attgcctttg tttctaaaaa agacccaaaa cattcagctt     1380
taattactga gttggtaag ggggatttga gctacactct caaagattat gggaaaaaag     1440
cagataaagc tttagatagg gagaaaaatg tcactcttca aggtaaccta aaacatgatg     1500
gcgtgatgtt tgttgattat tctaatttca aatacaccaa cgcctccaag aatcccaata     1560
agggtgtagc cgttacgaat ggcgtttccc atttagacgc aggctttagc aaggtagctg     1620 tcttttaattt gcctgattta aataatctcg ctatcactag tttcgtaagg cggaacttag     1680

-continued

```
aggataaact aattgctaaa ggattgaccc cacaagaagc taataagctt atcaaagatt    1740
ttttgagcag caacaaagaa ttggttggaa aagctttaaa cttcaataaa gctgtagctg    1800
acgctaaaaa cacaggcaac tatgacgagg tgaaaaaagc tcagaaagat cttgaaaaat    1860
ctctaaggaa acgagagcat ttagagaaag aagtagagaa aaaattggag agcaaaagcg    1920
gcaacaaaaa taaatggaa gcaaaagctc aagctaacag ccaaaaagat gagattttg     1980
cgttgatcaa taaagaggct aatagagacg caagagcaat cacttacgct caaaatctta   2040
aaggcatcaa aagggaattg tctgataaac ttgaaaatat caacaagaat ttgaaagact   2100
ttagtaaatc ttttgatgaa ttcaaaaatg caaaaataa ggatttcagc aaggcagaag    2160
aaacgctaaa agcccttaaa ggctcggtga agatttagg tatcaatccg gaatggattt    2220
caaaagttga aaaccttaat gcagctttga atgacttcaa aaatggcaaa ataaggatt    2280
tcagcaaggt aacgcaagca aaaagcgacc ttgaaaattc cgttaaagat gtgatcatca   2340
atcaaaagat aacggataaa gttgatgatc tcaatcaagc ggtatcagtg gctaaagcaa   2400
cgggtgattt cagtagggta gggcaagcgt tagccgatct caaaaatttc tcaaaggagc   2460
aattggctca acaaactcaa aaaaatgaaa gtttcaatgt tggaaaaaaa tctgaaatat   2520
atcaatccgt taagaatggt gtgaacggaa ccctagtcgg taatgggtta tctcaagcag   2580
aagccacaac tctttctaaa aacttttcgg acatcaagaa agagttgaat gcaaaacttt   2640
ttggaaattt caataacaat aacaataatg ggctcaaaaa cagcacagaa cccatttatg   2700
ctaaagttaa taaaagaaa acaggacaag tagctagccc tgaagaaccc atttatgctc    2760
aagttgctaa aaaggtaaat gcaaaaattg accaactcaa tcaagcagca gtggtttcg    2820
gtggtgtagg gcaagcagcg ggcttccctt tgaaaaggca tgataaagtt gatgatctca   2880
gtaaggtagg gcgatcggtt agccctgaac ccatttatgc tacaattgat gatctcggcg   2940
gaccttttccc tttgaaaagg catgataaag ttgatgatct cagtaaggta gggcgatcgg   3000
ttagccctga acccatttat gctacaattg atgatctcgg cggaccttttc cctttgaaaa   3060
ggcatgataa agttgatgat ctcagtaagg tagggctttc aagggagcaa caattgaaac   3120
agaagattga caagttcgat caagcggtat cagaagctaa agtaggttat tttggcaatc   3180
tagagcaaac gatagacaag ctcaaagatt ctgcaaaata caataccatg aatctatggg   3240
ctgaaagtgc aaaaaaagtg cctgctagtt tgtcagcgaa attggacaat tacgctacta   3300
acagccacac acgcattaat agcaatatcc aaaatggagc atcaatgaa aaagcgaccg    3360
gtatgctaac gcaaaaaaac cctgagtggc tcaagctcgt gaatgataag atcgttgcac   3420
ataatgtggg aagcgttcct tgtcagagt atgataaaat tggcttcaac cagaagaata    3480
tgaaagatta ttctgattcg ttcaagttt ccaccaagtt gaacaatgct gtaaaagaca    3540
ttaagtctgg cttttacgcaa ttttttagcca atgcattttc tacaggatat tactgcttgg   3600
cggggggaaaa tgcggagcat ggaatcaaaa atgttaatac aaaaggtggt ttccaaaaat   3660
cttaaaggat taaggaatac caaaaacgca aaaaccgccc cttgctaaaa gcaggggtt    3720
ttttaa                                                              3726
```

<210> SEQ ID NO 9
<211> LENGTH: 1294
<212> TYPE: PRT
<213> ORGANISM: H. pylori
<220> FEATURE:
<221> NAME/KEY: MISC_FEATURE
<223> OTHER INFORMATION: H. pylori strain G27

<400> SEQUENCE: 9

Met Glu Ile Gln Gln Thr His Arg Lys Met Asn Arg Pro Leu Val Ser
1               5                   10                  15

Leu Val Leu Ala Gly Ala Leu Ile Ser Ala Ile Pro Gln Glu Ser His
            20                  25                  30

Ala Ala Phe Phe Thr Thr Val Ile Pro Ala Ile Val Gly Gly Ile
        35                  40                  45

Ala Thr Gly Thr Ala Val Gly Thr Val Ser Gly Leu Leu Ser Trp Gly
    50                  55                  60

Leu Lys Gln Ala Glu Glu Ala Asn Lys Asn Pro Asp Lys Pro Asp Lys
65                  70                  75                  80

Val Trp Arg Ile Gln Ala Gly Lys Gly Phe Asn Glu Phe Pro Asn Lys
                85                  90                  95

Glu Tyr Asp Leu Tyr Lys Ser Leu Leu Ser Ser Lys Ile Asp Gly Gly
            100                 105                 110

Trp Asp Trp Gly Asn Ala Ala Arg His Tyr Trp Val Lys Gly Gly Gln
        115                 120                 125

Trp Asn Lys Leu Glu Val Asp Met Lys Asp Ala Val Gly Thr Tyr Lys
130                 135                 140

Leu Ser Gly Leu Arg Asn Phe Thr Gly Gly Asp Leu Asp Val Asn Met
145                 150                 155                 160

Gln Lys Ala Thr Leu Arg Leu Gly Gln Phe Asn Gly Asn Ser Phe Thr
                165                 170                 175

Ser Tyr Lys Asp Ala Ala Asp Arg Thr Thr Arg Val Asn Phe Asn Ala
            180                 185                 190

Lys Asn Ile Ser Ile Asp Asn Phe Val Glu Ile Asn Asn Arg Val Gly
        195                 200                 205

Ser Gly Ala Gly Arg Lys Ala Ser Ser Thr Val Leu Thr Leu Gln Ala
    210                 215                 220

Ser Glu Gly Ile Thr Ser Asp Lys Asn Ala Glu Ile Ser Leu Tyr Asp
225                 230                 235                 240

Gly Ala Thr Leu Asn Leu Ala Ser Ser Ser Val Lys Leu Met Gly Asn
                245                 250                 255

Val Trp Met Gly Arg Leu Gln Tyr Val Gly Ala Tyr Leu Ala Pro Ser
            260                 265                 270

Tyr Ser Thr Ile Asn Thr Ser Lys Val Thr Gly Glu Val Asn Phe Asn
        275                 280                 285

His Leu Thr Val Gly Asp Lys Asn Ala Ala Gln Ala Gly Ile Ile Ala
    290                 295                 300

Ser Asn Lys Thr His Ile Gly Thr Leu Asp Leu Trp Gln Ser Ala Gly
305                 310                 315                 320

Leu Asn Ile Ile Ala Pro Pro Glu Gly Gly Tyr Lys Asp Lys Pro Asn
                325                 330                 335

Asn Thr Pro Ser Gln Ser Gly Thr Lys Asn Asp Lys Asn Glu Ser Ala
            340                 345                 350

Lys Asn Asp Lys Gln Glu Ser Ser Gln Asn Asn Ser Asn Thr Gln Val
        355                 360                 365

Ile Asn Pro Pro Asn Ser Thr Gln Lys Thr Glu Ile Gln Pro Thr Gln
    370                 375                 380

Val Ile Asp Gly Pro Phe Ala Gly Gly Lys Asp Thr Val Val Asn Ile
385                 390                 395                 400

Asn Arg Ile Asn Thr Asn Ala Asp Gly Thr Ile Arg Val Gly Gly Phe

```
                    405                 410                 415
Lys Ala Ser Leu Thr Thr Asn Ala Ala His Leu His Ile Gly Lys Gly
            420                 425                 430

Gly Val Asn Leu Ser Asn Gln Ala Ser Gly Arg Thr Leu Leu Val Glu
            435                 440                 445

Asn Leu Thr Gly Asn Ile Thr Val Asp Gly Pro Leu Arg Val Asn Asn
    450                 455                 460

Gln Val Gly Gly Tyr Ala Leu Ala Gly Ser Ser Ala Asn Phe Glu Phe
465                 470                 475                 480

Lys Ala Gly Val Asp Thr Lys Asn Gly Thr Ala Thr Phe Asn Asn Asp
                485                 490                 495

Ile Ser Leu Gly Arg Phe Val Asn Leu Lys Val Asp Ala His Thr Ala
                500                 505                 510

Asn Phe Lys Gly Ile Asp Thr Gly Asn Gly Gly Phe Asn Thr Leu Asp
            515                 520                 525

Phe Ser Gly Val Thr Asp Lys Val Asn Ile Asn Lys Leu Ile Thr Ala
        530                 535                 540

Ser Thr Asn Val Ala Val Lys Asn Phe Asn Ile Asn Glu Leu Ile Val
545                 550                 555                 560

Lys Thr Asn Gly Ile Ser Val Gly Glu Tyr Thr His Phe Ser Glu Asp
                    565                 570                 575

Ile Gly Ser Gln Ser Arg Ile Asn Thr Val Arg Leu Glu Thr Gly Thr
                580                 585                 590

Arg Ser Ile Phe Ser Gly Gly Val Lys Phe Lys Ser Gly Glu Lys Leu
                595                 600                 605

Val Ile Asp Glu Phe Tyr Tyr Ser Pro Trp Asn Tyr Phe Asp Ala Arg
    610                 615                 620

Asn Val Lys Asn Val Glu Ile Thr Arg Lys Phe Ala Ser Ser Thr Pro
625                 630                 635                 640

Glu Asn Pro Trp Gly Thr Ser Lys Leu Met Phe Asn Asn Leu Thr Leu
                645                 650                 655

Gly Gln Asn Ala Val Met Asp Tyr Ser Gln Phe Ser Asn Leu Thr Ile
                660                 665                 670

Gln Gly Asp Phe Ile Asn Asn Gln Gly Thr Ile Asn Tyr Leu Val Arg
            675                 680                 685

Gly Gly Lys Val Ala Thr Leu Ser Val Gly Asn Ala Ala Ala Met Met
        690                 695                 700

Phe Asn Asn Asp Ile Asp Ser Ala Thr Gly Phe Tyr Lys Pro Leu Ile
705                 710                 715                 720

Lys Ile Asn Ser Ala Gln Asp Leu Ile Lys Asn Thr Glu His Val Leu
                725                 730                 735

Leu Lys Ala Lys Ile Ile Gly Tyr Gly Asn Val Ser Thr Gly Thr Asn
                740                 745                 750

Ser Ile Ser Asn Val Asn Leu Glu Glu Gln Phe Lys Glu Arg Leu Ala
            755                 760                 765

Leu Tyr Asn Asn Asn Asn Arg Met Asp Thr Cys Val Val Arg Asn Thr
    770                 775                 780

Asp Asp Ile Lys Ala Cys Gly Met Ala Ile Gly Asn Gln Ser Met Val
785                 790                 795                 800

Asn Asn Pro Asp Asn Tyr Lys Tyr Leu Ile Gly Lys Ala Trp Lys Asn
                805                 810                 815

Ile Gly Ile Ser Lys Thr Ala Asn Gly Ser Lys Ile Ser Val Tyr Tyr
            820                 825                 830
```

```
Leu Gly Asn Ser Thr Pro Thr Glu Asn Gly Gly Asn Thr Thr Asn Leu
        835                 840                 845

Pro Thr Asn Thr Thr Asn Asn Ala Arg Ser Ala Asn Tyr Ala Leu Val
    850                 855                 860

Lys Asn Ala Pro Phe Ala His Ser Ala Thr Pro Asn Leu Val Ala Ile
865                 870                 875                 880

Asn Gln His Asp Phe Gly Thr Ile Glu Ser Val Phe Glu Leu Ala Asn
                885                 890                 895

Arg Ser Lys Asp Ile Asp Thr Leu Tyr Thr His Ser Gly Val Gln Gly
                900                 905                 910

Arg Asp Leu Leu Gln Thr Leu Leu Ile Asp Ser His Asp Ala Gly Tyr
                915                 920                 925

Ala Arg Gln Met Ile Asp Asn Thr Ser Thr Gly Glu Ile Thr Lys Gln
    930                 935                 940

Leu Asn Ala Ala Thr Asp Ala Leu Asn Asn Ile Ala Ser Leu Glu His
945                 950                 955                 960

Lys Thr Ser Gly Leu Gln Thr Leu Ser Leu Ser Asn Ala Met Ile Leu
                965                 970                 975

Asn Ser Arg Leu Val Asn Leu Ser Arg Lys His Thr Asn His Ile Asp
                980                 985                 990

Ser Phe Ala Gln Arg Leu Gln Ala Leu Lys Gly Gln Arg Phe Ala Ser
            995                1000                1005

Leu Glu Ser Ala Ala Glu Val Leu Tyr Gln Phe Ala Pro Lys Tyr
        1010                1015                1020

Glu Lys Pro Thr Asn Val Trp Ala Asn Ala Ile Gly Gly Ala Ser
        1025                1030                1035

Leu Asn Asn Gly Gly Asn Ala Ser Leu Tyr Gly Thr Ser Ala Gly
        1040                1045                1050

Val Asp Ala Tyr Leu Asn Gly Glu Val Glu Ala Ile Val Gly Gly
        1055                1060                1065

Phe Gly Ser Tyr Gly Tyr Ser Ser Phe Ser Asn Arg Ala Asn Ser
        1070                1075                1080

Leu Asn Ser Gly Ala Asn Asn Ala Asn Phe Gly Val Tyr Ser Arg
        1085                1090                1095

Ile Phe Ala Asn Gln His Glu Phe Asp Phe Glu Ala Gln Gly Ala
        1100                1105                1110

Leu Gly Ser Asp Gln Ser Ser Leu Asn Phe Lys Ser Ala Leu Leu
        1115                1120                1125

Gln Asp Leu Asn Gln Ser Tyr His Tyr Leu Ala Tyr Ser Ala Ala
        1130                1135                1140

Thr Arg Ala Ser Tyr Gly Tyr Asp Phe Ala Phe Arg Asn Ala
        1145                1150                1155

Leu Val Leu Lys Pro Ser Val Gly Val Ser Tyr Asn His Leu Gly
        1160                1165                1170

Ser Thr Asn Phe Lys Ser Ser Asn Gln Val Ala Leu Lys Asn
        1175                1180                1185

Gly Ser Ser Ser Gln His Leu Phe Asn Ala Asn Ala Asn Val Glu
        1190                1195                1200

Ala Arg Tyr Tyr Tyr Gly Asp Thr Ser Tyr Phe Tyr Met Asn Ala
        1205                1210                1215

Gly Val Leu Gln Glu Phe Ala Arg Phe Gly Ser Asn Asn Ala Ala
        1220                1225                1230
```

| | | | | | | | | | | |
|---|---|---|---|---|---|---|---|---|---|---|
|Ser|Leu|Asn|Thr|Phe|Lys|Val|Asn|Thr|Ala|Arg|Asn|Pro|Leu|Asn|
| |1235| | | |1240| | | |1245| |

Thr His Ala Arg Val Met Met Gly Gly Glu Leu Gln Leu Ala Lys
    1250                1255                1260

Glu Val Phe Leu Asn Leu Gly Val Val Tyr Leu His Asn Leu Ile
    1265                1270                1275

Ser Asn Ile Gly His Phe Ala Ser Asn Leu Gly Met Arg Tyr Ser
    1280                1285                1290

Phe

<210> SEQ ID NO 10
<211> LENGTH: 3885
<212> TYPE: DNA
<213> ORGANISM: H. pylori
<220> FEATURE:
<221> NAME/KEY: misc_feature
<223> OTHER INFORMATION: H. pylori strain G27

<400> SEQUENCE: 10

```
atggaaatac aacaaacaca ccgcaaaatg aatcgccctt tagtttctct cgttttagca      60
ggagcgttaa ttagcgccat accgcaagaa agtcatgccg ccttttttcac gaccgtgatc    120
attccagcca ttgttggggg tatcgccaca ggcaccgctg taggaacggt ctcagggctt    180
cttagctggg ggctcaaaca agccgaagaa gcgaataaaa acccggacaa acccgataaa    240
gtttggcgca ttcaagcagg aaaaggcttt aatgaattcc ctaacaagga atacgactta    300
tacaaatccc ttttatccag taagattgat ggaggttggg actgggggaa cgccgctagg    360
cattattggg tcaaaggcgg gcaatggaac aagcttgaag tggatatgaa agacgctgta    420
gggacttata aactatcagg gcttagaaac tttactggtg gggatttaga tgtcaatatg    480
caaaaagcca ctttacgctt gggccaattc aatggcaatt ctttcacaag ctataaggat    540
gcggctgatc gcaccacgag ggtgaatttc aacgctaaaa atatctcaat tgataatttt    600
gtagaaatca ataatcgtgt gggttctgga gccggagga aagccagctc tacggttttg    660
actttgcaag cttcagaagg gatcactagc gataaaaacg ctgaaatttc tctttatgat    720
ggcgccacgc tcaatttggc ttcaagcagc gttaaattaa tgggtaatgt gtggatgggc    780
cgtttgcaat acgtgggagc gtatttggcc ccttcataca gcacgataaa cacttcaaaa    840
gtaacagggg aagtgaattt taaccacctc actgttggcg ataaaaacgc cgctcaagcg    900
ggcattatcg ctagcaacaa gactcatatt ggcacactgg atttgtggca aagcgccggg    960
ttaaacatta tcgctcctcc cgaaggtggc tataaggata aacctaataa tacccccttct   1020
caaagtggca ctaaaaacga caaaaatgaa agcgctaaaa acgacaaaca agagagcagt   1080
caaaataata gtaacactca ggtcattaac ccacccaata gcacgcaaaa aacagaaatt   1140
caacccacgc aagtcattga tgggccttttt gcggcggca agacacggt tgtcaatatc    1200
aaccgcatca acactaacgc tgatggcacg attagagtgg gagggtttaa agcttctctt   1260
accaccaatg cggctcattt gcatatcggc aaaggcggtg tcaatctgtc caatcaagcg    1320
agcgggcgca ccctttttagt ggaaaatcta accgggaata tcaccgttga tgggccttta   1380
agagtgaata atcaagtggg tggctatgct ttggcaggat caagcgcgaa tttttgaattt   1440
aaggctggtg tggatactaa aaacggcaca gccactttca ataacgatat tagcctggga    1500
agatttgtga atttaaaggt ggatgctcat acagctaatt ttaaaggtat tgatacgggt   1560
aatggtggtt tcaacaccct tagattttagt ggtgttacag acaaagtcaa tatcaacaag   1620
```

```
ctcatcacgg cttccactaa tgtggccgtt aaaaacttca acattaatga attgattgtt    1680
aaaaccaatg ggataagtgt gggggaatac actcatttta gcgaagatat aggcagtcaa    1740
tcgcgcatca ataccgtgcg tttggaaact ggcactaggt caatcttttc tggggtgtc     1800
aaatttaaaa gcggcgaaaa attggttata gatgagtttt actatagccc ttggaattat    1860
tttgacgcta ggaatgttaa aaatgttgaa atcaccagaa aattcgcttc ttcaaccca     1920
gaaacccctt gggcacatc aaaacttatg tttaataatc taaccctggg tcaaaatgcg     1980
gtcatggact atagtcaatt ttcaaattta accatccaag gggattttat caacaatcaa    2040
ggcactatca actatctggt ccgaggcggg aaagtggcaa ccttaagcgt aggcaatgca    2100
gcagctatga tgtttaataa tgatatagac agcgcgaccg gattttacaa accgctcatc    2160
aagattaaca gtgctcaaga tctcattaaa aatacagagc atgttttatt gaaagcgaaa    2220
atcattggtt atggtaatgt ttctacaggt accaatagca ttagtaatgt taatctagaa    2280
gagcaattca aagagcgcct agccctttat aacaacaata accgcatgga tacttgtgtg    2340
gtgcgaaata ctgatgacat taaagcatgc ggtatggcta tcggcaatca aagcatggtg    2400
aataaccctg acaattacaa gtatcttatc ggtaaggcat ggaaaaatat aggcatcagt    2460
aaaacggcta acggctctaa aatttcggtg tattatttag gcaattctac gcctactgag    2520
aatggtggca ataccaccaa cttacccacc aacaccacta ataatgcgcg ttctgctaac    2580
tacgccctcg tgaagaacgc tcctttcgct cacagtgcca ctcctaattt agtcgctatc    2640
aatcagcatg attttggcac tattgaaagc gtgtttgaat tggctaaccg ctctaaagat    2700
attgacacgc tttatactca ttcaggcgtg caaggtaggg atctcttaca aaccttattg    2760
attgatagcc atgatgcggg ttatgccaga caaatgattg ataacacaag caccggtgaa    2820
atcaccaaac aattgaatgc ggccactgac gctttaaaca acatagccag tttagagcat    2880
aaaccagcg gcttgcaaac tttgagcttg agtaatgcga tgattttaaa ttctcgttta    2940
gtcaatctct ccaggaagca caccaaccat attgactcgt tcgctcaacg cttacaagct    3000
ttaaaaggcc aaagattcgc ttctttagag agcgcggcag aagtgttgta tcaatttgcc    3060
cctaaatatg aaaaacctac caatgtttgg gctaacgcta ttgggggagc gagcttgaat    3120
aatggcggca acgcttcatt gtatggcaca agtgccggtg tagacgctta ccttaatggg    3180
gaagtggaag ccattgtggg cgggtttgga agctatggtt atagctcttt tagtaatcgt    3240
gcgaactctc ttaactctgg ggctaataac gctaattttg gcgtgtatag ccgtatttt     3300
gctaaccagc atgaatttga ttttgaagct caaggggcgc tagggagtga tcaatcaagc    3360
ttgaatttca aaagtgctct actgcaagat ttgaatcaaa gctatcatta tttagcctat    3420
agcgctgcaa caagagcgag ctatggttat gactttgcgt ttttcaggaa cgctttagtg    3480
ttaaaaccaa gcgtgggcgt gagctataac catttaggtt caaccaactt taaaagcagc    3540
agcaatcaag tggcttttga aaatggctct agcagtcagc atctattcaa cgctaacgct    3600
aatgtggaag cgcgctatta ttatgggac acttcatact tctatatgaa cgctggagtt    3660
ttacaagagt tcgctcgctt tggatctaat aacgccgcgt cttttaacac ctttaaagtg    3720
aataccgctc gcaaccettt aaataceccat gccagagtga tgatgggtgg ggaattgcaa   3780
ttagctaaag aagtgttttt gaatttgggc gttgtttatt tgcacaattt gatttccaat    3840
ataggccatt tcgcttccaa tttaggaatg aggtatagtt tctaa                    3885

<210> SEQ ID NO 11
<211> LENGTH: 546
```

```
<212> TYPE: PRT
<213> ORGANISM: H. pylori
<220> FEATURE:
<221> NAME/KEY: MISC_FEATURE
<223> OTHER INFORMATION: H. pylori strain G27

<400> SEQUENCE: 11
```

| Met | Ala | Lys | Glu | Ile | Lys | Phe | Ser | Asp | Ser | Ala | Arg | Asn | Leu | Leu | Phe |
|---|---|---|---|---|---|---|---|---|---|---|---|---|---|---|---|
| 1 | | | | 5 | | | | | 10 | | | | | 15 | |

| Glu | Gly | Val | Arg | Gln | Leu | His | Asp | Ala | Val | Lys | Val | Thr | Met | Gly | Pro |
|---|---|---|---|---|---|---|---|---|---|---|---|---|---|---|---|
| | | | 20 | | | | 25 | | | | | 30 | | | |

| Arg | Gly | Arg | Asn | Val | Leu | Ile | Gln | Lys | Ser | Tyr | Gly | Ala | Pro | Ser | Ile |
|---|---|---|---|---|---|---|---|---|---|---|---|---|---|---|---|
| | | 35 | | | | | 40 | | | | | 45 | | | |

| Thr | Lys | Asp | Gly | Val | Ser | Val | Ala | Lys | Glu | Ile | Glu | Leu | Ser | Cys | Pro |
|---|---|---|---|---|---|---|---|---|---|---|---|---|---|---|---|
| 50 | | | | | 55 | | | | | 60 | | | | | |

| Val | Ala | Asn | Met | Gly | Ala | Gln | Leu | Val | Lys | Val | Ala | Ser | Lys | Thr |
|---|---|---|---|---|---|---|---|---|---|---|---|---|---|---|
| 65 | | | | 70 | | | | | 75 | | | | | 80 |

| Ala | Asp | Ala | Ala | Gly | Asp | Gly | Thr | Thr | Thr | Ala | Thr | Val | Leu | Ala | Tyr |
|---|---|---|---|---|---|---|---|---|---|---|---|---|---|---|---|
| | | | | 85 | | | | | 90 | | | | | 95 | |

| Ser | Ile | Phe | Lys | Glu | Gly | Leu | Arg | Asn | Ile | Thr | Ala | Gly | Ala | Asn | Pro |
|---|---|---|---|---|---|---|---|---|---|---|---|---|---|---|---|
| | | | 100 | | | | | 105 | | | | | 110 | | |

| Ile | Glu | Val | Lys | Arg | Gly | Met | Asp | Lys | Ala | Ala | Glu | Ala | Ile | Ile | Asn |
|---|---|---|---|---|---|---|---|---|---|---|---|---|---|---|---|
| | | | 115 | | | | | 120 | | | | | 125 | | |

| Glu | Leu | Lys | Lys | Ala | Ser | Lys | Lys | Val | Gly | Gly | Lys | Glu | Glu | Ile | Thr |
|---|---|---|---|---|---|---|---|---|---|---|---|---|---|---|---|
| | 130 | | | | | 135 | | | | | 140 | | | | |

| Gln | Val | Ala | Thr | Ile | Ser | Ala | Asn | Ser | Asp | His | Asn | Ile | Gly | Lys | Leu |
|---|---|---|---|---|---|---|---|---|---|---|---|---|---|---|---|
| 145 | | | | | 150 | | | | | 155 | | | | | 160 |

| Ile | Ala | Asp | Ala | Met | Glu | Lys | Val | Gly | Lys | Asp | Gly | Val | Ile | Thr | Val |
|---|---|---|---|---|---|---|---|---|---|---|---|---|---|---|---|
| | | | | 165 | | | | | 170 | | | | | 175 | |

| Glu | Glu | Ala | Lys | Gly | Ile | Glu | Asp | Glu | Leu | Asp | Val | Val | Glu | Gly | Met |
|---|---|---|---|---|---|---|---|---|---|---|---|---|---|---|---|
| | | | | 180 | | | | | 185 | | | | | 190 | |

| Gln | Phe | Asp | Arg | Gly | Tyr | Leu | Ser | Pro | Tyr | Phe | Val | Thr | Asn | Ala | Glu |
|---|---|---|---|---|---|---|---|---|---|---|---|---|---|---|---|
| | | | 195 | | | | | 200 | | | | | 205 | | |

| Lys | Met | Thr | Ala | Gln | Leu | Asp | Asn | Ala | Tyr | Ile | Leu | Leu | Thr | Asp | Lys |
|---|---|---|---|---|---|---|---|---|---|---|---|---|---|---|---|
| | 210 | | | | | 215 | | | | | 220 | | | | |

| Lys | Ile | Ser | Ser | Met | Lys | Asp | Ile | Leu | Pro | Leu | Leu | Glu | Lys | Thr | Met |
|---|---|---|---|---|---|---|---|---|---|---|---|---|---|---|---|
| 225 | | | | | 230 | | | | | 235 | | | | | 240 |

| Lys | Glu | Gly | Lys | Pro | Leu | Leu | Ile | Ile | Ala | Glu | Asp | Ile | Glu | Gly | Glu |
|---|---|---|---|---|---|---|---|---|---|---|---|---|---|---|---|
| | | | | 245 | | | | | 250 | | | | | 255 | |

| Ala | Leu | Thr | Thr | Leu | Val | Val | Asn | Lys | Leu | Arg | Gly | Val | Leu | Asn | Ile |
|---|---|---|---|---|---|---|---|---|---|---|---|---|---|---|---|
| | | | 260 | | | | | 265 | | | | | 270 | | |

| Ala | Ala | Val | Lys | Ala | Pro | Gly | Phe | Gly | Asp | Arg | Arg | Lys | Glu | Met | Leu |
|---|---|---|---|---|---|---|---|---|---|---|---|---|---|---|---|
| | | 275 | | | | | 280 | | | | | 285 | | | |

| Lys | Asp | Ile | Ala | Val | Leu | Thr | Gly | Gly | Gln | Val | Ile | Ser | Glu | Glu | Leu |
|---|---|---|---|---|---|---|---|---|---|---|---|---|---|---|---|
| | 290 | | | | | 295 | | | | | 300 | | | | |

| Gly | Leu | Ser | Leu | Glu | Asn | Ala | Glu | Val | Glu | Phe | Leu | Gly | Lys | Ala | Gly |
|---|---|---|---|---|---|---|---|---|---|---|---|---|---|---|---|
| 305 | | | | | 310 | | | | | 315 | | | | | 320 |

| Arg | Ile | Val | Ile | Asp | Lys | Asp | Asn | Thr | Thr | Ile | Val | Asp | Gly | Lys | Gly |
|---|---|---|---|---|---|---|---|---|---|---|---|---|---|---|---|
| | | | 325 | | | | | 330 | | | | | 335 | | |

| His | Ser | Asp | Asp | Val | Lys | Asp | Arg | Val | Ala | Gln | Ile | Lys | Thr | Gln | Ile |
|---|---|---|---|---|---|---|---|---|---|---|---|---|---|---|---|
| | | | 340 | | | | | 345 | | | | | 350 | | |

| Ala | Ser | Thr | Thr | Ser | Asp | Tyr | Asp | Lys | Glu | Lys | Leu | Gln | Glu | Arg | Leu |
|---|---|---|---|---|---|---|---|---|---|---|---|---|---|---|---|
| | | | 355 | | | | | 360 | | | | | 365 | | |

| Ala | Lys | Leu | Ser | Gly | Gly | Val | Ala | Val | Ile | Lys | Val | Gly | Ala | Ala | Ser |
|---|---|---|---|---|---|---|---|---|---|---|---|---|---|---|---|
| | 370 | | | | | 375 | | | | | 380 | | | | |

Glu Val Glu Met Lys Glu Lys Asp Arg Val Asp Ala Leu Ser
385                 390                 395                 400

Ala Thr Lys Ala Ala Val Glu Glu Gly Ile Val Gly Gly Gly Ala
            405                 410                 415

Ala Leu Ile Arg Ala Ala Gln Lys Val His Leu Asn Leu His Asp Asp
            420                 425                 430

Glu Lys Val Gly Tyr Glu Ile Ile Met Arg Ala Ile Lys Ala Pro Leu
            435                 440                 445

Ala Gln Ile Ala Ile Asn Ala Gly Tyr Asp Gly Val Val Val Asn
            450                 455                 460

Glu Val Glu Lys His Glu Gly His Phe Gly Phe Asn Ala Ser Asn Gly
465                 470                 475                 480

Lys Tyr Val Asp Met Phe Lys Glu Gly Ile Ile Asp Pro Leu Lys Val
                485                 490                 495

Glu Arg Ile Ala Leu Gln Asn Ala Val Ser Val Ser Ser Leu Leu Leu
            500                 505                 510

Thr Thr Glu Ala Thr Val His Glu Ile Lys Glu Glu Lys Ala Ala Pro
            515                 520                 525

Ala Met Pro Asp Met Gly Gly Met Gly Gly Met Gly Gly Met Gly Gly
            530                 535                 540

Met Met
545

<210> SEQ ID NO 12
<211> LENGTH: 1641
<212> TYPE: DNA
<213> ORGANISM: H. pylori
<220> FEATURE:
<221> NAME/KEY: misc_feature
<223> OTHER INFORMATION: H. pylori strain G27

<400> SEQUENCE: 12

```
atggcaaaag aaatcaaatt ttcagatagt gcaagaaacc tttatttga aggcgtgaga        60 caactccatg atgctgtcaa agtaaccatg gggccaagag gcaggaatgt gttgattcaa      120
aaaagctatg gcgctccaag catcaccaaa gatggcgtga gcgtggctaa agagattgaa      180
ttaagttgcc cggtggctaa catgggcgct caactcgtta agaggtagc gagcaaaacc       240 gctgatgctg ccggcgatgg cacgaccaca gcgaccgtgc tggcttatag catttttaaa     300
gaaggtttga ggaatatcac ggctggggct aaccctattg aagtgaaacg aggcatggat     360
aaagccgctg aagcgatcat caatgagctt aaaaaagcga gcaaaaaagt aggcggtaaa    420
gaagaaatca cccaagtagc gaccatttct gccaactccg atcacaatat cgggaaactc    480
atcgctgacg ctatggaaaa agtgggtaaa gatggcgtga tcactgttga agaggctaag    540
ggcattgaag acgaattaga tgtcgtagaa ggcatgcaat tgatagagg ctatctctcc     600 ccttattttg taacgaacgc tgagaaaatg accgctcaat tggataacgc ttacatcctt    660
ttaacggata aaaaaatctc tagcatgaaa gacatcctcc cgctattgga aaaaccatg     720 aaagagggca accgctttt aatcatcgct gaagacattg agggcgaagc tttaacgact    780
ctagtggtga ataattaag aggcgtgttg aatatcgcag cggttaaagc tccaggcttt    840
ggggacagga gaaagaaat gctcaaagac atcgctgttt taaccggcgg tcaagtcatt    900
agcgaagaat tgggcttgag tctagaaaac gctgaagtgg agttttagg caaagccgga     960 aggattgtga ttgacaaaga caacaccacg atcgtagatg gcaaaggcca tagcgatgat   1020
```

-continued

```
gttaaagaca gagtcgcgca atcaaaacc caaattgcaa gcacgacaag cgattatgac    1080
aaagaaaaat tgcaagaaag gttggccaaa ctctctggcg gtgtggctgt gattaaagtg    1140
ggcgctgcga gtgaagtgga atgaaagag aaaaagacc gggtggatga cgcgttgagc     1200
gcgactaaag cggcggttga agaaggcatt gtgattggcg gcggtgcggc tcttattcgc    1260
gcggctcaaa aagtgcattt gaatttacac gatgatgaaa agtgggcta tgaaatcatc    1320 atgcgcgcca ttaaagcccc attagctcaa atcgctatca atgccggtta tgatggcggt    1380
gtggtcgtga atgaagtaga aaaacacgaa gggcattttg gttttaacgc tagcaatggc    1440
aagtatgtgg acatgtttaa agaaggcatt attgaccct aaaagtaga aaggatcgct     1500 ttgcaaaatg cggtttcggt ttcaagcctg cttttaacca cagaagccac cgtgcatgaa    1560
atcaaagaag aaaaagcggc cccggcaatg cctgatatgg gtggcatggg cggtatggga    1620
ggcatgggcg gcatgatgta a                                              1641
```

<210> SEQ ID NO 13
<211> LENGTH: 265
<212> TYPE: PRT
<213> ORGANISM: H. pylori
<220> FEATURE:
<221> NAME/KEY: MISC_FEATURE
<223> OTHER INFORMATION: H. pylori 26695

<400> SEQUENCE: 13

```
Met Ile Leu Arg Ala Ser Val Leu Ser Ala Leu Leu Val Gly Leu
1               5                   10                  15

Gly Ala Ala Pro Lys His Ser Val Ser Ala Asn Asp Lys Arg Met Gln
            20                  25                  30

Asp Asn Leu Val Ser Val Ile Glu Lys Gln Thr Asn Lys Lys Val Arg
        35                  40                  45

Ile Leu Glu Ile Lys Pro Leu Lys Ser Ser Gln Asp Leu Lys Met Val
    50                  55                  60

Val Ile Glu Asp Pro Asp Thr Lys Tyr Asn Ile Pro Leu Val Val Ser
65                  70                  75                  80

Lys Asp Gly Asn Leu Ile Ile Gly Leu Ser Asn Ile Phe Phe Ser Asn
                85                  90                  95

Lys Ser Asp Asp Val Gln Leu Val Ala Glu Thr Asn Gln Lys Val Gln
            100                 105                 110

Ala Leu Asn Ala Thr Gln Gln Asn Ser Ala Lys Leu Asn Ala Ile Phe
        115                 120                 125

Asn Glu Ile Pro Ala Asp Tyr Ala Ile Glu Leu Pro Ser Thr Asn Ala
    130                 135                 140

Ala Asn Lys Asp Lys Ile Leu Tyr Ile Val Ser Asp Pro Met Cys Pro
145                 150                 155                 160

His Cys Gln Lys Glu Leu Thr Lys Leu Arg Asp His Leu Lys Glu Asn
                165                 170                 175

Thr Val Arg Met Val Val Gly Trp Leu Gly Val Asn Ser Ala Lys
            180                 185                 190

Lys Ala Ala Leu Ile Gln Glu Glu Met Ala Lys Ala Arg Ala Arg Gly
        195                 200                 205

Ala Ser Val Glu Asp Lys Ile Ser Ile Leu Glu Lys Ile Tyr Ser Thr
    210                 215                 220

Gln Tyr Asp Ile Asn Ala Gln Lys Glu Pro Glu Asp Leu Arg Thr Lys
225                 230                 235                 240

Val Glu Asn Thr Thr Lys Lys Ile Phe Glu Ser Gly Val Ile Lys Gly
```

Val Pro Phe Leu Tyr His Tyr Lys Ala
        260                 265

<210> SEQ ID NO 14
<211> LENGTH: 798
<212> TYPE: DNA
<213> ORGANISM: H. pylori
<220> FEATURE:
<221> NAME/KEY: misc_feature
<223> OTHER INFORMATION: H. pylori 26695

<400> SEQUENCE: 14

```
atgatattaa gagcgagtgt gttgagcgcg ttacttcttg taggcttagg ggcagcccct      60
aaacattcag tttcagctaa tgacaaacgg atgcaggata atttagtgag cgtgattgaa     120
aaacagacca ataaaaaggt gcgtatttta gaaatcaaac ctttaaaatc tagccaggat     180
ttaaaaatgg tcgttattga agatccggac actaaataca atatcccgct tgtggtgagt     240
aaggatggta atttaatcat agggcttagc aacatattct ttagcaataa aagcgatgat     300
gtgcaattag ttgcagaaac caatcaaaaa gttcaagctc ttaacgccac ccaacaaaat     360
agcgcgaaat tgaacgctat ttttaatgaa ataccggctg attatgcgat agagttgccc     420
tctactaacg ctgcaaataa ggataaaatc ctttatattg tctctgatcc catgtgccca     480
cattgccaaa aagagctcac taaacttagg gatcatttaa agaaaacac cgtgagaatg     540
gtcgtggtgg ggtggcttgg ggtcaattca gctaaaaaag cggctttaat ccaagaagaa     600
atggcgaaag ctagggctag gggagcgagc gtggaagata agatctctat tcttgaaaag     660
atttattcca cccaatacga tattaacgct caaaagagc ctgaagattt acgcactaaa     720
gtggaaaata ccactaaaaa gattttgaa tctggcgtga ttaagggtgt gcctttctta     780
taccattata aggcatga                                                 798
```

<210> SEQ ID NO 15
<211> LENGTH: 325
<212> TYPE: PRT
<213> ORGANISM: H. pylori
<220> FEATURE:
<221> NAME/KEY: MISC_FEATURE
<223> OTHER INFORMATION: H. pylori J99

<400> SEQUENCE: 15

Met Pro Thr Ile Asp Phe Thr Phe Cys Glu Ile Asn Pro Lys Lys Gly
1               5                   10                  15

Phe Gly Gly Ala Asn Gly Asn Lys Ile Ser Leu Phe Tyr Asn Asn Glu
            20                  25                  30

Leu Tyr Met Val Lys Phe Pro Pro Lys Pro Ser Thr His Lys Glu Met
        35                  40                  45

Ser Tyr Thr Asn Gly Cys Phe Ser Glu Tyr Val Ala Cys His Ile Val
    50                  55                  60

Asn Ser Leu Gly Leu Lys Val Gln Glu Thr Leu Leu Gly Thr Tyr Lys
65                  70                  75                  80

Asn Lys Ile Val Val Ala Cys Lys Asp Phe Thr Thr His Gln Tyr Glu
                85                  90                  95

Leu Val Asp Phe Leu Ser Leu Lys Asn Thr Met Ile Glu Leu Glu Lys
            100                 105                 110

Ser Gly Lys Asp Thr Asn Leu Asn Asp Val Leu Tyr Ala Ile Asp Asn
        115                 120                 125

Gln His Phe Ile Glu Pro Lys Val Leu Lys Cys Phe Phe Trp Asp Met
    130                 135                 140

Phe Val Ala Asp Thr Leu Leu Gly Asn Phe Asp Arg His Asn Gly Asn
145                 150                 155                 160

Trp Gly Phe Leu Arg Ala Ser Asn Ser Lys Glu Tyr Gln Ile Ala Pro
                165                 170                 175

Ile Phe Asp Cys Gly Ser Cys Leu Tyr Pro Gln Ala Asp Asp Val Val
            180                 185                 190

Cys Gln Lys Val Leu Ser Asn Ile Asp Glu Leu Asn Ala Arg Ile Tyr
        195                 200                 205

Asn Phe Pro Gln Ser Ile Leu Lys Asp Asn Asp Lys Lys Ile Asn
    210                 215                 220

Tyr Tyr Asp Phe Leu Thr Gln Thr Asn Asn Lys Asp Cys Leu Asp Ala
225                 230                 235                 240

Leu Leu Arg Ile Tyr Pro Arg Ile Asp Met Asn Lys Ile His Ser Ile
                245                 250                 255

Ile Asp Asn Thr Pro Phe Met Ser Glu Ile His Lys Glu Phe Leu His
            260                 265                 270

Thr Met Leu Asp Glu Arg Lys Ser Lys Ile Ile Asp Val Ala His Thr
        275                 280                 285

Arg Ala Ile Glu Leu Ser Leu Gln His Lys Gln Ala His Ser Asn Pro
    290                 295                 300

Tyr Asp Asn Ala Asp Asp Leu Asp Asn Ser Asn Glu Tyr Thr Pro Thr
305                 310                 315                 320

Pro Lys Arg Arg Arg
            325

<210> SEQ ID NO 16
<211> LENGTH: 978
<212> TYPE: DNA
<213> ORGANISM: H. pylori
<220> FEATURE:
<221> NAME/KEY: misc_feature
<223> OTHER INFORMATION: H. pylori J99

<400> SEQUENCE: 16
atgccaacca ttgattttac tttttgtgag attaacccta aaaaggtttt tgggggagca      60
aatggaaata aaattagctt attttataat aatgaactct acatggtcaa attccccccct    120 aagccttcta cacataaaga aatgtcctat accaatggtt gttttagtga atatgtagca    180
tgtcatatag tcaatagctt aggcttaaag gttcaagaaa cattgctagg cacttataaa    240
aataaaatcg tggttgcttg taaagatttt accaccccatc aatacgagct tgtagatttt    300
ctaagtctaa aaatactat gattgaatta gaaaaatcag gcaaagacac taatttgaat    360
gatgtgcttt atgccataga taaccagcat tttattgagc caaagttttt aaaatgtttc    420
ttttgggata tgtttgtagc agatacattg ctaggtaatt ttgataggca taatggtaat    480
tgggggttct taagagcctc aaattcaaaa gaatatcaaa tagctcccat ttttgattgt    540
ggctcttgtc tatacccca agctgatgat gtggtatgcc aaaaagtttt aagtaatatt    600
gatgaactca atgcaaggat ttataatttc ccccaatcta tcttaaaaga tgacaacgat    660
aaaaaaatta actactatga tttcttaact caaaccaata taaagattg ccttgatgca    720 ctacttagga tacccacg catagatatg aataaaatcc attcaattat tgataacaca    780
ccctttatga gcgaaataca caagaatttt ttacatacaa tgcttgatga agaaaatca    840 aagattatag atgtagcaca cactagagct attgagttat ccttacaaca caaacaagct    900

```
cactcaaacc cttatgacaa cgcagatgat ttagacaatt ccaatgaata caccccaca      960 cctaagcgta gacgataa                                                    978
```

<210> SEQ ID NO 17
<211> LENGTH: 476
<212> TYPE: PRT
<213> ORGANISM: H. pylori
<220> FEATURE:
<221> NAME/KEY: MISC_FEATURE
<223> OTHER INFORMATION: H. pylori strain G27

<400> SEQUENCE: 17

```
Met Met Lys Lys Thr Leu Phe Ile Ser Leu Ala Leu Ala Leu Ser Leu
1               5                   10                  15

Asn Ala Gly Asn Ile Gln Ile Gln Asn Met Pro Lys Val Lys Glu Arg
            20                  25                  30

Val Ser Val Pro Ser Lys Asp Asp Thr Ile Tyr Ser Tyr His Asp Ser
        35                  40                  45

Ile Lys Asp Ser Ile Lys Ala Val Val Asn Ile Ser Thr Glu Lys Lys
    50                  55                  60

Ile Lys Asn Asn Phe Ile Gly Gly Val Phe Asn Asp Pro Phe Phe
65                  70                  75                  80

Gln Gln Phe Phe Gly Asp Leu Gly Gly Met Ile Pro Lys Glu Arg Met
                85                  90                  95

Glu Arg Ala Leu Gly Ser Gly Val Ile Ile Ser Lys Asp Gly Tyr Ile
            100                 105                 110

Val Thr Asn Asn His Val Ile Asp Gly Ala Asp Lys Ile Lys Val Thr
        115                 120                 125

Ile Pro Gly Ser Asn Lys Glu Tyr Ser Ala Thr Leu Val Gly Thr Asp
    130                 135                 140

Ser Glu Ser Asp Leu Ala Val Ile Arg Ile Thr Lys Asp Asn Leu Pro
145                 150                 155                 160

Thr Ile Lys Phe Ser Asp Ser Asn Asp Ile Ser Val Gly Asp Leu Val
                165                 170                 175

Phe Ala Ile Gly Asn Pro Phe Gly Val Gly Glu Ser Val Thr Gln Gly
            180                 185                 190

Ile Val Ser Ala Leu Asn Lys Ser Gly Ile Gly Ile Asn Ser Tyr Glu
        195                 200                 205

Asn Phe Ile Gln Thr Asp Ala Ser Ile Asn Pro Gly Asn Ser Gly Gly
    210                 215                 220

Ala Leu Ile Asp Ser Arg Gly Gly Leu Val Gly Ile Asn Thr Ala Ile
225                 230                 235                 240

Ile Ser Lys Thr Gly Gly Asn His Gly Ile Gly Phe Ala Ile Pro Ser
                245                 250                 255

Asn Met Val Lys Asp Ile Val Thr Gln Leu Ile Lys Thr Gly Lys Ile
            260                 265                 270

Glu Arg Gly Tyr Leu Gly Val Gly Leu Gln Asp Leu Ser Gly Asp Leu
        275                 280                 285

Gln Asn Ser Tyr Asp Asn Lys Glu Gly Ala Val Val Ile Ser Val Glu
    290                 295                 300

Lys Asp Ser Pro Ala Lys Lys Val Gly Ile Leu Val Trp Asp Leu Ile
305                 310                 315                 320

Thr Glu Val Asn Gly Lys Lys Val Lys Asn Thr Asn Glu Leu Arg Asn
                325                 330                 335
```

```
Leu Ile Gly Ser Met Leu Pro Asn Gln Arg Val Thr Leu Lys Val Ile
            340                 345                 350

Arg Asp Lys Lys Glu Arg Thr Phe Thr Leu Thr Leu Ala Glu Arg Lys
        355                 360                 365

Asn Pro Asn Lys Lys Glu Thr Ile Ser Ala Gln Asn Gly Ala Gln Gly
    370                 375                 380

Gln Leu Asn Gly Leu Gln Val Glu Asp Leu Thr Gln Lys Thr Lys Arg
385                 390                 395                 400

Ser Met Arg Leu Ser Asp Asp Val Gln Gly Val Leu Val Ser Gln Val
                405                 410                 415

Asn Glu Asn Ser Pro Ala Glu Gln Ala Gly Phe Arg Gln Gly Asn Ile
            420                 425                 430

Ile Thr Lys Ile Glu Glu Ile Glu Val Lys Ser Val Ala Asp Phe Asn
        435                 440                 445

His Ala Leu Glu Lys Tyr Lys Gly Lys Pro Lys Arg Phe Leu Val Leu
    450                 455                 460

Asp Leu Asn Gln Gly Tyr Arg Ile Ile Leu Val Lys
465                 470                 475
```

<210> SEQ ID NO 18
<211> LENGTH: 1431
<212> TYPE: DNA
<213> ORGANISM: H. pylori
<220> FEATURE:
<221> NAME/KEY: misc_feature
<223> OTHER INFORMATION: H. pylori G27

<400> SEQUENCE: 18

```
atgatgaaaa aaccccttttt tatctctttg ctttagcgt taagcttgaa tgcgggcaat      60
atccaaatcc aaaacatgcc caaagttaaa gagcgagtga gtgtcccctc taaagacgat    120
acgatctatt cttaccacga ttctattaag gattcgatta aagcggtggt gaatatctct    180
actgaaaaga agattaaaaa caatttttata ggtggcggtg tgtttaatga ccccttttttc  240
caacaattttt ttgggggatttt gggcggcatg atccctaaag aaagaatgga aagggcttta   300
ggcagcggcg taatcatttc taaagatggc tatattgtaa ctaacaacca tgtgattgat    360
ggtgcggata agattaaagt taccattcca gggagcaata aagagtattc cgctacttta    420
gtaggcaccg attctgaaag cgatttagcc gtgattcgca tcactaaaga caatctgccc    480
accatcaaat tctctgattc taacgatatt tcagtgggcg atttggtttt tgcgattggt    540
aaccccttttg gcgtgggtga aagcgttact caaggcattg tttcagcgct caataaaagc    600
gggattggga tcaacagcta tgaaaatttc attcaaacag acgcttccat caatcctgga    660
aattccggcg gcgctttaat tgatagccgt ggagggttag tggggatcaa taccgccatt    720
atctctaaaa ccggggggcaa ccacggcatt ggctttgcca tccccttctaa catggttaaa    780
gatattgtaa cccaactcat caaaaccggt aagattgaaa gaggttactt gggcgtgggc    840
ttgcaagatt tgagcggcga tttgcaaaat tcttatgaca taaagaagg gcggtagtc    900
attagcgtag aaaaagactc tccggctaaa aaagtaggga ttttggtgtg ggattttgatc    960
actgaagtca atgggaaaaa ggttaaaaac acgaatgagt taagaaatct aatcggctcc   1020
atgctaccca atcaaagagt aaccttaaaa gtcattagag acaaaaaaga acgcactttc   1080
acctcactc ttgctgaaag gaaaaaccct aacaaaaaag aaaccatttc tgctcaaaac   1140
ggcgcgcaag gccaattgaa cgggcttcaa gtagaagatt taacccaaaa aaccaaaagg   1200
tctatgcgtt tgagcgatga tgttcaaggg gttttagtct ctcaagtgaa tgaaaattcc   1260
```
ccagcagagc aagctggctt taggcaaggc aatatcatca caaaaattga agagattgaa    1320
gtgaaaagcg ttgcggattt taaccatgct ttagaaaagt ataaaggcaa acccaaacga    1380
ttcttagttt tagatttgaa tcaaggttat aggatcattt tggtgaaatg a             1431

<210> SEQ ID NO 19
<211> LENGTH: 22
<212> TYPE: DNA
<213> ORGANISM: Artificial
<220> FEATURE:
<223> OTHER INFORMATION: Synthetic

<400> SEQUENCE: 19
catatggcaa taggttcatt aa                                               22

<210> SEQ ID NO 20
<211> LENGTH: 24
<212> TYPE: DNA
<213> ORGANISM: Artificial
<220> FEATURE:
<223> OTHER INFORMATION: Synthetic

<400> SEQUENCE: 20
ctcgagattc tttttagccg ctgc                                             24

<210> SEQ ID NO 21
<211> LENGTH: 20
<212> TYPE: DNA
<213> ORGANISM: Artificial
<220> FEATURE:
<223> OTHER INFORMATION: Primer

<400> SEQUENCE: 21
agctcattag ggcttggcag                                                  20

<210> SEQ ID NO 22
<211> LENGTH: 18
<212> TYPE: DNA
<213> ORGANISM: Artificial
<220> FEATURE:
<223> OTHER INFORMATION: Primer

<400> SEQUENCE: 22
gctcgcgctc aacgcatc                                                    18

<210> SEQ ID NO 23
<211> LENGTH: 20
<212> TYPE: DNA
<213> ORGANISM: Artificial
<220> FEATURE:
<223> OTHER INFORMATION: Primer

<400> SEQUENCE: 23
atcacggacg ctaccaatgg                                                  20

<210> SEQ ID NO 24
<211> LENGTH: 20
<212> TYPE: DNA
<213> ORGANISM: Artificial
<220> FEATURE:
<223> OTHER INFORMATION: Primer

<400> SEQUENCE: 24
agggacttca tgcatgctcc                                                  20

```
<210> SEQ ID NO 25
<211> LENGTH: 21
<212> TYPE: DNA
<213> ORGANISM: Artificial
<220> FEATURE:
<223> OTHER INFORMATION: Primer

<400> SEQUENCE: 25
cacagacgct atcattcaag c                                            21

<210> SEQ ID NO 26
<211> LENGTH: 21
<212> TYPE: DNA
<213> ORGANISM: Artificial
<220> FEATURE:
<223> OTHER INFORMATION: Primer

<400> SEQUENCE: 26
cccgctgatc acatcattga c                                            21

<210> SEQ ID NO 27
<211> LENGTH: 21
<212> TYPE: DNA
<213> ORGANISM: Artificial
<220> FEATURE:
<223> OTHER INFORMATION: Primer

<400> SEQUENCE: 27
cgctaacctc atagatggag g                                            21

<210> SEQ ID NO 28
<211> LENGTH: 19
<212> TYPE: DNA
<213> ORGANISM: Artificial
<220> FEATURE:
<223> OTHER INFORMATION: Primer

<400> SEQUENCE: 28
taagcggcaa agcgctccg                                               19
```